US011535671B2

(12) United States Patent
Hegde et al.

(10) Patent No.: US 11,535,671 B2
(45) Date of Patent: Dec. 27, 2022

(54) THERAPEUTIC AND DIAGNOSTIC METHODS FOR CANCER

(71) Applicant: Genentech, Inc., South San Francisco, CA (US)

(72) Inventors: Priti Hegde, South San Francisco, CA (US); Marcin Kowanetz, South San Francisco, CA (US); Gregg Fine, South San Francisco, CA (US); Sanjeev Mariathasan, South San Francisco, CA (US); Richard Bourgon, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 209 days.

(21) Appl. No.: 16/655,495

(22) Filed: Oct. 17, 2019

(65) Prior Publication Data
US 2020/0031936 A1    Jan. 30, 2020

Related U.S. Application Data

(63) Continuation of application No. 15/790,680, filed on Oct. 23, 2017, now abandoned, which is a continuation of application No. PCT/US2016/034664, filed on May 27, 2016.

(60) Provisional application No. 62/301,599, filed on Feb. 29, 2016, provisional application No. 62/168,669, filed on May 29, 2015.

(51) Int. Cl.
C07K 16/28      (2006.01)
C12Q 1/6886    (2018.01)
G01N 33/574    (2006.01)
A61K 39/00      (2006.01)

(52) U.S. Cl.
CPC ........ C07K 16/2827 (2013.01); C12Q 1/6886 (2013.01); G01N 33/57407 (2013.01); A61K 2039/505 (2013.01); C07K 2317/24 (2013.01); C07K 2317/76 (2013.01); C07K 2319/30 (2013.01); C12Q 2600/106 (2013.01); C12Q 2600/158 (2013.01); C12Q 2600/178 (2013.01); G01N 2333/70532 (2013.01); G01N 2800/52 (2013.01)

(58) Field of Classification Search
None
See application file for complete search history.

(56) References Cited

U.S. PATENT DOCUMENTS

2015/0071910 A1    3/2015 Kowanetz et al.
2016/0287699 A1 * 10/2016 Karkera .................. A61P 35/00

FOREIGN PATENT DOCUMENTS

WO   WO-2013/173223 A1    11/2013
WO   WO-2014085666 A1 *   6/2014   .......... A61K 31/185
WO   2014/151006 A2 †     9/2014
WO   WO-2014/151006 A2    9/2014
WO   WO-2014/194293 A1   12/2014
WO   WO-2016/196298 A1   12/2016

OTHER PUBLICATIONS

Choi et al. (Cancer Cell Feb. 10, 2014, 25: 152-165) (Year: 2014).*
Bajorin et al., "Keynote-052: Phase 2 study of pembrolizumab (MK-3475) as first-line therapy for patients (pts) with unresectable or metastatic urothelial cancer ineligible for cisplatin-based therapy," Journal of Clinical Oncology. 33:(15_suppl). Abstract TPS4572 (2015) (1 page).
Bellmunt et al., "Association of PD-L1 expression on tumor-infiltrating mononuclear cells and overall survival in patients with urothelial carcinoma," Ann Oncol. 26(4): 812-817 (2015).
Gupta et al., "MP68-11: A Phase 1b Study of Pembrolizumab (Pembro; MK-3475) For Advanced Urothelial Cancer," The Journal of Urology. 193(4S): e861-e862 (2015).
Huang et al., "The prognostic significance of PD-L1 in bladder cancer," Oncol Rep. 33(6):3075-3084 (2015).
Plimack et al., "A Phase 1b Study of Pembrolizumab (Pembro; Mk-3475) In Patients (Pts) With Advanced Urothelial Tract Cancer," Annals of Oncology. 25 (Supplement 5): v1-v41 (2014).
Acknowledgement of receipt addressed to J A Kemp LLP for European Patent Application No. 16732373.2, dated Jul. 7, 2021 (1 page).
Notification of material filed by a third party for Australian Patent Application No. 2016270625, dated Jul. 29, 2021 (19 pages).
Summons to attend oral proceedings pursuant to Rule 115(1) EPC addressed to D Young & Co LLP for European Patent Application No. 16732373.2, dated Jul. 7, 2021 (31 pages).
Summons to attend oral proceedings pursuant to Rule 115(1) EPC addressed to J A Kemp LLP for European Patent Application No. 16732373.2, dated Jul. 7, 2021 (31 pages).

(Continued)

*Primary Examiner* — Peter J Reddig
(74) *Attorney, Agent, or Firm* — Clark & Elbing LLP; Thomas J. Takara

(57) ABSTRACT

The present invention provides therapeutic and diagnostic methods and compositions for cancer, for example, bladder cancer. The invention provides methods of treating bladder cancer, methods of determining whether a patient suffering from bladder cancer is likely to respond to treatment comprising a PD-L1 axis binding antagonist, methods of predicting responsiveness of a patient suffering from bladder cancer to treatment comprising a PD-L1 axis binding antagonist, and methods of selecting a therapy for a patient suffering from bladder cancer, based on expression levels of a biomarker of the invention (e.g., PD-L1 expression levels in tumor-infiltrating immune cells in a tumor sample obtained from the patient) and/or based on the determination of a tumor sample subtype.

33 Claims, 28 Drawing Sheets
(8 of 28 Drawing Sheet(s) Filed in Color)

Specification includes a Sequence Listing.

(56) References Cited

OTHER PUBLICATIONS

Summons to attend oral proceedings pursuant to Rule 115(1) EPC addressed to Merck Serono S.A, for European Patent Application No. 16732373.2, dated Jul. 7, 2021 (31 pages).
"BenchMark Ultra Advanced Staining System Operator Guide," Ventana Medical Systems, Inc. Nov. 2012 (322 pages).
"BenchMark XT and BenchMark LT Operator Manual," Ventana Medical Systems, Inc. (2012) (307 pages).
"History of Changes for Study: NCT02543645", submitted Sep. 4, 2015 (v1) <https://clinicaltrials.gov/ct2/history/NCT025436457V_1=View#StudyPageTop>, retrieved Nov. 19, 2020 (4 pages).
"International Nonproprietary Names for Pharmaceutical Substances (INN): proposed INN: List 112," World Health Organization. WHO Drug Information. 28(4):485-563 (2014).
"Roche presents positive results from pivotal study of investigational immunotherapy atezolizumab in specific type of advanced bladder cancer at 2015 European Cancer Congress," Roche Media Release, published Sep. 27, 2015 (5 pages).
"Roche provides update on Tecentriq US indication in prior-platinum treated metastatic bladder cancer," Roche Press Release, published Mar. 8, 2021, retrieved from <https://www.roche.com/investors/updates/inv-update-2021-03-08b.htm> Mar. 24, 2021 (4 pages).
Aggen et al., "Biomarkers for immunotherapy in bladder cancer: a moving target," J ImmunoTher Cancer. 5(1):94 (2017) (13 pages).
Balar et al., "Atezolizumab as first-line treatment in cisplatin-ineligible patients with locally advanced and metastatic urothelial carcinoma: a single-arm, multicentre, phase 2 trial," Lancet. 389(10064):67-76 (2017).
Balar et al., "Supplement to: Atezolizumab as first-line treatment in cisplatin-ineligible patients with locally advanced and metastatic urothelial carcinoma: a single-arm, multicentre, phase 2 trial," Lancet. 389(10064):67-76 (2017) (170 pages).
Ballman, "Biomarker: Predictive or Prognostic?" J Clin Oncol. 33(33):3968-71 (2015) (5 pages).
Bardoli et al., "The PD-1/PD-L1 axis in the pathogenesis of urothelial bladder cancer and evaluating its potential as a therapeutic target," Future Oncol. 12(5):595-600 (2016).
Bellmunt et al., "A review on the evolution of PD-1/PD-L1 immunotherapy for bladder cancer: The future is now," Cancer Treat Rev. 54:58-67 (2017).
Bidnur et al., "Inhibiting Immune Checkpoints for the Treatment of Bladder Cancer," Bladder Cancer. 2(1):15-25 (2016).
Cheng et al., "Biomarkers in bladder cancer: Translational and clinical implications," Crit Rev Oncol Hematol. 89(1):73-111 (2014).
Choi et al., "Intrinsic basal and luminal subtypes of muscle-invasive bladder cancer," Nat Rev Urol. 11(7):400-10 (2014).
Declaration of Sanjeev Mariathasan, PhD, dated Apr. 28, 2021 (3 pages).
Dong et al., "Tumor-associated B7-H1 promotes T-cell apoptosis: A potential mechanism of immune evasion," Nat Med. 8(8):793-800 (2002).
Gaisky et al., "Efficacy and safety of nivolumab monotherapy in patients with metastatic urothelial cancer (mUC) who have received prior treatment: Results from the phase II CheckMate 275 study," Annals of Oncology. 27(Supplement 6):vi552-vi587 (2016) (1 page).
Hedegaard et al., "Comprehensive Transcriptional Analysis of Early-Stage Urothelial Carcinoma," Cancer Cell. 30(1):27-42 (2016).
Kiselyov et al., "Key signaling pathways in the muscle-invasive bladder carcinoma: Clinical markers for disease modeling and optimized treatment," Int J Cancer. 138(11):2562-9 (2016).
Lavoie et al., "Predictive Biomarkers for Checkpoint Blockade in Urothelial Cancer: A Systematic Review," J Urol. 202(1):49-56 (2019).
Lenis et al., "Bladder cancer in 2014: From the genomic frontier to immunotherapeutics," Nat Rev Urol. 12(2):74-6 (2015) (2 pages).
Mariathasan et al., "TGF-beta attenuates tumour response to PD-L1 blockade by contributing to exclusion of T cells," available in PMC Aug. 14, 2018, published in final edited form as: Nature. 554(7693):544-548 (2018) (28 pages).
McConkey et al., "Genetic subtypes of invasive bladder cancer," Curr Opin Urol. 25(5):449-58 (2015).
Ohaegbulam et al., "Human cancer immunotherapy with antibodies to the PD-1 and PD-L1 pathway," available in PMC Jan. 1, 2016, published in final edited form as: Trends Mol Med. 21(1): 24-33 (2015) (23 pages).
Petrylak et al., "A phase 1a study of MPDL3280A (anti-PDL1): Updated response and survival data in urothelial bladder cancer (UBC)," Journal of Clinical Oncology. 33(15):Abstract 4501 (2015).
Plimack et al., "Pembrolizumab (MK-3475) for advanced urothelial cancer: Updated results and biomarker analysis from Keynote-012," Journal of Clinical Oncology. 33(15):Abstract 4502 (2015).
Powles et al., "Atezolizumab versus chemotherapy in patients with platinum-treated locally advanced or metastatic urothelial carcinoma (IMvigor211): a multicentre, open-label, phase 3 randomised controlled trial," Lancet. 391(10122):748-57 (2018).
Powles et al., "Immune biomarkers associated with clinical benefit from atezolizumab (MPDL3280a; anti-PD-L1) in advanced urothelial bladder cancer (UBC)," 30th Annual Meeting and Associated Programs of the Society for Immunotherapy of Cancer, Nov. 4-8, National Harbor, MD. Journal for ImmunoTherapy of Cancer. 3(Suppl 2):P83 (2015) (2 pages).
Powles et al., "MPDL3280A (anti-PD-L1) treatment leads to clinical activity in metastatic bladder cancer," Nature. 515(7528): 558-62 (includes supplemental content) (2014) (12 pages).
Rosenberg et al., "Atezolizumab in patients (pts) with locally-advanced or metastatic urothelial carcinoma (mUC): Results from a pivotal multicenter phase II study (IMvigor 210)," European Journal of Cancer. 51(3):S720 (2015).
Rosenberg et al., "Atezolizumab in patients with locally advanced and metastatic urothelial carcinoma who have progressed following treatment with platinum-based chemotherapy: a single arm, phase 2 trial," available in PMC Jun. 22, 2017, published in final edited form as: Lancet. 387(10031 ):1909-20 (2016) (22 pages).
Rosenberg et al., "Atezolizumab in patients with locally advanced and metastatic urothelial carcinoma who have progressed following treatment with platinum-based chemotherapy: a single-arm, multicentre, phase 2 trial," Lancet. 387(10031):1909-20 (2016).
Rosenberg et al., "Supplement to: Atezolizumab in patients with locally advanced and metastatic urothelial carcinoma who have progressed following treatment with platinum-based chemotherapy: a single-arm, multicentre, phase 2 trial," Lancet. 387(10031):1909-20 (2016) (25 pages).
Seront et al., "Molecular biology and targeted therapies for urothelial carcinoma," Cancer Treat Rev. 41(4):341-53 (2015).
Sharma et al., "Nivolumab in metastatic urothelial carcinoma after platinum therapy (CheckMate 275): a multicentre, single-arm, phase 2 trial," Lancet Oncol. 18(3):312-22 (2017).
Sharma et al., "Supplement to: Nivolumab in metastatic urothelial carcinoma after platinum therapy (CheckMate 275): a multicentre, single-arm, phase 2 trial," Lancet Oncol. 18(3):312-22 (2017) (130 pages).
Snyder et al., "Contribution of systemic and somatic factors to clinical response and resistance to PD-L1 blockade in urothelial cancer: An exploratory multi-omic analysis," PLOS Med. 14(5):e1002309 (2017) (24 pages).
The Cancer Genome Atlas Research Network, "Comprehensive Molecular Characterization of Urothelial Bladder Carcinoma," available in PMC Sep. 20, 2014, published in final edited form as: Nature. 507(7492):315-322 (2014) (21 pages).
Zhu et al., "Traditional Classification and Novel Subtyping Systems for Bladder Cancer," Front Oncol. 10:102 (2020) (13 pages).
Brief Communication for European Patent Application No. 16732373.2 addressed to J A Kemp LLP, dated May 10, 2021 (107 pages).
Brief Communication for European Patent Application No. 16732373.2 addressed to Merck Serono S.A., dated May 10, 2021 (107 pages).
Communication of a Notice of Opposition for European Patent Application No. 16732373.2, dated Dec. 14, 2020 (78 pages).
Communication of Further Notices of Opposition pursuant to Rule 79(2) EPC for European Patent Application No. 16732373.2 addressed to J A Kemp LLP, dated Dec. 23, 2020 (33 pages).

(56) References Cited

OTHER PUBLICATIONS

Communication of Further Notices of Opposition pursuant to Rule 79(2) EPC for European Patent Application No. 16732373.2 addressed to Merck Serono S.A., dated Dec. 23, 2020 (48 pages).
Communication of Notices of Opposition (R. 79(1) EPC) for European Patent Application No. 16732373.2, dated Dec. 23, 2020 (1 page).
Decision to Grant a European Patent pursuant to Article 97(1) EPC for European Patent Application No. 16732373.2, dated Feb. 6, 2020 (2 pages).
English Translation of First Office Action for Chinese Patent Application No. 201680025629.9, dated Nov. 17, 2020 (12 pages).
Extended European Search Report for European Patent Application No. EP 20152796.7, dated Jul. 24, 2020 (9 pages).
Notice of Opposition to a European Patent for European Patent Application No. 16732373.2, Opponent—Ares Trading S.A., dated Dec. 4, 2020 (30 pages).
Notice of Opposition to a European patent for European Patent Application No. 16732373.2, Opponent—GlaxoSmithKline Intellectual Property Development Limited, dated Dec. 4, 2020 (45 pages).
Notice of Reasons for Rejection for Japanese Patent Application No. 2017-561797, dated Mar. 9, 2021 (8 pages).
Notice of Recordation of Assignment Document for U.S. Appl. No. 62/168,669, dated Feb. 8, 2016 (5 pages).
Notice of Recordation of Assignment Document for U.S. Appl. No. 62/301,599, dated Apr. 22, 2016 (5 pages).
Notification of Defects for Israeli Patent Application No. 255372, dated Dec. 27, 2020 (8 pages).
Reply of the Patent Proprietor to the Notice(s) of opposition for European Patent Application No. 16732373.2, issued Apr. 30, 2021 (50 pages).
Updated consolidated list of cited opposition documents for European Patent Application No. 16732373.2, issued Apr. 30, 2021 (3 pages).
Bellmunt et al. "Phase III trial of vinflunine plus best supportive care compared with best supportive care alone after a platinum-containing regimen in patients with advanced transitional cell carcinoma of the urothelial tract," J Clin Oncol. 27(27):4454-61 (2009).
Sternberg et al. "Preliminary results of M-VAC (methotrexate, vinblastine, doxorubicin and cisplatin) for transitional cell carcinoma of the urothelium," J Urol. 133(3):403-7 (1985).
Von der Maase et al. "Long-term survival results of a randomized trial comparing gemcitabine/cisplatin and methotrexate/vinblastine/doxorubicin/cisplatin in patients with locally advanced and metastatic bladder cancer," J Clin Oncol. 23(21):4602-8 (2005).
Notice of Reasons for Rejection for Japanese Patent Application No. 2017-561797, dated Mar. 31, 2020 (10 pages).
Herbst et al., "Predictive correlates of response to the anti-PD-L1 antibody MPDL3280A in cancer patients," Nature. 515(7528):563-7 (2014) (18 pages).
Communication pursuant to Article 94(3) for European Patent Application No. 16732373.2, dated Jan. 23, 2019 (4 pages).
International Preliminary Report on Patentability for International Patent Application No. PCT/US2016/034664, dated Dec. 5, 2017 (8 pages).
International Search Report and Written Opinion for International Patent Application No. PCT/US2016/034664, dated Oct. 25, 2016 (15 pages).
Invitation to Pay Additional Fees for International Patent Application No. PCT/US2016/034664, dated Aug. 30, 2016 (8 pages).
Bajorin et al., Keynote 052 Phase 2 study of pembrolizumab MK 3475 as first line therapy for patients pts with unresectable or metastatic urothelial cancer ineligible for cisplatin based therapy, Journal of Clinical Oncology.†
Gupta et .al, MP68 11 A Phase 1b Study of Pembrolizumab (Pembro; MK-3475) for Advanced Urothelial Cancer, The Journal of Urology.†
Plimack et al., A Phase 1b Study of Pembrolizumab (Pembro; Mk-3475) In Patients (Pts) With Advanced Urothelial Tract Cancer, Annals of Oncology.†
Bellmunt et al., Association of PD-L1 expression on tumor-infiltrating mononuclear cells and overall survival in patients with urothelial carcinoma, Annals of Oncology.†
Huang et al., The prognostic significance of PD-L1 in bladder cancer, Oncology Reports.†

* cited by examiner
† cited by third party

| PD-L1 prevalence in UBC | |
|---|---|
| IC Score (N = 205) | IC scored as PD-L1+, n (%) |
| IC3 | 18 (9%) |
| IC2 | 37 (18%) |
| IC1 | 89 (43%) |
| IC0 | 61 (30%) |

PD-L1 expression in ICs

FIG. 2

| PD-L1 IHC n = 87 | ORR, % (95% CI) | CR, n (%) | PR, n (%) |
|---|---|---|---|
| IC3 (n = 12) | 67% (35, 90) | 4 (33%) | 4 (33%) |
| IC2 (n = 34) | 44% (27, 62) | 5 (15%) | 10 (29%) |
| | 50% (35, 65) | 9 (20%) | 14 (30%) |
| IC1 (n = 26) | 19% (7, 39) | - | 5 (19%) |
| IC0 (n = 15) | 13% (2, 40) | - | 2 (13%) |
| | 17% (7, 32) | | 7 (17%) |

| Survival N = 92 | IC2/3 n = 48 | IC0/1 n = 44 |
|---|---|---|
| PFS | | |
| Median PFS (range) | 6 mo (0+ to 18) | 1 mo (0+ to 14+) |
| 1-year PFS (95% CI) | 39% (24-54) | 10% (0-21) |
| OS | | |
| Median OS (range) | Not reached (1 to 20+ mo) | 8 mo (1 to 15+ mo) |
| 1-year survival (95% CI) | 57% (41-73) | 38% (19-56) |

FIG. 5A

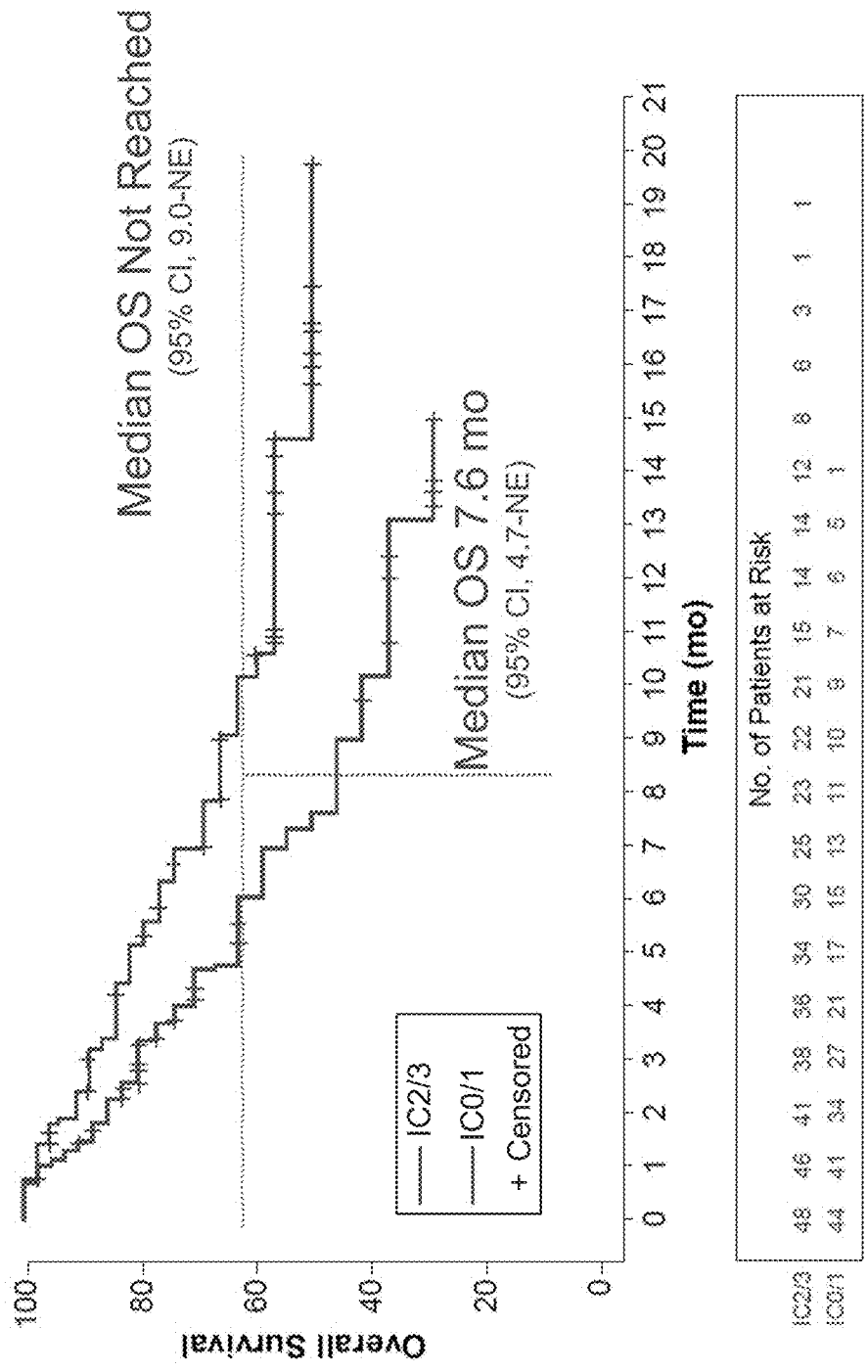

THERAPEUTIC AND DIAGNOSTIC METHODS FOR CANCER

SEQUENCE LISTING

The instant application contains a Sequence Listing which has been submitted electronically in ASCII format and is hereby incorporated by reference in its entirety. Said ASCII copy, created on Oct. 15, 2019, is named 50474-116004_Sequence_Listing_10.15.19_ST25 and is 23,684 bytes in size.

FIELD OF THE INVENTION

Provided herein are therapeutic and diagnostic methods and compositions for pathological conditions, such as cancer (e.g., bladder cancer (e.g., urothelial bladder cancer)), and methods of using PD-L1 axis binding antagonists. In particular, the invention provides biomarkers for patient selection and diagnosis, methods of treatment, articles of manufacture, diagnostic kits, and methods of detection.

BACKGROUND

Cancer remains one of the most deadly threats to human health. Cancers, or malignant tumors, metastasize and grow rapidly in an uncontrolled manner, making timely detection and treatment extremely difficult. In the U.S., cancer affects nearly 1.3 million new patients each year, and is the second leading cause of death after heart disease, accounting for approximately 1 in 4 deaths. Solid tumors are responsible for most of those deaths. Bladder cancer is the fifth-most common malignancy worldwide, with close to 400,000 newly diagnosed cases and approximately 150,000 associated deaths reported per year. In particular, metastatic urothelial bladder cancer is associated with poor outcomes and represents a major unmet medical need with few effective therapies to date.

Programmed death-ligand 1 (PD-L1) is a protein that has been implicated in the suppression of immune system responses during chronic infections, pregnancy, tissue allografts, autoimmune diseases, and cancer. PD-L1 regulates the immune response by binding to an inhibitory receptor, known as programmed death 1 (PD-1), which is expressed on the surface of T-cells, B-cells, and monocytes. PD-L1 negatively regulates T-cell function also through interaction with another receptor, B7-1. Formation of the PD-L1/PD-1 and PD-L1/B7-1 complexes negatively regulates T-cell receptor signaling, resulting in the subsequent downregulation of T-cell activation and suppression of anti-tumor immune activity.

Despite the significant advancement in the treatment of cancer (e.g., bladder cancer (e.g., urothelial bladder cancer)), improved therapies and diagnostic methods are still being sought.

SUMMARY OF THE INVENTION

The present invention provides therapeutic and diagnostic methods and compositions for cancer, for example, bladder cancer (e.g., urothelial bladder cancer).

In a first aspect, the invention features a method of treating a patient suffering from a bladder cancer, the method comprising administering to the patient a therapeutically effective amount of a PD-L1 axis binding antagonist, wherein a tumor sample obtained from the patient has been determined to have a detectable expression level of PD-L1 in tumor-infiltrating immune cells that comprise about 1% or more (e.g., about 1%, about 2%, about 3%, or about 4% or more) of the tumor sample. In some embodiments, a tumor sample obtained from the patient has been determined to have a detectable expression level of PD-L1 in tumor-infiltrating immune cells that comprise about 1% to about 65% or more (e.g., about 1% to about 5%, about 5% to about 10%, about 10% to about 20%, about 20% to about 30%, about 30% to about 40%, about 40% to about 50%, or about 50% to about 65%) of the tumor sample. In some embodiments, the median overall survival time of a patient administered a therapeutically effective amount of a PD-L1 axis binding antagonist is at least about 8 months. In some embodiments, the median overall survival time of a patient administered a therapeutically effective amount of a PD-L1 axis binding antagonist is at least about 8.8 months. In other embodiments, the median overall survival time of a patient administered a therapeutically effective amount of a PD-L1 axis binding antagonist is between at least about 7 to about 11 months. In another embodiment, the objective response rate of a patient administered a therapeutically effective amount of a PD-L1 axis binding antagonist is between about 10% to about 35% (e.g., about 10% to about 20%, about 20% to about 30%, about 30% to about 35%). In yet another embodiment, the objective response rate of a patient administered a therapeutically effective amount of a PD-L1 axis binding antagonist is between about 13% to about 24%. In other embodiments, the objective response rate of a patient administered a therapeutically effective amount of a PD-L1 axis binding antagonist is at least about 12%. In other embodiments, the objective response rate of a patient administered a therapeutically effective amount of a PD-L1 axis binding antagonist is at least about 21%. In some embodiments, the objective response rate of a patient administered a therapeutically effective amount of a PD-L1 axis binding antagonist is about 18%.

In some embodiments, the tumor sample obtained from the patient has been determined to have a detectable expression level of PD-L1 in tumor-infiltrating immune cells that comprise about 5% or more (e.g., about 5%, about 6%, about 7%, about 8%, or about 9% or more) of the tumor sample. In some embodiments, the median overall survival time of a patient administered a therapeutically effective amount of a PD-L1 axis binding antagonist is at least about 9 months. In some embodiments, the median overall survival time of a patient administered a therapeutically effective amount of a PD-L1 axis binding antagonist is at least about 11 months. In some embodiments, the median progression-free survival time of a patient administered a therapeutically effective amount of a PD-L1 axis binding antagonist is at least about 4 months. In some embodiments, the median progression-free survival time of a patient administered a therapeutically effective amount of a PD-L1 axis binding antagonist is between at least about 3 to about 6 months. In other embodiments, the objective response rate of a patient administered a therapeutically effective amount of a PD-L1 axis binding antagonist is between about 10% to about 45%. In some embodiments, the objective response rate of a patient administered a therapeutically effective amount of a PD-L1 axis binding antagonist is between about 35% to about 45%. In yet other embodiments, the objective response rate of a patient administered a therapeutically effective amount of a PD-L1 axis binding antagonist is between about 18% to about 37%. In other embodiments, the objective response rate of a patient administered a therapeutically effective amount of a PD-L1 axis binding antagonist is at least about 14%. In other embodiments, the objective response rate of a patient administered a therapeutically effective amount of a PD-L1 axis binding antagonist is at least about 25%. In some embodiments, the objective response rate of a patient administered a therapeutically effective amount of a PD-L1 axis binding antagonist is about 27%.

In some embodiments, the tumor sample obtained from the patient has been determined to have a detectable expression level of PD-L1 in tumor-infiltrating immune cells that comprise about 10% or more (e.g., about 10%, about 20%, about 30%, about 40% about 50%, or about 60% or more) of the tumor sample.

In other embodiments, the tumor sample obtained from the patient has been determined to be a luminal subtype tumor.

In a second aspect, the invention features a method of treating a patient suffering from a bladder cancer, the method comprising administering to the patient a therapeutically effective amount of a PD-L1 axis binding antagonist, wherein a tumor sample obtained from the patient has been determined to be a luminal subtype tumor.

In some embodiments of the first and second aspects, the expression level of at least one of CDKN2A, GATA3, FOXA1, and ERBB2 in the tumor sample obtained from the patient has been determined to be increased relative to a reference level of the at least one gene, and/or the expression level of at least one of FGFR3, KRT5, KRT14, and EGFR in the tumor sample obtained from the patient has been determined to be decreased relative to a reference level of the at least one gene. In some embodiments, the expression levels of CDKN2A, GATA3, FOXA1, and ERBB2 in the tumor sample obtained from the patient have been determined to be increased relative to reference levels of the genes, and/or the expression levels of FGFR3, KRT5, KRT14, and EGFR in the tumor sample obtained from the patient have been determined to be decreased relative to reference levels of the genes. In some embodiments, the expression levels of CDKN2A, GATA3, FOXA1, and ERBB2 in the tumor sample obtained from the patient have been determined to be increased relative to reference levels of the genes, and the expression levels of FGFR3, KRT5, KRT14, and EGFR in the tumor sample obtained from the patient have been determined to be decreased relative to reference levels of the genes. In other embodiments, the expression level of miR-99a-5p or miR100-5p in the tumor sample obtained from the patient has been determined to be increased relative to a reference level of the microRNA (miRNA). In some embodiments, the expression levels of miR-99a-5p and miR100-5p in the tumor sample obtained from the patient have been determined to be increased relative to reference levels of the miRNAs. In yet other embodiments, the expression level of at least one of CD8A, GZMA, GZMB, IFNG, CXCL9, CXCL10, PRF1, and TBX21 in the tumor sample obtained from the patient has been determined to be increased relative to a reference level of the at least one gene. In some embodiments, the expression levels of at least CXCL9 and CXCL10 in the tumor sample obtained from the patient have been determined to be increased relative to reference levels of the genes. In other embodiments, the luminal subtype tumor is a luminal cluster II subtype tumor.

In a third aspect, the invention features a method for determining whether a patient suffering from a bladder cancer is likely to respond to treatment comprising a PD-L1 axis binding antagonist, the method comprising determining the expression level of PD-L1 in tumor-infiltrating immune cells in a tumor sample obtained from the patient, wherein a detectable expression level of PD-L1 in tumor-infiltrating immune cells that comprise about 1% or more of the tumor sample indicates that the patient is likely to respond to treatment comprising a PD-L1 axis binding antagonist.

In a fourth aspect, the invention features a method for predicting responsiveness of a patient suffering from a bladder cancer to treatment comprising a PD-L1 axis binding antagonist, the method comprising determining the expression level of PD-L1 in tumor-infiltrating immune cells in a tumor sample obtained from the patient, wherein a detectable expression level of PD-L1 in tumor-infiltrating immune cells that comprise about 1% or more of the tumor sample indicates that the patient is likely to respond to treatment comprising a PD-L1 axis binding antagonist.

In a fifth aspect, the invention features a method for selecting a therapy for a patient suffering from a bladder cancer, the method comprising determining the expression level of PD-L1 in tumor-infiltrating immune cells in a tumor sample obtained from the patient, and selecting a therapy comprising a PD-L1 axis binding antagonist for the patient based on a detectable expression level of PD-L1 in tumor-infiltrating immune cells that comprise about 1% or more of the tumor sample.

In some embodiments of the third, fourth, and fifth aspects, the tumor sample obtained from the patient has been determined to have a detectable expression level of PD-L1 in tumor-infiltrating immune cells that comprise about 5% or more of the tumor sample. In some embodiments, the tumor sample obtained from the patient has been determined to have a detectable expression level of PD-L1 in tumor-infiltrating cells that comprise at least about 10% of the tumor sample.

In a sixth aspect, the invention features a method for determining whether a patient suffering from a bladder cancer is likely to respond to treatment comprising a PD-L1 axis binding antagonist, the method comprising determining from a tumor sample obtained from the patient the subtype of the tumor, wherein a luminal subtype tumor indicates that the patient is likely to respond to treatment comprising a PD-L1 axis binding antagonist.

In a seventh aspect, the invention features a method for predicting responsiveness of a patient suffering from a bladder cancer to treatment comprising a PD-L1 axis binding antagonist, the method comprising determining from a tumor sample obtained from the patient the subtype of the tumor, wherein a luminal subtype tumor indicates that the patient is likely to respond to treatment comprising a PD-L1 axis binding antagonist.

In an eighth aspect, the invention features a method for selecting a therapy for a patient suffering from a bladder cancer, the method comprising determining from a tumor sample obtained from the patient the subtype of the tumor, and selecting a therapy comprising a PD-L1 axis binding antagonist for the patient based on the determination that the tumor is a luminal subtype tumor.

In some embodiments of the third through eighth aspects, the method further comprises administering to the patient a therapeutically effective amount of a PD-L1 axis binding antagonist based on the expression level of PD-L1 in tumor-infiltrating immune cells in the tumor sample.

In some embodiments of any of the preceding aspects, the PD-L1 axis binding antagonist is selected from the group consisting of a PD-L1 binding antagonist, a PD-1 binding antagonist, and a PD-L2 binding antagonist. In some embodiments, the PD-L1 axis binding antagonist is a PD-L1 binding antagonist. In some embodiments, the PD-L1 binding antagonist inhibits the binding of PD-L1 to one or more of its ligand binding partners. In some embodiments, the PD-L1 binding antagonist inhibits the binding of PD-L1 to PD-1. In some embodiments, the PD-L1 binding antagonist inhibits the binding of PD-L1 to B7-1. In other embodiments, the PD-L1 binding antagonist inhibits the binding of PD-L1 to both PD-1 and B7-1. In yet other embodiments, the PD-L1 binding antagonist is an antibody. In some embodiments, the antibody is selected from the group consisting of atezolizumab (MPDL3280A), YW243.55.S70, MDX-1105, MED14736 (durvalumab), and MSB0010718C (avelumab). In some embodiments, the antibody comprises a heavy chain comprising HVR-H1 sequence of SEQ ID NO:19, HVR-H2 sequence of SEQ ID NO:20, and HVR-H3 sequence of SEQ ID NO:21, and a light chain comprising HVR-L1 sequence of SEQ ID NO:22, HVR-L2 sequence of SEQ ID NO:23, and HVR-L3 sequence of SEQ ID NO:24. In some embodiments, the antibody comprises a heavy chain variable region comprising the amino acid sequence of SEQ ID NO:26 and a light chain variable region comprising the amino acid sequence of SEQ ID NO:4. In other embodiments, the PD-L1 axis binding antagonist is a PD-1 binding antagonist. In some embodiments, the PD-1 binding antagonist inhibits the binding of PD-1 to one or more of its ligand binding partners. In some embodiments, the PD-1 binding antagonist inhibits the binding of PD-1 to PD-L1. In some embodiments, the PD-1 binding antagonist inhibits the binding of PD-1 to PD-L2. In other embodiments, the PD-1 binding antagonist inhibits the binding of PD-1 to both PD-L1 and PD-L2. In yet other embodiments, the PD-1 binding antagonist is an antibody. In some embodiments, the antibody is selected from the group consisting of MDX-1106 (nivolumab), MK-3475 (pembrolizumab), CT-011 (pidilizumab), MEDI-0680 (AMP-514), PDR001, REGN2810, and BGB-108. In other embodiments, the PD-1 binding antagonist is an Fc-fusion protein. In some embodiments, the Fc-fusion protein is AMP-224. In yet other embodiments, the method further comprises administering to the patient an effective amount of a second therapeutic agent. In some embodiments, the second therapeutic agent is selected from the group consisting of a cytotoxic agent, a growth-inhibitory agent, a radiation therapy agent, an anti-angiogenic agent, and combinations thereof. In other embodiments, the bladder cancer is an urothelial bladder cancer (UBC). In some embodiments, the UBC is a metastatic urothelial bladder cancer.

In other embodiments, the UBC is a locally advanced urothelial bladder cancer. In some embodiments, the patient has progressed following treatment with a platinum-based chemotherapeutic agent (i.e., the patient's disease (e.g., UBC) has progressed after prior treatment with a platinum-based chemotherapeutic agent). In yet other embodiments, the tumor sample is a formalin-fixed and paraffin-embedded (FFPE) tumor sample, an archival tumor sample, a fresh tumor sample, or a frozen tumor sample. In other embodiments, the expression level of PD-L1 is a protein expression level. In some embodiments, the protein expression level of PD-L1 is determined using a method selected from the group consisting of immunohistochemistry (IHC), immunofluorescence, flow cytometry, and Western blot. In some embodiments, the protein expression level of PD-L1 is determined using IHC. In other embodiments, the protein expression level of PD-L1 is detected using an anti-PD-L1 antibody. In yet other embodiments, the expression level of PD-L1 is an mRNA expression level. In some embodiments, the mRNA expression level of PD-L1 is determined using a method selected from the group consisting of quantitative polymerase chain reaction (qPCR), reverse transcription qPCR (RT-qPCR), RNA sequencing, microarray analysis, in situ hybridization, and serial analysis of gene expression (SAGE).

In a ninth aspect, the invention features a PD-L1 axis binding antagonist for use in treating a patient suffering from a bladder cancer, wherein a tumor sample obtained from the patient has been determined to have a detectable expression level of PD-L1 in tumor-infiltrating immune cells that comprise about 1% or more of the tumor sample.

In a tenth aspect, the invention features the use of an effective amount of a PD-L1 axis binding antagonist in the manufacture of a medicament for use in treating a patient suffering from a bladder cancer, wherein a tumor sample obtained from the patient has been determined to have a detectable expression level of PD-L1 in tumor-infiltrating immune cells that comprise about 1% or more of the tumor sample.

In an eleventh aspect, the invention features a composition comprising an effective amount of a PD-L1 axis binding antagonist for use in a method of treating a patient suffering from a bladder cancer, wherein a tumor sample obtained from the patient has been determined to have a detectable expression level of PD-L1 in tumor-infiltrating immune cells that comprise about 1% or more of the tumor sample.

BRIEF DESCRIPTION OF THE DRAWINGS

The application file contains at least one drawing executed in color. Copies of this patent or patent application with color drawings will be provided by the Office upon request and payment of the necessary fee.

FIG. 2 is a table showing that PD-L1 expression in ICs is associated with response of UBC patients to treatment with atezolizumab (MPDL3280A). The objective response rate (ORR), complete responses (CR), and partial responses (PR) are shown for patients with the indicated IC score. Efficacy-evaluable patients with measurable disease at baseline per RECIST v1.1. 4 IC2/3 patients and 7 IC0/1 patients were missing or unevaluable.

FIG. 5A is a table showing association of PD-L1 expression in ICs with survival in UBC patients treated with atezolizumab (MPDL3280A). The graph shows median and 1-year progression-free survival (PFS) and overall survival (OS) for IC2/3 and IC0/1 UBC patients treated with atezolizumab (MPDL3280A).

FIG. 5B is a graph showing OS for IC2/3 and IC0/1 UBC patients treated with atezolizumab (MPDL3280A).

DETAILED DESCRIPTION OF THE INVENTION

I. Introduction

Figures 1A, 1B:
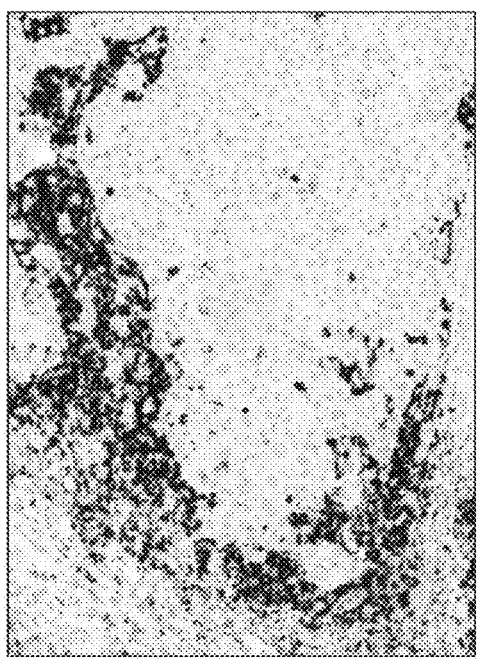
FIG. 1A is a table showing prevalence of PD-L1 expression at the indicated IC scores in UBC. The results are based on staining of archival tumor tissue from patients pre-screened in an ongoing Phase Ia clinical trial (see Example 2).
FIG. 1B is an image showing PD-L1 expression in tumor-infiltrating immune cells (ICs) as assessed by immunohistochemistry using a rabbit monoclonal anti-PD-L1 antibody. PD-L1 staining is shown in dark brown.

The present invention provides therapeutic and diagnostic methods and compositions for cancer, for example, bladder cancer (e.g., urothelial bladder cancer, UBC). The invention is based, at least in part, on the discovery that determination of expression levels of biomarkers of the invention, for example, PD-L1 and/or tumor subtype, in samples obtained from a patient is useful in treatment of a patient suffering from cancer, for diagnosing a patient suffering from cancer, for determining whether a patient having a cancer is likely to respond to treatment with an anti-cancer therapy that includes a PD-L1 axis binding antagonist (e.g., an anti-PD-L1 antibody, e.g., atezolizumab (MPDL3280A)), for optimizing therapeutic efficacy of an anti-cancer therapy that includes a PD-L1 axis binding antagonist (e.g., an anti-PD-L1 antibody, e.g., atezolizumab), and/or for patient selection for an anti-cancer therapy comprising a PD-L1 axis binding antagonist (e.g., an anti-PD-L1 antibody, e.g., atezolizumab).

II. Definitions

It is to be understood that aspects and embodiments of the invention described herein include "comprising," "consisting," and "consisting essentially of" aspects and embodiments. As used herein, the singular form "a," "an," and "the" includes plural references unless indicated otherwise.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X."

The terms "tumor subtype" or "tumor sample subtype" refers to the intrinsic molecular characteristics (e.g., DNA, RNA, and/or protein expression levels (e.g., genomic profile)) of a tumor or cancer. The particular subtype of a tumor or cancer (e.g., a urothelial bladder cancer (UBC tumor)) can be determined by histopathological criteria or subtype-associated molecular features (e.g., expression of one or biomarkers (e.g., particular genes, RNA (e.g., mRNA, microRNA), or proteins encoded by said genes)) (see, e.g., Cancer Genome Atlas Research Network Nature 507:315-22, 2014; Jiang et al. Bioinformatics 23:306-13, 2007; Dong et al. Nat. Med. 8:793-800, 2002).

The term "PD-L1 axis binding antagonist" refers to a molecule that inhibits the interaction of a PD-L1 axis binding partner with one or more of its binding partners, so as to remove T-cell dysfunction resulting from signaling on the PD-1 signaling axis, with a result being restored or enhanced T-cell function. As used herein, a PD-L1 axis binding antagonist includes a PD-L1 binding antagonist and a PD-1 binding antagonist as well as molecules that interfere with the interaction between PD-L1 and PD-1 (e.g., a PD-L2-Fc fusion).

The term "dysfunction," in the context of immune dysfunction, refers to a state of reduced immune responsiveness to antigenic stimulation. The term includes the common elements of both "exhaustion" and/or "anergy" in which antigen recognition may occur, but the ensuing immune response is ineffective to control infection or tumor growth. The term "dysfunctional," as used herein, also includes refractory or unresponsive to antigen recognition, specifically, impaired capacity to translate antigen recognition into down-stream T-cell effector functions, such as proliferation, cytokine production (e.g., IL-2) and/or target cell killing.

The term "anergy" refers to the state of unresponsiveness to antigen stimulation resulting from incomplete or insufficient signals delivered through the T-cell receptor (e.g., increase in intracellular $Ca^{2+}$ in the absence of Ras activation). T-cell anergy can also result upon stimulation with antigen in the absence of co-stimulation, resulting in the cell becoming refractory to subsequent activation by the antigen even in the context of co-stimulation. The unresponsive state can often be overridden by the presence of interleukin-2. Anergic T-cells do not undergo clonal expansion and/or acquire effector functions.

The term "exhaustion" refers to T-cell exhaustion as a state of T-cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T-cells. Exhaustion prevents optimal control of infection and tumors. Exhaustion can result from both extrinsic negative regulatory pathways (e.g., immunoregulatory cytokines) as well as cell-intrinsic negative regulatory (co-stimulatory) pathways (PD-1, B7-H3, B7-H4, etc.).

"Enhancing T-cell function" means to induce, cause or stimulate a T-cell to have a sustained or amplified biological function, or renew or reactivate exhausted or inactive T-cells. Examples of enhancing T-cell function include: increased secretion of y-interferon from CD8+ T-cells, increased proliferation, increased antigen responsiveness (e.g., viral, pathogen, or tumor clearance) relative to such levels before the intervention. In one embodiment, the level of enhancement is at least 50%, alternatively 60%, 70%, 80%, 90%, 100%, 120%, 150%, or 200% enhancement. The manner of measuring this enhancement is known to one of ordinary skill in the art.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

"Immunogenicity" refers to the ability of a particular substance to provoke an immune response. Tumors are immunogenic and enhancing tumor immunogenicity aids in the clearance of the tumor cells by the immune response. Examples of enhancing tumor immunogenicity include treatment with a PD-L1 axis binding antagonist.

As used herein, a "PD-L1 binding antagonist" is a molecule that decreases, blocks, inhibits, abrogates or interferes with signal transduction resulting from the interaction of PD-L1 with either one or more of its binding partners, such as PD-1 and/or B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, PD-L1 binding antagonists include anti-PD-L1 antibodies and antigen-binding fragments thereof, immunoadhesins, fusion proteins, oligopeptides, small molecule antagonists, polynucleotide antagonists, and other molecules that decrease, block, inhibit, abrogate or interfere with signal transduction resulting from the interaction of PD-L1 with one or more of its binding partners, such as PD-1 and/or B7-1. In one embodiment, a PD-L1 binding antagonist reduces the negative signal mediated by or through cell surface proteins expressed on T lymphocytes and other cells through PD-L1 or PD-1 so as to render a dysfunctional T-cell less dysfunctional. In some embodiments, a PD-L1 binding antagonist is an anti-PD-L1 antibody. In a specific aspect, an anti-PD-L1 antibody is YW243.55.S70 described herein. In another specific aspect, an anti-PD-L1 antibody is MDX-1105 described herein. In still another specific aspect, an anti-PD-L1 antibody is atezolizumab (MPDL3280A) described herein. In still another specific aspect, an anti-PD-L1 antibody is MED14736 (druvalumab) described herein. In still another specific aspect, an anti-PD-L1 antibody is MSB0010718C (avelumab) described herein.

As used herein, a "PD-1 binding antagonist" is a molecule that decreases, blocks, inhibits, abrogates or interferes with signal transduction resulting from the interaction of PD-1 with one or more of its binding partners, such as PD-L1 and/or PD-L2. In some embodiments, the PD-1 binding antagonist is a molecule that inhibits the binding of PD-1 to its binding partners. In a specific aspect, the PD-1 binding antagonist inhibits the binding of PD-1 to PD-L1 and/or PD-L2. For example, PD-1 binding antagonists include anti-PD-1 antibodies and antigen-binding fragments thereof, immunoadhesins, fusion proteins, oligopeptides, small molecule antagonists, polynucleotide antagonists, and other molecules that decrease, block, inhibit, abrogate or interfere with signal transduction resulting from the interaction of PD-1 with PD-L1 and/or PD-L2. In one embodiment, a PD-1 binding antagonist reduces the negative signal mediated by or through cell surface proteins expressed on T lymphocytes and other cells through PD-1 or PD-L1 so as to render a dysfunctional T-cell less dysfunctional. In some embodiments, the PD-1 binding antagonist is an anti-PD-1 antibody. In a specific aspect, a PD-1 binding antagonist is MDX-1106 (nivolumab) described herein. In another specific aspect, a PD-1 binding antagonist is MK-3475 (pembrolizumab) described herein. In another specific aspect, a PD-1 binding antagonist is CT-011 (pidilizumab) described herein. In another specific aspect, a PD-1 binding antagonist is MEDI-0680 (AMP-514) described herein. In another specific aspect, a PD-1 binding antagonist is PDR001 described herein. In another specific aspect, a PD-1 binding antagonist is REGN2810 described herein. In another specific aspect, a PD-1 binding antagonist is BGB-108 described herein. In another specific aspect, a PD-1 binding antagonist is AMP-224 described herein.

The terms "Programmed Death Ligand 1" and "PD-L1" refer herein to a native sequence PD-L1 polypeptide, polypeptide variants, and fragments of a native sequence polypeptide and polypeptide variants (which are further defined herein). The PD-L1 polypeptide described herein may be that which is isolated from a variety of sources, such as from human tissue types or from another source, or prepared by recombinant or synthetic methods.

A "native sequence PD-L1 polypeptide" comprises a polypeptide having the same amino acid sequence as the corresponding PD-L1 polypeptide derived from nature.

A "PD-L1 polypeptide variant," or variations thereof, means a PD-L1 polypeptide, generally an active PD-L1 polypeptide, as defined herein having at least about 80% amino acid sequence identity with any of the native sequence PD-L1 polypeptide sequences as disclosed herein. Such PD-L1 polypeptide variants include, for instance, PD-L1 polypeptides wherein one or more amino acid residues are added, or deleted, at the N- or C-terminus of a native amino acid sequence. Ordinarily, a PD-L1 polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a native sequence PD-L1 polypeptide sequence as disclosed herein. Ordinarily, PD-L1 variant polypeptides are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 281, 282, 283, 284, 285, 286, 287, 288, or 289 amino acids in length, or more. Optionally, PD-L1 variant polypeptides will have no more than one conservative amino acid substitution as compared to a native PD-L1 polypeptide sequence, alternatively no more than 2, 3, 4, 5, 6, 7, 8, 9, or 10 conservative amino acid substitutions as compared to a native PD-L1 polypeptide sequence.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs.

A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally-occurring nucleotides with an analog, internucleotide modifications such as, for example, those with uncharged linkages (e.g., methyl phosphonates, phosphotriesters, phosphoamidates, carbamates, and the like) and with charged linkages (e.g., phosphorothioates, phosphorodithioates, and the like), those containing pendant moieties, such as, for example, proteins (e.g., nucleases, toxins, antibodies, signal peptides, poly-L-lysine, and the like), those with intercalators (e.g., acridine, psoralen, and the like), those containing chelators (e.g., metals, radioactive metals, boron, oxidative metals, and the like), those containing alkylators, those with modified linkages (e.g., alpha anomeric nucleic acids), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro-, or 2'-azido-ribose, carbocyclic sugar analogs, a-anomeric sugars, epimeric sugars such as arabinose, xyloses or lyxoses, pyranose sugars, furanose sugars, sedoheptuloses, acyclic analogs, and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. A polynucleotide can contain one or more different types of modifications as described herein and/or multiple modifications of the same type. The preceding description applies to all polynucleotides referred to herein, including RNA and DNA.

"Oligonucleotide," as used herein, generally refers to short, single stranded, polynucleotides that are, but not necessarily, less than about 250 nucleotides in length. Oligonucleotides may be synthetic. The terms "oligonucleotide" and "polynucleotide" are not mutually exclusive. The description above for polynucleotides is equally and fully applicable to oligonucleotides.

The term "primer" refers to a single-stranded polynucleotide that is capable of hybridizing to a nucleic acid and allowing polymerization of a complementary nucleic acid, generally by providing a free 3'—OH group.

The term "small molecule" refers to any molecule with a molecular weight of about 2000 daltons or less, preferably of about 500 daltons or less.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "isolated" antibody is one which has been identified and separated and/or recovered from a component of its natural environment. Contaminant components of its natural environment are materials which would interfere with research, diagnostic, and/or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. An isolated antibody includes the antibody in situ within recombinant cells since at least one component of the antibody's natural environment will not be present. Ordinarily, however, an isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The "light chains" of antibodies (immunoglobulins) from any mammalian species can be assigned to one of two clearly distinct types, called kappa ("κ") and lambda ("λ"), based on the amino acid sequences of their constant domains.

The term "constant domain" refers to the portion of an immunoglobulin molecule having a more conserved amino acid sequence relative to the other portion of the immunoglobulin, the variable domain, which contains the antigen binding site. The constant domain contains the CH1, CH2, and CH3 domains (collectively, CH) of the heavy chain and the CHL (or CL) domain of the light chain.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The term "hypervariable region," "HVR," or "HV," as used herein, refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, for example, Xu et al., *Immunity* 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, for example, Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact | |
|------|-------|-----|---------|---------|---|
| L1 | L24-L34 | L24-L34 | L26-L32 | L30-L36 | |
| L2 | L50-L56 | L50-L52 | L46-L55 | | |
| L3 | L89-L97 | L89-L97 | L91-L96 | L89-L96 | |
| H1 | H31-H35b | H26-H35b | H26-H32 | H30-H35b | (Kabat Numbering) |
| H1 | H31-H35 | H26-H35 | H26-H32 | H30-H35 | (Chothia Numbering) |
| H2 | H50-H65 | H50-H58 | H53-H55 | H47-H58 | |
| H3 | H95-H102 | H95-H102 | H96-H101 | H93-H101 | |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH.

The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g., residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

The terms "full-length antibody," "intact antibody," and "whole antibody" are used herein interchangeably to refer to an antibody in its substantially intact form, not antibody fragments as defined below. The terms particularly refer to an antibody with heavy chains that contain an Fc region.

"Antibody fragments" comprise a portion of an intact antibody, preferably comprising the antigen-binding region thereof. In some embodiments, the antibody fragment described herein is an antigen-binding fragment. Examples of antibody fragments include Fab, Fab', F(ab')$_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH$_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies, vol.* 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., Nat. Med. 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of antibodies are called $\alpha$, $\beta$, $\varepsilon$, $\gamma$, and $\mu$, respectively.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target-binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target-binding sequence can be further altered, for example, to improve affinity for the target, to humanize the target-binding sequence, to improve its production in cell culture, to reduce its immunogenicity in vivo, to create a multispecific antibody, etc., and that an antibody comprising the altered target-binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by a variety of techniques, including, for example, the hybridoma method (e.g., Kohler and Milstein, Nature 256:495-97 (1975); Hongo et al., *Hybridoma* 14 (3): 253-260 (1995), Harlow et al., *Antibodies: A Laboratory Manual* (Cold Spring Harbor Laboratory Press, 2nd ed. 1988); Hammerling et al., in: *MonoclonalAntibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004)), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., Nature 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg et al., *Intern. Rev. Immunol.* 13: 65-93 (1995)).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., Proc. Natl. Acad. Sci. USA 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human framework regions (FRs). In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The terms "anti-PD-L1 antibody" and "an antibody that binds to PD-L1" refer to an antibody that is capable of binding PD-L1 with sufficient affinity such that the antibody is useful as a diagnostic and/or therapeutic agent in targeting PD-L1. In one embodiment, the extent of binding of an anti-PD-L1 antibody to an unrelated, non-PD-L1 protein is less than about 10% of the binding of the antibody to PD-L1 as measured, for example, by a radioimmunoassay (RIA). In certain embodiments, an anti-PD-L1 antibody binds to an epitope of PD-L1 that is conserved among PD-L1 from different species.

The terms "anti-PD-1 antibody" and "an antibody that binds to PD-1" refer to an antibody that is capable of binding PD-1 with sufficient affinity such that the antibody is useful as a diagnostic and/or therapeutic agent in targeting PD-1. In one embodiment, the extent of binding of an anti-PD-1 antibody to an unrelated, non-PD-1 protein is less than about 10% of the binding of the antibody to PD-1 as measured, for example, by a radioimmunoassay (RIA). In certain embodiments, an anti-PD-1 antibody binds to an epitope of PD-1 that is conserved among PD-1 from different species.

A "blocking" antibody or an "antagonist" antibody is one which inhibits or reduces biological activity of the antigen it binds. Preferred blocking antibodies or antagonist antibodies substantially or completely inhibit the biological activity of the antigen.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

As used herein, the term "binds", "specifically binds to" or is "specific for" refers to measurable and reproducible interactions such as binding between a target and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 µM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more.

An "immunoconjugate" is an antibody conjugated to one or more heterologous molecule(s), including but not limited to a cytotoxic agent.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG1, IgG2 (including IgG2A and IgG2B), IgG3, or IgG4 subtypes, IgA (including IgA1 and IgA2), IgE, IgD or IgM. The Ig fusions preferably include the substitution of a domain of a polypeptide or antibody described herein in the place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130. For example, useful immunoadhesins as medicaments useful for therapy herein include polypeptides that comprise the extracellular domain (ECD) or PD-1-binding portions of PD-L1 or PD-L2, or the extracellular or PD-L1- or PD-L2-binding portions of PD-1, fused to a constant domain of an immunoglobulin sequence, such as a PD-L1 ECD-Fc, a PD-L2 ECD-Fc, and a PD-1 ECD-Fc, respectively.

Immunoadhesin combinations of Ig Fc and ECD of cell surface receptors are sometimes termed soluble receptors.

A "fusion protein" and a "fusion polypeptide" refer to a polypeptide having two portions covalently linked together, where each of the portions is a polypeptide having a different property. The property may be a biological property, such as activity in vitro or in vivo. The property may also be a simple chemical or physical property, such as binding to a target molecule, catalysis of a reaction, and the like. The two portions may be linked directly by a single peptide bond or through a peptide linker but are in reading frame with each other.

"Percent (%) amino acid sequence identity" with respect to the polypeptide sequences identified herein is defined as the percentage of amino acid residues in a candidate sequence that are identical with the amino acid residues in the polypeptide being compared, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "detection" includes any means of detecting, including direct and indirect detection.

The term "biomarker" as used herein refers to an indicator, e.g., predictive, diagnostic, and/or prognostic, which can be detected in a sample, for example, PD-L1, FGFR3, miR-99a-5p, miR-100-5p, CDKN2A, KRT5, KRT6A, KRT14, EGFR, GATA3, FOXA1, UPK3A, miR-200a-3p, miR-200b-3p, E-cadhherin, ERBB2, or ESR2. The biomarker may serve as an indicator of a particular subtype of a disease or disorder (e.g., cancer) characterized by certain, molecular, pathological, histological, and/or clinical features. In some embodiments, a biomarker is a gene. Biomarkers include, but are not limited to, polynucleotides (e.g., DNA and/or RNA), polynucleotide copy number alterations (e.g., DNA copy numbers), polypeptides, polypeptide and polynucleotide modifications (e.g., post-translational modifications), carbohydrates, and/or glycolipid-based molecular markers.

The "amount" or "level" of a biomarker associated with an increased clinical benefit to an individual is a detectable level in a biological sample. These can be measured by methods known to one skilled in the art and also disclosed herein. The expression level or amount of biomarker assessed can be used to determine the response to the treatment.

The terms "level of expression" or "expression level" in general are used interchangeably and generally refer to the amount of a biomarker in a biological sample. "Expression" generally refers to the process by which information (e.g., gene-encoded and/or epigenetic information) is converted into the structures present and operating in the cell. Therefore, as used herein, "expression" may refer to transcription into a polynucleotide, translation into a polypeptide, or even polynucleotide and/or polypeptide modifications (e.g., post-translational modification of a polypeptide). Fragments of the transcribed polynucleotide, the translated polypeptide, or polynucleotide and/or polypeptide modifications (e.g., post-translational modification of a polypeptide) shall also be regarded as expressed whether they originate from a transcript generated by alternative splicing or a degraded transcript, or from a post-translational processing of the polypeptide, e.g., by proteolysis. "Expressed genes" include those that are transcribed into a polynucleotide as mRNA and then translated into a polypeptide, and also those that are transcribed into RNA but not translated into a polypeptide (for example, transfer and ribosomal RNAs).

"Increased expression," "increased expression level," "increased levels," "elevated expression," "elevated expression levels," or "elevated levels" refers to an increased expression or increased levels of a biomarker in an individual relative to a control, such as an individual or individuals who are not suffering from the disease or disorder (e.g., cancer) or an internal control (e.g., a housekeeping biomarker).

"Decreased expression," "decreased expression level," "decreased levels," "reduced expression," "reduced expression levels," or "reduced levels" refers to a decrease expression or decreased levels of a biomarker in an individual relative to a control, such as an individual or individuals who are not suffering from the disease or disorder (e.g., cancer) or an internal control (e.g., a housekeeping biomarker). In some embodiments, reduced expression is little or no expression.

The term "housekeeping biomarker" refers to a biomarker or group of biomarkers (e.g., polynucleotides and/or polypeptides) which are typically similarly present in all cell types. In some embodiments, the housekeeping biomarker is a "housekeeping gene." A "housekeeping gene" refers herein to a gene or group of genes which encode proteins whose activities are essential for the maintenance of cell function and which are typically similarly present in all cell types.

"Amplification," as used herein generally refers to the process of producing multiple copies of a desired sequence. "Multiple copies" mean at least two copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

The term "multiplex-PCR" refers to a single PCR reaction carried out on nucleic acid obtained from a single source (e.g., an individual) using more than one primer set for the purpose of amplifying two or more DNA sequences in a single reaction.

The technique of "polymerase chain reaction" or "PCR" as used herein generally refers to a procedure wherein minute amounts of a specific piece of nucleic acid, RNA and/or DNA, are amplified as described, for example, in U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage, or plasmid sequences, etc. See generally Mullis et al., *Cold Spring Harbor Symp. Quant. Biol.* 51:263 (1987) and Erlich, ed., *PCR Technology*, (Stockton Press, N Y, 1989). As used herein, PCR is considered to be one, but not the only, example of a nucleic acid polymerase reaction method for amplifying a nucleic acid test sample, comprising the use of a known nucleic acid (DNA or RNA) as a primer and utilizes a nucleic acid polymerase to amplify or generate a specific piece of nucleic acid or to amplify or generate a specific piece of nucleic acid which is complementary to a particular nucleic acid.

"Quantitative real-time polymerase chain reaction" or "qRT-PCR" refers to a form of PCR wherein the amount of PCR product is measured at each step in a PCR reaction. This technique has been described in various publications including, for example, Cronin et al., *Am. J. Pathol.* 164(1): 35-42 (2004) and Ma et al., *Cancer Cell* 5:607-616 (2004).

The term "microarray" refers to an ordered arrangement of hybridizable array elements, preferably polynucleotide probes, on a substrate.

The term "diagnosis" is used herein to refer to the identification or classification of a molecular or pathological state, disease or condition (e.g., cancer). For example, "diagnosis" may refer to identification of a particular type of cancer. "Diagnosis" may also refer to the classification of a particular subtype of cancer, for instance, by histopathological criteria, or by molecular features (e.g., a subtype characterized by expression of one or a combination of biomarkers (e.g., particular genes or proteins encoded by said genes)).

The term "aiding diagnosis" is used herein to refer to methods that assist in making a clinical determination regarding the presence, or nature, of a particular type of symptom or condition of a disease or disorder (e.g., cancer). For example, a method of aiding diagnosis of a disease or condition (e.g., cancer) can comprise measuring certain biomarkers (e.g., PD-L1) in a biological sample from an individual.

The term "sample," as used herein, refers to a composition that is obtained or derived from a subject and/or individual of interest that contains a cellular and/or other molecular entity that is to be characterized and/or identified, for example, based on physical, biochemical, chemical, and/or physiological characteristics.

For example, the phrase "disease sample" and variations thereof refers to any sample obtained from a subject of interest that would be expected or is known to contain the cellular and/or molecular entity that is to be characterized. Samples include, but are not limited to, tissue samples, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebro-spinal fluid, saliva, sputum, tears, perspiration, mucus, tumor lysates, and tissue culture medium, tissue extracts such as homogenized tissue, tumor tissue, cellular extracts, and combinations thereof.

By "tissue sample" or "cell sample" is meant a collection of similar cells obtained from a tissue of a subject or individual. The source of the tissue or cell sample may be solid tissue as from a fresh, frozen and/or preserved organ, tissue sample, biopsy, and/or aspirate; blood or any blood constituents such as plasma; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. For instance, a "tumor sample" is a tissue sample obtained from a tumor or other cancerous tissue. The tissue sample may contain a mixed population of cell types (e.g., tumor cells and non-tumor cells, cancerous cells and non-cancerous cells). The tissue sample may contain compounds which are not naturally intermixed with the tissue in nature such as preservatives, anticoagulants, buffers, fixatives, nutrients, antibiotics, or the like.

A "tumor-infiltrating immune cell," as used herein, refers to any immune cell present in a tumor or a sample thereof. Tumor-infiltrating immune cells include, but are not limited to, intratumoral immune cells, peritumoral immune cells, other tumor stroma cells (e.g., fibroblasts), or any combination thereof. Such tumor-infiltrating immune cells can be, for example, T lymphocytes (such as CD8+T lymphocytes and/or CD4+T lymphocytes), B lymphocytes, or other bone marrow-lineage cells, including granulocytes (e.g., neutrophils, eosinophils, and basophils), monocytes, macrophages, dendritic cells (e.g., interdigitating dendritic cells), histiocytes, and natural killer cells.

A "tumor cell" as used herein, refers to any tumor cell present in a tumor or a sample thereof. Tumor cells may be distinguished from other cells that may be present in a tumor sample, for example, stromal cells and tumor-infiltrating immune cells, using methods known in the art and/or described herein.

A "reference sample," "reference cell," "reference tissue," "control sample," "control cell," or "control tissue," as used herein, refers to a sample, cell, tissue, standard, or level that is used for comparison purposes. In one embodiment, a reference sample, reference cell, reference tissue, control sample, control cell, or control tissue is obtained from a healthy and/or non-diseased part of the body (e.g., tissue or cells) of the same subject or individual. For example, the reference sample, reference cell, reference tissue, control sample, control cell, or control tissue may be healthy and/or non-diseased cells or tissue adjacent to the diseased cells or tissue (e.g., cells or tissue adjacent to a tumor). In another embodiment, a reference sample is obtained from an untreated tissue and/or cell of the body of the same subject or individual. In yet another embodiment, a reference sample, reference cell, reference tissue, control sample, control cell, or control tissue is obtained from a healthy and/or non-diseased part of the body (e.g., tissues or cells) of an individual who is not the subject or individual. In even another embodiment, a reference sample, reference cell, reference tissue, control sample, control cell, or control tissue is obtained from an untreated tissue and/or cell of the body of an individual who is not the subject or individual.

For the purposes herein a "section" of a tissue sample is meant a single part or piece of a tissue sample, for example, a thin slice of tissue or cells cut from a tissue sample (e.g., a tumor sample). It is to be understood that multiple sections of tissue samples may be taken and subjected to analysis, provided that it is understood that the same section of tissue sample may be analyzed at both morphological and molecular levels, or analyzed with respect to polypeptides (e.g., by immunohistochemistry) and/or polynucleotides (e.g., by in situ hybridization).

By "correlate" or "correlating" is meant comparing, in any way, the performance and/or results of a first analysis or protocol with the performance and/or results of a second analysis or protocol. For example, one may use the results of a first analysis or protocol in carrying out a second protocol and/or one may use the results of a first analysis or protocol to determine whether a second analysis or protocol should be performed. With respect to the embodiment of polypeptide analysis or protocol, one may use the results of the polypeptide expression analysis or protocol to determine whether a specific therapeutic regimen should be performed. With respect to the embodiment of polynucleotide analysis or protocol, one may use the results of the polynucleotide expression analysis or protocol to determine whether a specific therapeutic regimen should be performed.

"Individual response" or "response" can be assessed using any endpoint indicating a benefit to the individual, including, without limitation, (1) inhibition, to some extent, of disease progression (e.g., cancer progression), including slowing down or complete arrest; (2) a reduction in tumor size; (3) inhibition (i.e., reduction, slowing down, or complete stopping) of cancer cell infiltration into adjacent peripheral organs and/or tissues; (4) inhibition (i.e. reduction, slowing down, or complete stopping) of metastasis; (5) relief, to some extent, of one or more symptoms associated with the disease or disorder (e.g., cancer); (6) increase or extension in the length of survival, including overall survival, including overall survival and progression free survival; and/or (7) decreased mortality at a given point of time following treatment.

An "effective response" of a patient or a patient's "responsiveness" to treatment with a medicament and similar wording refers to the clinical or therapeutic benefit imparted to a patient at risk for, or suffering from, a disease or disorder, such as cancer. In one embodiment, such benefit includes any one or more of: extending survival (including overall survival and/or progression-free survival); resulting in an objective response (including a complete response or a partial response); or improving signs or symptoms of cancer.

In one embodiment, the biomarker (e.g., PD-L1 expression in tumor-infiltrating immune cells, for example, as determined using IHC) is used to identify the patient who is predicted to have an increased likelihood of being responsive to treatment with a medicament (e.g., treatment comprising a PD-L1 axis binding antagonist, e.g., an anti-PD-L1 antibody), relative to a patient who does not express the biomarker. In one embodiment, the biomarker (e.g., PD-L1 expression expression in tumor-infiltrating immune cells, for example, as determined using IHC) is used to identify the patient who is predicted to have an increase likelihood of being responsive to treatment with a medicament (e.g., anti-PD-L1 antibody), relative to a patient who does not express the biomarker at the same level. In one embodiment, the presence of the biomarker is used to identify a patient who is more likely to respond to treatment with a medicament, relative to a patient that does not have the presence of the biomarker. In another embodiment, the presence of the biomarker is used to determine that a patient will have an increased likelihood of benefit from treatment with a medicament, relative to a patient that does not have the presence of the biomarker.

An "objective response" refers to a measurable response, including complete response (CR) or partial response (PR). In some embodiments, the "objective response rate (ORR)" refers to the sum of complete response (CR) rate and partial response (PR) rate.

By "complete response" or "CR" is intended the disappearance of all signs of cancer (e.g., disappearance of all target lesions) in response to treatment. This does not always mean the cancer has been cured.

"Sustained response" refers to the sustained effect on reducing tumor growth after cessation of a treatment. For example, the tumor size may be the same size or smaller as compared to the size at the beginning of the medicament administration phase. In some embodiments, the sustained response has a duration at least the same as the treatment duration, at least 1.5×, 2.0×, 2.5×, or 3.0× length of the treatment duration, or longer.

As used herein, "reducing or inhibiting cancer relapse" means to reduce or inhibit tumor or cancer relapse or tumor or cancer progression. As disclosed herein, cancer relapse and/or cancer progression include, without limitation, cancer metastasis.

As used herein, "partial response" or "PR" refers to a decrease in the size of one or more tumors or lesions, or in the extent of cancer in the body, in response to treatment. For example, in some embodiments, PR refers to at least a 30% decrease in the sum of the longest diameters (SLD) of target lesions, taking as reference the baseline SLD.

As used herein, "stable disease" or "SD" refers to neither sufficient shrinkage of target lesions to qualify for PR, nor sufficient increase to qualify for PD, taking as reference the smallest SLD since the treatment started.

As used herein, "progressive disease" or "PD" refers to at least a 20% increase in the SLD of target lesions, taking as reference the smallest SLD recorded since the treatment started or the presence of one or more new lesions.

The term "survival" refers to the patient remaining alive, and includes overall survival as well as progression-free survival As used herein, "progression-free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall survival" (OS) refers to the percentage of individuals in a group who are likely to be alive after a particular duration of time.

By "extending survival" is meant increasing overall or progression-free survival in a treated patient relative to an untreated patient (i.e. relative to a patient not treated with the medicament), or relative to a patient who does not express a biomarker at the designated level, and/or relative to a patient treated with an anti-tumor agent.

The term "substantially the same," as used herein, denotes a sufficiently high degree of similarity between two numeric values, such that one of skill in the art would consider the difference between the two values to be of little or no biological and/or statistical significance within the context of the biological characteristic measured by said values (e.g., Kd values or expression levels). The difference between said two values is, for example, less than about 50%, less than about 40%, less than about 30%, less than about 20%, and/or less than about 10%, as a function of the reference/comparator value.

The phrase "substantially different," as used herein, denotes a sufficiently high degree of difference between two numeric values such that one of skill in the art would consider the difference between the two values to be of statistical significance within the context of the biological characteristic measured by said values (e.g., Kd values or expression levels). The difference between said two values is, for example, greater than about 10%, greater than about 20%, greater than about 30%, greater than about 40%, and/or greater than about 50%, as a function of the value for the reference/comparator molecule.

The word "label" when used herein refers to a compound or composition that is conjugated or fused directly or indirectly to a reagent such as a polynucleotide probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable. The term is intended to encompass direct labeling of a probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin.

A "therapeutically effective amount" refers to an amount of a therapeutic agent to treat or prevent a disease or disorder in a mammal. In the case of cancers, the therapeutically effective amount of the therapeutic agent may reduce the number of cancer cells; reduce the primary tumor size;

inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), response rates (e.g., CR and PR), duration of response, and/or quality of life.

A "disorder" is any condition that would benefit from treatment including, but not limited to, chronic and acute disorders or diseases including those pathological conditions which predispose the mammal to the disorder in question.

The terms "cancer" and "cancerous" refer to or describe the physiological condition in mammals that is typically characterized by unregulated cell growth. Included in this definition are benign and malignant cancers. By "early stage cancer" or "early stage tumor" is meant a cancer that is not invasive or metastatic or is classified as a Stage 0, 1, or 2 cancer. Examples of cancer include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include bladder cancer (e.g., urothelial bladder cancer (e.g., transitional cell or urothelial carcinoma, non-muscle invasive bladder cancer, muscle-invasive bladder cancer, and metastatic bladder cancer) and non-urothelial bladder cancer), squamous cell cancer (e.g., epithelial squamous cell cancer), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, Merkel cell cancer, mycoses fungoids, testicular cancer, esophageal cancer, tumors of the biliary tract, as well as head and neck cancer and hematological malignancies. In some embodiments, the cancer is triple-negative metastatic breast cancer, including any histologically confirmed triple-negative (ER−, PR−, HER2−) adenocarcinoma of the breast with locally recurrent or metastatic disease (where the locally recurrent disease is not amenable to resection with curative intent). In some embodiments, the cancer is bladder cancer. In particular embodiments, the bladder cancer is urothelial bladder cancer.

The term "tumor," as used herein, refers to all neoplastic cell growth and proliferation, whether malignant or benign, and all pre-cancerous and cancerous cells and tissues. The terms "cancer," "cancerous," and "tumor" are not mutually exclusive as referred to herein.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies (e.g., anti-PD-L1 antibodies and/or anti-PD-1 antibodies) are used to delay development of a disease or to slow the progression of a disease.

The term "anti-cancer therapy" refers to a therapy useful in treating cancer. Examples of anti-cancer therapeutic agents include, but are limited to, cytotoxic agents, chemotherapeutic agents, growth inhibitory agents, agents used in radiation therapy, anti-angiogenesis agents, apoptotic agents, anti-tubulin agents, and other agents to treat cancer, for example, anti-CD20 antibodies, platelet derived growth factor inhibitors (e.g., GLEEVEC™ (imatinib mesylate)), a COX-2 inhibitor (e.g., celecoxib), interferons, cytokines, antagonists (e.g., neutralizing antibodies) that bind to one or more of the following targets PDGFR-β, BlyS, APRIL, BCMA receptor(s), TRAIL/Apo2, other bioactive and organic chemical agents, and the like. Combinations thereof are also included in the invention.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents, e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (see, e.g., Nicolaou et al., Angew. Chem Intl. Ed. Engl., 33: 183-186 (1994)); dynemicin, including dynemicin A; an esperamicin; as well as neocarzinostatin chromophore and related chromoprotein enediyne antibiotic chromophores, aclacinomysins, actinomycin, authramycin, azaserine, bleomycins, cactinomycin, carabicin, carminomycin, carzinophilin, chromomycin, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, for example taxanes including TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® docetaxel (Rhône-Poulenc Rorer, Antony, France); chloranbucil; gemcitabine (GEMZAR®); 6-thioguanine; mercaptopurine; methotrexate; platinum or platinum-based chemotherapy agents and platinum analogs, such as cisplatin, carboplatin, oxaliplatin (ELOXATIN™), satraplatin, picoplatin, nedaplatin, triplatin, and lipoplatin; vinblastine (VELBAN®); platinum; etoposide (VP-16); ifosfamide; mitoxantrone; vincristine (ONCOVIN®); oxaliplatin; leucovorin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin. Additional chemotherapeutic agents include the cytotoxic agents useful as antibody drug conjugates, such as maytansinoids (DM1, for example) and the auristatins MMAE and MMAF, for example.

"Chemotherapeutic agents" also include "anti-hormonal agents" or "endocrine therapeutics" that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGFR); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

Chemotherapeutic agents also include antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG1λ antibody genetically modified to recognize interleukin-12 p40 protein.

Chemotherapeutic agents also include "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3, and E7.6. 3 and described in U.S. Pat. No. 6,235,883; MDX-447 (Medarex Inc); and mAb 806 or humanized mAb 806 (Johns et al., J. Biol. Chem. 279(29): 30375-30384 (2004)). The anti-EGFR antibody may be conjugated with a cytotoxic agent, thus generating an immunoconjugate (see, e.g., EP 659,439A2, Merck Patent GmbH). EGFR antagonists include small molecules such as compounds described in U.S. Pat. Nos. 5,616,582, 5,457, 105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO 98/14451, WO 98/50038, WO 99/09016, and WO 99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenylamino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); and dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl)ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitors such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from GlaxoSmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g., those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (ENBREL®), infliximab (REMICADE®), adalimumab (HUMIRA®), certolizumab pegol (CIMZIA®), golimumab (SIMPONI®), Interleukin 1 (IL-1) blockers such as anakinra (KINERET®), T-cell co-stimulation blockers such as abatacept (ORENCIA®), Interleukin 6 (IL-6) blockers such as tocilizumab (ACTEMERA®); Interleukin 13 (IL-13) blockers such as lebrikizumab; Interferon alpha (IFN) blockers such as rontalizumab; beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); miscellaneous investigational agents such as thioplatin, PS-341, phenylbutyrate, ET-18-OCH3, and farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g., celecoxib or etoricoxib), proteosome inhibitor (e.g., PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above.

The term "prodrug" as used herein refers to a precursor or derivative form of a pharmaceutically active substance that is less cytotoxic to tumor cells compared to the parent drug and is capable of being enzymatically activated or converted into the more active parent form. See, for example, Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "growth inhibitory agent" when used herein refers to a compound or composition which inhibits growth and/or proliferation of a cell (e.g., a cell whose growth is dependent on PD-L1 expression) either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as the anthracycline antibiotic doxorubicin ((8S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5, 12-naphthacenedione), epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in "The Molecular Basis of Cancer," Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

As used herein, the terms "patient" or "subject" are used interchangeably and refer to any single animal, more preferably a mammal (including such non-human animals as, for example, dogs, cats, horses, rabbits, zoo animals, cows, pigs, sheep, and non-human primates) for which treatment is desired. In particular embodiments, the patient herein is a human.

As used herein, "administering" is meant a method of giving a dosage of a compound (e.g., an antagonist) or a pharmaceutical composition (e.g., a pharmaceutical composition including an antagonist) to a subject (e.g., a patient). Administering can be by any suitable means, including parenteral, intrapulmonary, and intranasal, and, if desired for local treatment, intralesional administration. Parenteral infusions include, for example, intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent (s).

By "reduce or inhibit" is meant the ability to cause an overall decrease of 20%, 30%, 40%, 50%, 60%, 70%, 75%, 80%, 85%, 90%, 95%, or greater. Reduce or inhibit can refer, for example, to the symptoms of the disorder being treated, the presence or size of metastases, or the size of the primary tumor.

The term "package insert" is used to refer to instructions customarily included in commercial packages of therapeutic products, that contain information about the indications, usage, dosage, administration, combination therapy, contraindications, and/or warnings concerning the use of such therapeutic products.

A "sterile" formulation is aseptic or free from all living microorganisms and their spores.

An "article of manufacture" is any manufacture (e.g., a package or container) or kit comprising at least one reagent, e.g., a medicament for treatment of a disease or disorder (e.g., cancer), or a probe for specifically detecting a biomarker (e.g., PD-L1) described herein. In certain embodiments, the manufacture or kit is promoted, distributed, or sold as a unit for performing the methods described herein.

The phrase "based on" when used herein means that the information about one or more biomarkers is used to inform a treatment decision, information provided on a package insert, or marketing/promotional guidance, etc.

III. Methods

A. Diagnostic Methods Based on the Expression Level of PD-L1

Provided herein are methods for determining whether a patient suffering from a cancer (e.g., a bladder cancer, e.g., an urothelial bladder cancer (UBC)) is likely to respond to treatment comprising a PD-L1 axis binding antagonist. Also provided herein are methods for predicting responsiveness of a patient suffering from a cancer (e.g., UBC) to treatment comprising a PD-L1 axis binding antagonist. Further provided herein are methods for selecting a therapy for a patient suffering from a cancer (e.g., UBC). Any of the preceding methods may be based on the expression level of a biomarker provided herein, for example, PD-L1 expression in a tumor sample, e.g., in tumor-infiltrating immune cells. Any of the methods may further be based on the determination of a tumor sample subtype. Any of the methods may further include administering to the patient a PD-L1 axis binding antagonist (for example, as described in Section D, below) to the patient. Any of the methods may further include administering an effective amount of a second therapeutic agent to the patient.

The invention provides a method for determining whether a patient suffering from a bladder cancer is likely to respond to treatment comprising a PD-L1 axis binding antagonist, the method comprising determining the expression level of PD-L1 in tumor-infiltrating immune cells in a tumor sample obtained from the patient, wherein a detectable expression level of PD-L1 in tumor-infiltrating immune cells that comprise about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, or about 50% or more) of the tumor sample indicates that the patient is likely to respond to treatment comprising a PD-L1 axis binding antagonist. For example, in some instances, a detectable expression level of PD-L1 in tumor-infiltrating immune cells that comprise about 1% or more of the tumor sample indicates that the patient is likely to respond to treatment comprising a PD-L1 axis binding antagonist. In some instances, a detectable expression level of PD-L1 in tumor-infiltrating immune cells that comprise about 5% or more of the tumor sample indicates that the patient is likely to respond to treatment comprising a PD-L1 axis binding antagonist.

In other instances, a detectable expression level of PD-L1 in tumor-infiltrating immune cells that comprise about 10% or more of the tumor sample indicates that the patient is likely to respond to treatment comprising a PD-L1 axis binding antagonist.

The invention further provides a method for predicting responsiveness of a patient suffering from a bladder cancer to treatment comprising a PD-L1 axis binding antagonist, the method comprising determining the expression level of PD-L1 in tumor-infiltrating immune cells in a tumor sample obtained from the patient, wherein a detectable expression level of PD-L1 in tumor-infiltrating immune cells that comprise about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, or about 50% or more) of the tumor sample indicates that the patient is likely to respond to treatment comprising a PD-L1 axis binding antagonist. For example, in some instances, a detectable expression level of PD-L1 in tumor-infiltrating immune cells that comprise about 1% or more of the tumor sample indicates that the patient is likely to respond to treatment comprising a PD-L1 axis binding antagonist. In some instances, a detectable expression level of PD-L1 in tumor-infiltrating immune cells that comprise about 5% or more of the tumor sample indicates that the patient is likely to respond to treatment comprising a PD-L1 axis binding antagonist.

In other instances, a detectable expression level of PD-L1 in tumor-infiltrating immune cells that comprise about 10% or more of the tumor sample indicates that the patient is likely to respond to treatment comprising a PD-L1 axis binding antagonist.

The invention yet also provides a method for selecting a therapy for a patient suffering from a bladder cancer, the method comprising determining the expression level of PD-L1 in tumor-infiltrating immune cells in a tumor sample obtained from the patient, and selecting a therapy comprising a PD-L1 axis binding antagonist for the patient based on a detectable expression level of PD-L1 in tumor-infiltrating immune cells that comprise about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, or about 50% or more) of the tumor sample.

For example, in some instances, the method includes selecting a therapy comprising a PD-L1 axis binding antagonist based on a detectable expression level of PD-L1 in tumor-infiltrating immune cells that comprise about 1% or more of the tumor sample. In some instances, a detectable expression level of PD-L1 in tumor-infiltrating immune cells that comprise about 5% or more of the tumor sample indicates that the patient is likely to respond to treatment comprising a PD-L1 axis binding antagonist. In other instances, the method includes selecting a therapy comprising a PD-L1 axis binding antagonist based on a detectable expression level of PD-L1 in tumor-infiltrating immune cells that comprise about 10% or more of the tumor sample.

In any of the preceding methods, the tumor-infiltrating immune cells may cover about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, about 50% or more, about 60% or more, about 65% or more, about 70% or more, about 75% or more, about 80% or more, about 85% or more, or about 90% or more) of the tumor area in a section of the tumor sample obtained from the patient.

For example, in some instances, the tumor-infiltrating immune cells may cover about 1% or more of the tumor area in a section of the tumor sample. In some instances, the tumor-infiltrating immune cells may cover about 5% or more of the tumor area in a section of the tumor sample. In other instances, the tumor-infiltrating immune cells may cover about 10% or more of the tumor area in a section of the tumor sample. In some instances, the tumor-infiltrating immune cells may cover about 15% or more of the tumor area in a section of the tumor sample. In yet other instances, the tumor-infiltrating immune cells may cover about 20% or more of the tumor area in a section of the tumor sample. In further instances, the tumor-infiltrating immune cells may cover about 25% or more of the tumor area in a section of the tumor sample. In some instances, the tumor-infiltrating immune cells may cover about 30% or more of the tumor area in a section of the tumor sample. In some instances, the tumor-infiltrating immune cells may cover about 35% or more of the tumor area in a section of the tumor sample. In some instances, the tumor-infiltrating immune cells may cover about 40% or more of the tumor area in a section of the tumor sample. In some instances, the tumor-infiltrating immune cells may cover about 50% or more of the tumor area in a section of the tumor sample.

In any of the preceding methods, about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 99% or more) of the tumor-infiltrating immune cells in the tumor sample may express a detectable expression level of PD-L1.

In any of the preceding methods, the method may further include administering to the patient a therapeutically effective amount of a PD-L1 axis binding antagonist based on the expression level of PD-L1 in tumor-infiltrating immune cells in the tumor sample. The PD-L1 axis binding antagonist may be any PD-L1 axis binding antagonist known in the art or described herein, for example, in Section D, below.

For example, in some instances, the PD-L1 axis binding antagonist is selected from the group consisting of a PD-L1 binding antagonist, a PD-1 binding antagonist, and a PD-L2 binding antagonist. In some instances, the PD-L1 axis binding antagonist is a PD-L1 binding antagonist. In some instances, the PD-L1 binding antagonist inhibits the binding of PD-L1 to one or more of its ligand binding partners. In other instances, the PD-L1 binding antagonist inhibits the binding of PD-L1 to PD-1. In yet other instances, the PD-L1 binding antagonist inhibits the binding of PD-L1 to B7-1. In some instances, the PD-L1 binding antagonist inhibits the binding of PD-L1 to both PD-1 and B7-1. In some instances, the PD-L1 binding antagonist is an antibody. In some instances, the antibody is selected from the group consisting of: YW243.55.S70, MPDL3280A (atezolizumab), MDX-1105, MED14736 (durvalumab), and MSB0010718C (avelumab). In some instances, the antibody comprises a heavy chain comprising HVR-H1 sequence of SEQ ID NO:19, HVR-H2 sequence of SEQ ID NO:20, and HVR-H3 sequence of SEQ ID NO:21; and a light chain comprising HVR-L1 sequence of SEQ ID NO:22, HVR-L2 sequence of SEQ ID NO:23, and HVR-L3 sequence of SEQ ID NO:24. In some instances, the antibody comprises a heavy chain variable region comprising the amino acid sequence of SEQ ID NO:26 and a light chain variable region comprising the amino acid sequence of SEQ ID NO:4.

In some instances, the PD-L1 axis binding antagonist is a PD-1 binding antagonist. For example, in some instances, the PD-1 binding antagonist inhibits the binding of PD-1 to one or more of its ligand binding partners. In some instances, the PD-1 binding antagonist inhibits the binding of PD-1 to PD-L1. In other instances, the PD-1 binding antagonist inhibits the binding of PD-1 to PD-L2. In yet other instances, the PD-1 binding antagonist inhibits the binding of PD-1 to both PD-L1 and PD-L2. In some instances, the PD-1 binding antagonist is an antibody. In some instances, the antibody is selected from the group consisting of: MDX 1106 (nivolumab), MK-3475 (pembrolizumab), CT-011 (pidilizumab), MEDI-0680 (AMP-514), PDR001, REGN2810, and BGB-108. In some instances, the PD-1 binding antagonist is an Fc-fusion protein. For example, in some instances, the Fc-fusion protein is AMP-224.

In some instances, the method further includes administering to the patient an effective amount of a second therapeutic agent. In some instances, the second therapeutic agent is selected from the group consisting of a cytotoxic agent, a growth-inhibitory agent, a radiation therapy agent, an antiangiogenic agent, and combinations thereof.

In any of the preceding instances, the bladder cancer may be an urothelial bladder cancer, including but not limited to a non-muscle invasive urothelial bladder cancer, a muscle-invasive urothelial bladder cancer, or a metastatic urothelial bladder cancer. In some instances, the urothelial bladder cancer is a metastatic urothelial bladder cancer.

Presence and/or expression levels/amount of a biomarker (e.g., PD-L1) can be determined qualitatively and/or quantitatively based on any suitable criterion known in the art, including but not limited to DNA, mRNA, cDNA, proteins, protein fragments, and/or gene copy number.

In any of the preceding methods, the sample obtained from the patient is selected from the group consisting of tissue, whole blood, plasma, serum, and combinations thereof. In some instances, the sample is a tissue sample. In some instances, the tissue sample is a tumor sample. In some instances, the tumor sample comprises tumor-infiltrating immune cells, tumor cells, stromal cells, or any combinations thereof. In any of the preceding instances, the tumor sample may be a formalin-fixed and paraffin-embedded (FFPE) tumor sample, an archival tumor sample, a fresh tumor sample, or a frozen tumor sample.

In any of the preceding methods, the method may include determining the presence and/or expression level of an additional biomarker. In some instances, the additional biomarker is a biomarker described in WO 2014/151006, the entire disclosure of which is incorporated herein by reference. In some instances, the additional biomarker is selected from circulating Ki-67+CD8+ T cells, interferon gamma, MCP-1, or a myeloid cell-related gene. In some instances, the myeloid-cell related gene is selected from IL18, CCL2, and IL1B.

The presence and/or expression level/amount of various biomarkers described herein in a sample can be analyzed by a number of methodologies, many of which are known in the art and understood by the skilled artisan, including, but not limited to, immunohistochemistry ("IHC"), Western blot analysis, immunoprecipitation, molecular binding assays, ELISA, ELIFA, fluorescence activated cell sorting ("FACS"), MassARRAY, proteomics, quantitative blood based assays (e.g., Serum ELISA), biochemical enzymatic activity assays, in situ hybridization, fluorescence in situ hybridization (FISH), Southern analysis, Northern analysis, whole genome sequencing, polymerase chain reaction (PCR) including quantitative real time PCR (qRT-PCR) and other amplification type detection methods, such as, for example, branched DNA, SISBA, TMA and the like, RNA-Seq, microarray analysis, gene expression profiling, and/or serial analysis of gene expression ("SAGE"), as well as any one of the wide variety of assays that can be performed by protein, gene, and/or tissue array analysis. Typical protocols for evaluating the status of genes and gene products are found, for example in Ausubel et al., eds., 1995, Current Protocols In Molecular Biology, Units 2 (Northern Blotting), 4 (Southern Blotting), 15 (Immunoblotting) and 18 (PCR Analysis). Multiplexed immunoassays such as those available from Rules Based Medicine or Meso Scale Discovery ("MSD") may also be used.

In any of the preceding methods, the presence and/or expression level/amount of a biomarker (e.g., PD-L1) is measured by determining protein expression levels of the biomarker. In certain instances, the method comprises contacting the biological sample with antibodies that specifically bind to a biomarker (e.g., anti-PD-L1 antibodies) described herein under conditions permissive for binding of the biomarker, and detecting whether a complex is formed between the antibodies and biomarker. Such method may be an in vitro or in vivo method. In some instances, an antibody is used to select subjects eligible for therapy with a PD-L1 axis binding antagonist, e.g., a biomarker for selection of individuals. Any method of measuring protein expression levels known in the art or provided herein may be used. For example, in some instances, a protein expression level of a biomarker (e.g., PD-L1) is determined using a method selected from the group consisting of flow cytometry (e.g., fluorescence-activated cell sorting (FACS™)), Western blot, enzyme-linked immunosorbent assay (ELISA), immunoprecipitation, immunohistochemistry (IHC), immunofluorescence, radioimmunoassay, dot blotting, immunodetection methods, HPLC, surface plasmon resonance, optical spectroscopy, mass spectrometry, and HPLC. In some instances, the protein expression level of the biomarker (e.g., PD-L1) is determined in tumor-infiltrating immune cells. In some instances, the protein expression level of the biomarker (e.g., PD-L1) is determined in tumor cells. In some instances, the protein expression level of the biomarker (e.g., PD-L1) is determined in tumor-infiltrating immune cells and/or in tumor cells.

In certain instances, the presence and/or expression level/amount of a biomarker protein (e.g., PD-L1) in a sample is examined using IHC and staining protocols. IHC staining of tissue sections has been shown to be a reliable method of determining or detecting the presence of proteins in a sample. In some instances of any of the methods, assays and/or kits, the biomarker is PD-L1. In one instance, expression level of biomarker is determined using a method comprising: (a) performing IHC analysis of a sample (such as a tumor sample obtained from a patient) with an antibody; and (b) determining expression level of a biomarker in the sample. In some instances, IHC staining intensity is determined relative to a reference. In some instances, the reference is a reference value. In some instances, the reference is a reference sample (e.g., a control cell line staining sample, a tissue sample from non-cancerous patient, or a PD-L1-negative tumor sample).

IHC may be performed in combination with additional techniques such as morphological staining and/or in situ hybridization (e.g., FISH). Two general methods of IHC are available; direct and indirect assays.

According to the first assay, binding of antibody to the target antigen is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for IHC typically will be labeled with a detectable moiety. Numerous labels are available which can be generally grouped into the following categories: (a) radioisotopes, such as $^{35}S$, $^{14}C$, $^{125}I$, $^{3}H$, and $^{131}I$; (b) colloidal gold particles; (c) fluorescent labels including, but are not limited to, rare earth chelates (europium chelates), Texas Red, rhodamine, fluorescein, dansyl, lissamine, umbelliferone, phycocrytherin, phycocyanin, or commercially-available fluorophores such as SPECTRUM ORANGE7 and SPECTRUM GREEN7 and/or derivatives of any one or more of the above; (d) various enzyme-substrate labels are available and U.S. Pat. No. 4,275,149 provides a review of some of these. Examples of enzymatic labels include luciferases (e.g., firefly luciferase and bacterial luciferase; see, e.g., U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

Examples of enzyme-substrate combinations include, for example, horseradish peroxidase (HRPO) with hydrogen peroxidase as a substrate; alkaline phosphatase (AP) with para-Nitrophenyl phosphate as chromogenic substrate; and β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase). For a general review of these, see, for example, U.S. Pat. Nos. 4,275,149 and 4,318,980.

Specimens may be prepared, for example, manually, or using an automated staining instrument (e.g., a Ventana BENCHMARK XT™ automated staining instrument or BENCHMARK ULTRA™ automated staining instrument; see, e.g., Example 1 below). Specimens thus prepared may be mounted and coverslipped. Slide evaluation is then determined, for example, using a microscope, and staining intensity criteria, routinely used in the art, may be employed. In one instance, it is to be understood that when cells and/or tissue from a tumor is examined using IHC, staining is generally determined or assessed in tumor cell(s) and/or tissue (as opposed to stromal or surrounding tissue that may be present in the sample). In some instances, it is understood that when cells and/or tissue from a tumor is examined using IHC, staining includes determining or assessing in tumor-infiltrating immune cells, including intratumoral or peritumoral immune cells. In some instances, the presence of a biomarker (e.g., PD-L1) is detected by IHC in >0% of the sample, in at least 1% of the sample, in at least 5% of the sample, in at least 10% of the sample, in at least 15% of the sample, in at least 15% of the sample, in at least 20% of the sample, in at least 25% of the sample, in at least 30% of the sample, in at least 35% of the sample, in at least 40% of the sample, in at least 45% of the sample, in at least 50% of the sample, in at least 55% of the sample, in at least 60% of the sample, in at least 65% of the sample, in at least 70% of the sample, in at least 75% of the sample, in at least 80% of the sample, in at least 85% of the sample, in at least 90% of the sample, in at least 95% of the sample, or more. Samples may be scored using any of the criteria described herein (see, e.g., Table 2), for example, by a pathologist or automated image analysis.

In some instances of any of the methods described herein, PD-L1 is detected by immunohistochemistry using an anti-PD-L1 diagnostic antibody (i.e., primary antibody). In some instances, the PD-L1 diagnostic antibody specifically binds human PD-L1. In some instances, the PD-L1 diagnostic antibody is a non-human antibody. In some instances, the PD-L1 diagnostic antibody is a rat, mouse, or rabbit antibody. In some instances, the PD-L1 diagnostic antibody is a rabbit antibody. In some instances, the PD-L1 diagnostic antibody is a monoclonal antibody. In some instances, the PD-L1 diagnostic antibody is directly labeled. In other instances, the PD-L1 diagnostic antibody is indirectly labeled.

In some instances of any of the preceding methods, the expression level of PD-L1 is detected in tumor-infiltrating immune cells, tumor cells, or combinations thereof using IHC. Tumor-infiltrating immune cells include, but are not limited to, intratumoral immune cells, peritumoral immune cells or any combinations thereof, and other tumor stroma cells (e.g., fibroblasts). Such tumor infiltrating immune cells may be T lymphocytes (such as CD8+T lymphocytes and/or CD4+T lymphocytes), B lymphocytes, or other bone marrow-lineage cells including granulocytes (neutrophils, eosinophils, basophils), monocytes, macrophages, dendritic cells (e.g., interdigitating dendritic cells), histiocytes, and natural killer cells. In some instances, the staining for PD-L1 is detected as membrane staining, cytoplasmic staining and combinations thereof. In other instances, the absence of PD-L1 is detected as absent or no staining in the sample.

In any of the preceding methods, the expression level of a biomarker (e.g., PD-L1) may be a nucleic acid expression level. In some instances, the nucleic acid expression level is determined using qPCR, rtPCR, RNA-seq, multiplex qPCR or RT-qPCR, microarray analysis, SAGE, MassARRAY technique, or in situ hybridization (e.g., FISH). In some instances the expression level of a biomarker (e.g., PD-L1) is determined in tumor cells, tumor infiltrating immune cells, stromal cells, or combinations thereof. In some instances, the expression level of a biomarker (e.g., PD-L1) is determined in tumor-infiltrating immune cells. In some instances, the expression level of a biomarker (e.g., PD-L1) is determined in tumor cells.

Methods for the evaluation of mRNAs in cells are well known and include, for example, hybridization assays using complementary DNA probes (such as in situ hybridization using labeled riboprobes specific for the one or more genes, Northern blot and related techniques) and various nucleic acid amplification assays (such as RT-PCR using complementary primers specific for one or more of the genes, and other amplification type detection methods, such as, for example, branched DNA, SISBA, TMA and the like). In addition, such methods can include one or more steps that allow one to determine the levels of target mRNA in a biological sample (e.g., by simultaneously examining the levels a comparative control mRNA sequence of a "housekeeping" gene such as an actin family member). Optionally, the sequence of the amplified target cDNA can be determined. Optional methods include protocols which examine or detect mRNAs, such as target mRNAs, in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes whose expression correlates with increased or reduced clinical benefit of treatment comprising a PD-L1 axis binding antagonist may be arrayed on a solid support. Hybridization of a labeled probe with a particular array member indicates that the sample from which the probe was derived expresses that gene.

In certain instances, the presence and/or expression levels/amount of a biomarker in a first sample is increased or elevated as compared to presence/absence and/or expression levels/amount in a second sample. In certain instances, the presence/absence and/or expression levels/amount of a biomarker in a first sample is decreased or reduced as compared to presence and/or expression levels/amount in a second sample. In certain instances, the second sample is a reference sample, reference cell, reference tissue, control sample, control cell, or control tissue. Additional disclosures for determining the presence/absence and/or expression levels/amount of a gene are described herein.

In certain instances, a reference sample, reference cell, reference tissue, control sample, control cell, or control tissue is a single sample or a combination of multiple samples from the same subject or individual that are obtained at one or more different time points than when the test sample is obtained. For example, a reference sample, reference cell, reference tissue, control sample, control cell, or control tissue is obtained at an earlier time point from the same subject or individual than when the test sample is obtained. Such reference sample, reference cell, reference tissue, control sample, control cell, or control tissue may be useful if the reference sample is obtained during initial diagnosis of cancer and the test sample is later obtained when the cancer becomes metastatic.

In certain embodiments, a reference sample, reference cell, reference tissue, control sample, control cell, or control tissue is a combination of multiple samples from one or more healthy individuals who are not the patient. In certain embodiments, a reference sample, reference cell, reference tissue, control sample, control cell, or control tissue is a combination of multiple samples from one or more individuals with a disease or disorder (e.g., cancer) who are not the subject or individual. In certain embodiments, a reference sample, reference cell, reference tissue, control sample, control cell, or control tissue is pooled RNA samples from normal tissues or pooled plasma or serum samples from one or more individuals who are not the patient. In certain embodiments, a reference sample, reference cell, reference tissue, control sample, control cell, or control tissue is pooled RNA samples from tumor tissues or pooled plasma or serum samples from one or more individuals with a disease or disorder (e.g., cancer) who are not the patient.

In some embodiments of any of the methods, elevated or increased expression refers to an overall increase of about any of 10%, 20%, 30%, 40%, 50%, 60%, 70%, 80%, 90%, 95%, 96%, 97%, 98%, 99% or greater, in the level of biomarker (e.g., protein or nucleic acid (e.g., gene or mRNA)), detected by standard art-known methods such as those described herein, as compared to a reference sample, reference cell, reference tissue, control sample, control cell, or control tissue. In certain embodiments, the elevated expression refers to the increase in expression level/amount of a biomarker in the sample wherein the increase is at least about any of 1.5×, 1.75×, 2×, 3×, 4×, 5×, 6×, 7×, 8×, 9×, 10×, 25×, 50×, 75×, or 100× the expression level/amount of the respective biomarker in a reference sample, reference cell, reference tissue, control sample, control cell, or control tissue. In some embodiments, elevated expression refers to an overall increase of greater than about 1.5-fold, about 1.75-fold, about 2-fold, about 2.25-fold, about 2.5-fold, about 2.75-fold, about 3.0-fold, or about 3.25-fold as compared to a reference sample, reference cell, reference tissue, control sample, control cell, control tissue, or internal control (e.g., housekeeping gene).

In some embodiments of any of the methods, reduced expression refers to an overall reduction of about any of 10%, 20%, 30%, 40%, 50%, 60%, 70%, 80%, 90%, 95%, 96%, 97%, 98%, 99% or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue. In certain embodiments, reduced expression refers to the decrease in expression level/amount of a biomarker in the sample wherein the decrease is at least about any of 0.9×, 0.8×, 0.7×, 0.6×, 0.5×, 0.4×, 0.3×, 0.2×, 0.1×, 0.05×, or 0.01× the expression level/amount of the respective biomarker in a reference sample, reference cell, reference tissue, control sample, control cell, or control tissue.

B. Diagnostic Methods Based on Assessment of Tumor Subtype

Provided herein are methods that may be used individually or in combination with any of the preceding methods presented in Section A, above, for determining whether a patient suffering from a cancer (e.g., a bladder cancer (e.g., a UBC)) is likely to respond to treatment comprising a PD-L1 axis binding antagonist based on an assessment of tumor subtype. For example, the invention provides a method for determining whether a patient suffering from a bladder cancer is likely to respond to treatment comprising a PD-L1 axis binding antagonist, the method comprising determining the subtype of a tumor from a sample of the tumor obtained from the patient, wherein a luminal subtype tumor indicates that the patient is likely to respond to treatment comprising a PD-L1 axis binding antagonist. In some instances, the determination of a tumor sample being a luminal subtype II tumor indicates that the patient is likely to respond to treatment comprising a PD-L1 axis binding antagonist. In some instances, the level of one or more (e.g., 1, 2, 3, 4, 5, 6, 7, 8, 9, 10, 11, 12, 13, 14, 15, or 16) of the biomarkers listed in Table 1 relative to reference levels of the biomarkers can be used in the determination of tumor subtype. In some instances, the level of one or more (e.g., 1, 2, 3, 4, 5, 6, 7, 8, 9, 10, 11, 12, 13, 14, 15, or 16) of the biomarkers listed in Table 1 relative to reference levels of the biomarkers can be used in the determination of a luminal subtype tumor. In some instances, the level of one or more (e.g., 1, 2, 3, 4, 5, 6, 7, 8, 9, 10, 11, 12, 13, 14, 15, or 16) of the biomarkers listed in Table 1 relative to reference levels of the biomarkers can be used in the determination of a luminal subtype II tumor. In some instances, the level of one or more (e.g., 1, 2, 3, 4, 5, 6, 7, 8, 9, 10, 11, 12, 13, 14, 15, or 16) of the biomarkers listed in Table 1 relative to reference levels of the biomarkers can be used in the determination of whether a patient suffering from a cancer (e.g., a bladder cancer (e.g., a UBC)) is likely to respond to treatment comprising a PD-L1 axis binding antagonist. In other instances, for example, an increase and/or a decrease in the level one or more (e.g., 1, 2, 3, 4, 5, 6, 7, 8, 9, 10, 15, or 16) of the biomarkers listed in Table 1 relative to reference levels of the biomarkers in combination with a detectable expression level of PD-L1 in tumor-infiltrating immune cells that comprise about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, or about 50% or more) of the tumor sample can be used to determine whether a patient suffering from a cancer (e.g., a bladder cancer (e.g., a UBC)) is likely to respond to treatment comprising a PD-L1 axis binding antagonist. Any of these methods may further include administering to the patient a PD-L1 axis binding antagonist (e.g., as described in Section D, below). Any of these methods may also further include administering an effective amount of a second therapeutic agent to the patient.

Table 1

| Subtype-Associated Biomarkers | |
| --- | --- |
| Group | Biomarker |
| A | FGFR3 |
| | miR-99a-5p |
| | miR-100-5p |
| | CDKN2A |
| B | KRT5 |
| | KRT6A |
| | KRT14 |
| | EGFR |
| C | GATA3 |
| | FOXA1 |

Table 1-continued

| Subtype-Associated Biomarkers | |
|---|---|
| Group | Biomarker |
| | UPK3A |
| | miR-200a-3p |
| | miR-200b-3p |
| | E-cadherin |
| D | ERBB2 |
| | ESR2 |

Methods for predicting responsiveness of a patient suffering from a cancer (e.g., a bladder cancer (e.g., a UBC)) to treatment comprising a PD-L1 axis binding antagonist based on the assessment of tumor subtype may be used individually or in combination with any of the preceding methods presented in Section A, above. For example, the invention provides a method for predicting whether a patient suffering from a bladder cancer is likely to respond to treatment comprising a PD-L1 axis binding antagonist, the method comprising determining the subtype of a tumor from a sample of the tumor obtained from the patient, wherein a luminal subtype tumor indicates that the patient is likely to respond to treatment comprising a PD-L1 axis binding antagonist. In some instances, the determination of a tumor sample being a luminal subtype II tumor indicates that the patient is likely to respond to treatment comprising a PD-L1 axis binding antagonist. In some instances, the level of one or more (e.g., 1, 2, 3, 4, 5, 6, 7, 8, 9, 10, 11, 12, 13, 14, 15, or 16) of the biomarkers listed in Table 1 relative to reference levels of the biomarkers can be used in the determination of tumor subtype. In some instances, the level of one or more (e.g., 1, 2, 3, 4, 5, 6, 7, 8, 9, 10, 11, 12, 13, 14, 15, or 16) of the biomarkers listed in Table 1 relative to reference levels of the biomarkers can be used in the determination of a luminal subtype tumor. In some instances, the level of one or more (e.g., 1, 2, 3, 4, 5, 6, 7, 8, 9, 10, 11, 12, 13, 14, 15, or 16) of the biomarkers listed in Table 1 relative to reference levels of the biomarkers can be used in the determination of a luminal subtype II tumor. In some instances, the level of one or more (e.g., 1, 2, 3, 4, 5, 6, 7, 8, 9, 10, 11, 12, 13, 14, 15, or 16) of the biomarkers listed in Table 1 relative to reference levels of the biomarkers can be used in the determination of whether a patient suffering from a cancer (e.g., a bladder cancer (e.g., a UBC)) is likely to respond to treatment comprising a PD-L1 axis binding antagonist. In other instances, for example, an increase and/or a decrease in the level one or more (e.g., 1, 2, 3, 4, 5, 6, 7, 8, 9, 10, 15, or 16) of the biomarkers listed in Table 1 relative to reference levels of the biomarkers in combination with a detectable expression level of PD-L1 in tumor-infiltrating immune cells that comprise about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, or about 50% or more) of the tumor sample can predict whether a patient suffering from a cancer (e.g., a bladder cancer (e.g., a UBC)) is likely to respond to treatment comprising a PD-L1 axis binding antagonist.

Any of the methods may further include administering to the patient a PD-L1 axis binding antagonist (e.g., as described in Section D, below). Any of the methods may further include administering an effective amount of a second therapeutic agent to the patient.

Methods for selecting a therapy for a patient suffering from a cancer (e.g., a bladder cancer (e.g., a UBC)), comprising selecting a PD-L1 axis binding antagonist based on the assessment of tumor subtype may be used individually or in combination with any of the preceding methods presented in Section A, above. In some instances, the method comprises determining the subtype of a tumor from a sample of the tumor obtained from the patient, wherein a PD-L1 axis binding antagonist is selected based on the determination that the tumor is a luminal subtype tumor. In some instances, a PD-L1 axis binding antagonist is selected based on the determination that the tumor is a luminal subtype II tumor. In some instances, the level of one or more (e.g., 1, 2, 3, 4, 5, 6, 7, 8, 9, 10, 11, 12, 13, 14, 15, or 16) of the biomarkers listed in Table 1 relative to reference levels of the biomarkers can be used in the determination of tumor subtype. In some instances, the level of one or more (e.g., 1, 2, 3, 4, 5, 6, 7, 8, 9, 10, 11, 12, 13, 14, 15, or 16) of the biomarkers listed in Table 1 relative to reference levels of the biomarkers can be used in the determination of a luminal subtype tumor. In some instances, the level of one or more (e.g., 1, 2, 3, 4, 5, 6, 7, 8, 9, 10, 11, 12, 13, 14, 15, or 16) of the biomarkers listed in Table 1 relative to reference levels of the biomarkers can be used in the determination of a luminal subtype II tumor. In some instances, the level of one or more (e.g., 1, 2, 3, 4, 5, 6, 7, 8, 9, 10, 11, 12, 13, 14, 15, or 16) of the biomarkers listed in Table 1 relative to reference levels of the biomarkers can be used in the selecting a PD-L1 axis binding antagonist as the appropriate therapy for a patient suffering from a cancer (e.g., a bladder cancer (e.g., a UBC)). In other instances, for example, an increase and/or a decrease in the level one or more (e.g., 1, 2, 3, 4, 5, 6, 7, 8, 9, 10, 15, or 16) of the biomarkers listed in Table 1 relative to reference levels of the biomarkers in combination with a detectable expression level of PD-L1 in tumor-infiltrating immune cells that comprise about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, or about 50% or more) tumor sample can inform the selection of a PD-L1 axis binding antagonist for a patient suffering from a cancer (e.g., a bladder cancer (e.g., a UBC)). Any of the methods may further include administering to the patient a PD-L1 axis binding antagonist (e.g., as described in Section D, below). Any of the methods may further include administering an effective amount of a second therapeutic agent to the patient.

In any of the preceding methods, the biomarkers set forth in Table 1 have been determined to have increased and/or decreased by about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, about 50% or more, about 60% or more, about 65% or more, about 70% or more, about 75% or more, about 80% or more, about 85% or more, or about 90% or more) relative to reference levels of the biomarkers set forth in Table 1. For example, in some instances, the level of one or more biomarkers was determined to have increased and/or decreased by about 1% or more. In some instances, the level of one or more biomarkers was determined to have increased and/or decreased by about 5% or more. In other instances, the level of one or more biomarkers was determined to have increased and/or decreased by about 10% or more. In some instances, the level of one or more biomarkers was determined to have increased and/or decreased by about 15% or more. In yet other instances, the level of one or more biomarkers was determined to have increased and/or decreased by about 20% or more. In further instances, the level of one or more biomarkers was determined to have increased and/or decreased by about 25% or more. In some instances, the level of one or more biomarkers was determined to have increased and/or decreased by about 30% or more. In some instances, the level of one or more biomarkers was determined to have increased and/or decreased by about 35% or more. In some instances, the level of one or more biomarkers was determined to have increased and/or decreased by about 40% or more. In some instances, the level of one or more biomarkers was determined to have increased and/or decreased by about 50% or more In any of the preceding instances, a tumor sample obtained from the patient has been determined to be a luminal subtype tumor (e.g., a UBC luminal subtype tumor). In some instances, the tumor has been determined to be a luminal subtype II tumor. In some instances, the level of expression of at least one or more (e.g., 1, 2, 3, or 4) biomarkers selected from Table 1, Group A (e.g., FGFR3, miR-99a-5p, miR-100-5p, CDKN2A) and at least one or more (e.g., 1, 2, 3, or 4) biomarkers selected from Table 1, Group B (e.g., KRT5, KRT6A, KRT14, EGFR) can be used to determine luminal subtype II classification. In some instances, the level of expression of at least one or more (e.g., 1, 2, 3, or 4) biomarkers selected from Table 1, Group A (e.g., FGFR3, miR-99a-5p, miR-100-5p, CDKN2A) and at least one or more (e.g., 1, 2, 3, 4, 5, or 6) biomarkers selected from Table 1, Group C (e.g., GATA3, FOXA1, UPK3A, miR-200a-3p, miR-200b-3p, E-cadherin) can be used to determine luminal subtype II classification. In some instances, the level of expression of at least one or more (e.g., 1, 2, 3, or 4) biomarkers selected from Table 1, Group A (e.g., FGFR3, miR-99a-5p, miR-100-5p, CDKN2A) and at least one or more (e.g., 1 or 2) biomarkers selected from Table 1, Group D (e.g., ERBB2, ESR2) can be used to determine luminal subtype II classification. In some instances, the level of expression of at least one or more (e.g., 1, 2, 3, or 4) biomarkers selected from Table 1, Group A (e.g., FGFR3, miR-99a-5p, miR-100-5p, CDKN2A); at least one or more (e.g., 1, 2, 3, 4, 5, or 6) biomarkers selected from Table 1, Group C (e.g., GATA3, FOXA1, UPK3A, miR-200a-3p, miR-200b-3p, E-cadherin); and at least one or more (e.g., 1 or 2) biomarkers selected from Table 1, Group D (e.g., ERBB2, ESR2) can be used to determine luminal subtype II classification. In some instances, the level of expression of at least one or more (e.g., 1, 2, 3, or 4) biomarkers selected from Table 1, Group A (e.g., FGFR3, miR-99a-5p, miR-100-5p, CDKN2A); at least one or more (e.g., 1, 2, 3, or 4) biomarkers selected from Table 1, Group B (e.g., KRT5, KRT6A, KRT14, EGFR); at least one or more (e.g., 1, 2, 3, 4, 5, or 6) biomarkers selected from Table 1, Group C (e.g., GATA3, FOXA1, UPK3A, miR-200a-3p, miR-200b-3p, E-cadherin); and at least one or more (e.g., 1 or 2) biomarkers selected from Table 1, Group D (e.g., ERBB2, ESR2) can be used to determine luminal subtype II classification. In any of the preceding instances the level of a biomarker is an mRNA level, a protein level, and/or a microRNA (e.g., miRNA) level.

In some instances, an increased level of expression of at least one of miR-99a-5p, miR-100-5p, and CDKN2A, and/or a decreased level of expression of FGFR3 in combination with a decreased level of expression of at least one of KRT5, KRT6A, KRT14, and EGFR compared to reference levels of the biomarkers can be used to determine luminal subtype II classification. In some instances, an increased level of expression of at least one of miR-99a-5p, miR-100-5p, and CDKN2A, and/or a decreased level of expression of FGFR3 in combination with an increased level of at least one of GATA3, FOXA1, UPK3A, miR-200a-3p, miR-200b-3p, and E-cadherin compared to reference levels of the biomarkers can be used to determine luminal subtype II classification. In some instances, an increased level of expression of at least one of miR-99a-5p, miR-100-5p, and CDKN2A, and/or a decreased level of expression of FGFR3 in combination with an increased level of ERBB2 and/or ESR2 compared to reference levels of the biomarkers can be used to determine luminal subtype II classification. In some instances, an increased level of expression of at least one of miR-99a-5p, miR-100-5p, and CDKN2A, and/or a decreased level of expression of FGFR3; an increased level of at least one of GATA3, FOXA1, UPK3A, miR-200a-3p, miR-200b-3p, and E-cadherin; and an increased level of ERBB2 and/or ESR2 compared to reference levels of the biomarkers can be used to determine luminal subtype II classification.

In some instances, an increased level of expression of at least one of miR-99a-5p, miR-100-5p, and CDKN2A, and/or a decreased level of expression of FGFR3; a decreased level of expression of at least one of KRT5, KRT6A, KRT14, and EGFR; and an increased level of ERBB2 and/or ESR2 compared to reference levels of the biomarkers can be used to determine luminal subtype II classification. In some instances, an increased level of expression of at least one of miR-99a-5p, miR-100-5p, and CDKN2A, and/or a decreased level of expression of FGFR3; a decreased level of expression of at least one of KRT5, KRT6A, KRT14, and EGFR; an increased level of expression of at least one of GATA3, FOXA1, UPK3A, miR-200a-3p, miR-200b-3p, and E-cadherin; and an increased level of ERBB2 and/or ESR2 compared to reference levels of the biomarkers can be used to determine luminal subtype II classification. In any of the preceding instances the level of a biomarker is an mRNA level, a protein level, and/or a microRNA (e.g., miRNA) level.

In some instances, the expression level of at least one of CDKN2A, GATA3, FOXA1, ERBB2, FGFR3, KRT5, KRT14, EGFR, CD8A, GZMA, GZMB, IFNG, CXCL9, CXCL10, PRF1, and TBX21 in the tumor sample obtained from the patient has been determined to have changed about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, or about 50% or more) relative to a reference level of the at least one gene.

In some instances, the expression level of at least one of CDKN2A, GATA3, FOXA1, and ERBB2 in the tumor sample obtained from the patient has been determined to be increased about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, or about 50% or more) relative to a reference level of the at least one gene, and/or the expression level of at least one of FGFR3, KRT5, KRT14, and EGFR in the tumor sample obtained from the patient has been determined to be decreased about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, or about 50% or more) relative to a reference level of the at least one gene.

In some instances, the expression levels of CDKN2A, GATA3, FOXA1, and ERBB2 in the tumor sample obtained from the patient have been determined to be increased about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, or about 50% or more) relative to reference levels of the genes, and/or the expression levels of FGFR3, KRT5, KRT14, and EGFR in the tumor sample obtained from the patient have been determined to be decreased about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, or about 50% or more) relative to reference levels of the genes.

In some instances, the expression levels of CDKN2A, GATA3, FOXA1, and ERBB2 in the tumor sample obtained from the patient have been determined to be increased about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, or about 50% or more) relative to reference levels of the genes, and the expression levels of FGFR3, KRT5, KRT14, and EGFR in the tumor sample obtained from the patient have been determined to be decreased about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, or about 50% or more) relative to reference levels of the genes.

In other instances, the expression level of miR-99a-5p or miR100-5p in the tumor sample obtained from the patient has been determined to have changed about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, or about 50% or more) relative to reference levels of the miRNAs. In other instances, the expression level of miR-99a-5p or miR100-5p in the tumor sample obtained from the patient has been determined to be increased relative to a reference level of the miRNA. In other instances, the expression level of miR-99a-5p or miR100-5p in the tumor sample obtained from the patient has been determined to be increased relative to a reference level of the miRNA. In some instances, the expression levels of miR-99a-5p and miR100-5p in the tumor sample obtained from the patient have been determined to be increased about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, or about 50% or more) relative to reference levels of the miRNAs.

In yet other instances, the expression level of at least one of CD8A, GZMA, GZMB, IFNG, CXCL9, CXCL10, PRF1, and TBX21 in the tumor sample obtained from the patient has been determined to be increased about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, or about 50% or more) relative to a reference level of the at least one gene. In some instances, the expression levels of at least CXCL9 and CXCL10 in the tumor sample obtained from the patient have been determined to be increased about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, or about 50% or more) relative to reference levels of the genes. In other instances, the luminal subtype tumor is a luminal cluster II subtype tumor.

In any of the preceding methods, the method may further include administering to the patient a therapeutically effective amount of a PD-L1 axis binding antagonist based on the expression level of PD-L1 in tumor-infiltrating immune cells in the tumor sample. The PD-L1 axis binding antagonist may be any PD-L1 axis binding antagonist known in the art or described herein, for example, in Section D, below.

For example, in some instances, the PD-L1 axis binding antagonist is selected from the group consisting of a PD-L1 binding antagonist, a PD-1 binding antagonist, and a PD-L2 binding antagonist. In some instances, the PD-L1 axis binding antagonist is a PD-L1 binding antagonist. In some instances, the PD-L1 binding antagonist inhibits the binding of PD-L1 to one or more of its ligand binding partners. In other instances, the PD-L1 binding antagonist inhibits the binding of PD-L1 to PD-1. In yet other instances, the PD-L1 binding antagonist inhibits the binding of PD-L1 to B7-1. In some instances, the PD-L1 binding antagonist inhibits the binding of PD-L1 to both PD-1 and B7-1. In some instances, the PD-L1 binding antagonist is an antibody. In some instances, the antibody is selected from the group consisting of: YW243.55.S70, MPDL3280A (atezolizumab), MDX-1105, MED14736 (durvalumab), and MSB0010718C (avelumab). In some instances, the antibody comprises a heavy chain comprising HVR-H1 sequence of SEQ ID NO:19, HVR-H2 sequence of SEQ ID NO:20, and HVR-H3 sequence of SEQ ID NO:21; and a light chain comprising HVR-L1 sequence of SEQ ID NO:22, HVR-L2 sequence of SEQ ID NO:23, and HVR-L3 sequence of SEQ ID NO:24.

In some instances, the antibody comprises a heavy chain variable region comprising the amino acid sequence of SEQ ID NO:26 and a light chain variable region comprising the amino acid sequence of SEQ ID NO:4.

In some instances, the PD-L1 axis binding antagonist is a PD-1 binding antagonist. For example, in some instances, the PD-1 binding antagonist inhibits the binding of PD-1 to one or more of its ligand binding partners. In some instances, the PD-1 binding antagonist inhibits the binding of PD-1 to PD-L1. In other instances, the PD-1 binding antagonist inhibits the binding of PD-1 to PD-L2. In yet other instances, the PD-1 binding antagonist inhibits the binding of PD-1 to both PD-L1 and PD-L2. In some instances, the PD-1 binding antagonist is an antibody. In some instances, the antibody is selected from the group consisting of: MDX 1106 (nivolumab), MK-3475 (pembrolizumab), CT-011 (pidilizumab), MEDI-0680 (AMP-514), PDR001, REGN2810, and BGB-108. In some instances, the PD-1 binding antagonist is an Fc-fusion protein. For example, in some instances, the Fc-fusion protein is AMP-224.

In some instances, the method further includes administering to the patient an effective amount of a second therapeutic agent. In some instances, the second therapeutic agent is selected from the group consisting of a cytotoxic agent, a growth-inhibitory agent, a radiation therapy agent, an anti-angiogenic agent, and combinations thereof.

In any of the preceding instances, the bladder cancer may be an urothelial bladder cancer (UBC), including but not limited to a non-muscle invasive urothelial bladder cancer, a muscle-invasive urothelial bladder cancer, or a metastatic urothelial bladder cancer. In some instances, the urothelial bladder cancer is a metastatic urothelial bladder cancer.

Presence and/or expression levels/amount of a biomarker (e.g., PD-L1) can be determined qualitatively and/or quantitatively based on any suitable criterion known in the art, including but not limited to DNA, mRNA, cDNA, proteins, protein fragments, and/or gene copy number.

In any of the preceding methods, the sample obtained from the patient is selected from the group consisting of tissue, whole blood, plasma, serum, and combinations thereof. In some instances, the sample is a tissue sample. In some instances, the tissue sample is a tumor sample. In some instances, the tumor sample comprises tumor-infiltrating immune cells, tumor cells, stromal cells, or any combinations thereof. In any of the preceding instances, the tumor sample may be a formalin-fixed and paraffin-embedded (FFPE) tumor sample, an archival tumor sample, a fresh tumor sample, or a frozen tumor sample.

In any of the preceding methods, the method may include determining the presence and/or expression level of an additional biomarker. In some instances, the additional biomarker is a biomarker described in WO 2014/151006, the entire disclosure of which is incorporated herein by reference. In some instances, the additional biomarker is selected from circulating Ki-67+CD8+ T cells, interferon gamma, MCP-1, or a myeloid cell-related gene. In some instances, the myeloid-cell related gene is selected from IL18, CCL2, and IL1B.

The presence and/or expression level/amount of various biomarkers described herein in a sample can be analyzed by a number of methodologies, many of which are known in the art and understood by the skilled artisan, including, but not limited to, immunohistochemistry ("IHC"), Western blot analysis, immunoprecipitation, molecular binding assays, ELISA, ELIFA, fluorescence activated cell sorting ("FACS"), MassARRAY, proteomics, quantitative blood based assays (e.g., Serum ELISA), biochemical enzymatic activity assays, in situ hybridization, fluorescence in situ hybridization (FISH), Southern analysis, Northern analysis, whole genome sequencing, polymerase chain reaction (PCR) including quantitative real time PCR (qRT-PCR) and other amplification type detection methods, such as, for example, branched DNA, SISBA, TMA and the like, RNA-Seq, microarray analysis, gene expression profiling, and/or serial analysis of gene expression ("SAGE"), as well as any one of the wide variety of assays that can be performed by protein, gene, and/or tissue array analysis. Typical protocols for evaluating the status of genes and gene products are found, for example in Ausubel et al., eds., 1995, Current Protocols In Molecular Biology, Units 2 (Northern Blotting), 4 (Southern Blotting), 15 (Immunoblotting) and 18 (PCR Analysis). Multiplexed immunoassays such as those available from Rules Based Medicine or Meso Scale Discovery ("MSD") may also be used.

In any of the preceding methods, the presence and/or expression level/amount of a biomarker (e.g., PD-L1) is measured by determining protein expression levels of the biomarker. In certain instances, the method comprises contacting the biological sample with antibodies that specifically bind to a biomarker (e.g., anti-PD-L1 antibodies) described herein under conditions permissive for binding of the biomarker, and detecting whether a complex is formed between the antibodies and biomarker. Such method may be an in vitro or in vivo method. In some instances, an antibody is used to select subjects eligible for therapy with a PD-L1 axis binding antagonist (e.g., a biomarker for selection of individuals). Any method of measuring protein expression levels known in the art or provided herein may be used. For example, in some instances, a protein expression level of a biomarker (e.g., PD-L1) is determined using a method selected from the group consisting of flow cytometry (e.g., fluorescence-activated cell sorting (FACS™)), Western blot, enzyme-linked immunosorbent assay (ELISA), immunoprecipitation, immunohistochemistry (IHC), immunofluorescence, radioimmunoassay, dot blotting, immunodetection methods, HPLC, surface plasmon resonance, optical spectroscopy, mass spectrometry, and HPLC. In some instances, the protein expression level of the biomarker (e.g., PD-L1) is determined in tumor-infiltrating immune cells. In some instances, the protein expression level of the biomarker (e.g., PD-L1) is determined in tumor cells. In some instances, the protein expression level of the biomarker (e.g., PD-L1) is determined in tumor-infiltrating immune cells and/or in tumor cells.

In certain instances, the presence and/or expression level/amount of a biomarker protein (e.g., PD-L1) in a sample is examined using IHC and staining protocols. IHC staining of tissue sections has been shown to be a reliable method of determining or detecting the presence of proteins in a sample. In some instances of any of the methods, assays and/or kits, the biomarker is PD-L1. In one instance, expression level of biomarker is determined using a method comprising: (a) performing IHC analysis of a sample (such as a tumor sample obtained from a patient) with an antibody; and (b) determining expression level of a biomarker in the sample. In some instances, IHC staining intensity is determined relative to a reference. In some instances, the reference is a reference value. In some instances, the reference is a reference sample (e.g., a control cell line staining sample, a tissue sample from non-cancerous patient, or a PD-L1-negative tumor sample).

IHC may be performed in combination with additional techniques such as morphological staining and/or in situ hybridization (e.g., FISH). Two general methods of IHC are available; direct and indirect assays.

According to the first assay, binding of antibody to the target antigen is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for IHC typically will be labeled with a detectable moiety. Numerous labels are available which can be generally grouped into the following categories: (a) radioisotopes, such as $^{35}S$, $^{14}C$, $^{125}I$, $^{3}H$, and $^{131}I$; (b) colloidal gold particles; (c) fluorescent labels including, but are not limited to, rare earth chelates (europium chelates), Texas Red, rhodamine, fluorescein, dansyl, lissamine, umbelliferone, phycocrytherin, phycocyanin, or commercially-available fluorophores such as SPECTRUM ORANGE7 and SPECTRUM GREEN7 and/or derivatives of any one or more of the above; (d) various enzyme-substrate labels are available and U.S. Pat. No. 4,275,149 provides a review of some of these. Examples of enzymatic labels include luciferases (e.g., firefly luciferase and bacterial luciferase; see, e.g., U.S. Pat. No. 4,737,456), luciferin, 2,3-dihydrophthalazinediones, malate dehydrogenase, urease, peroxidase such as horseradish peroxidase (HRPO), alkaline phosphatase, P-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

Examples of enzyme-substrate combinations include, for example, horseradish peroxidase (HRPO) with hydrogen peroxidase as a substrate; alkaline phosphatase (AP) with para-Nitrophenyl phosphate as chromogenic substrate; and β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase). For a general review of these, see, for example, U.S. Pat. Nos. 4,275,149 and 4,318,980.

Specimens may be prepared, for example, manually, or using an automated staining instrument (e.g., a Ventana BENCHMARK XT™ automated staining instrument or BENCHMARK ULTRA™ automated staining instrument; see, e.g., Example 1 below). Specimens thus prepared may be mounted and coverslipped. Slide evaluation is then determined, for example, using a microscope, and staining intensity criteria, routinely used in the art, may be employed. In one instance, it is to be understood that when cells and/or tissue from a tumor is examined using IHC, staining is generally determined or assessed in tumor cell(s) and/or tissue (as opposed to stromal or surrounding tissue that may be present in the sample). In some instances, it is understood that when cells and/or tissue from a tumor is examined using IHC, staining includes determining or assessing in tumor-infiltrating immune cells, including intratumoral or peritumoral immune cells. In some instances, the presence of a biomarker (e.g., PD-L1) is detected by IHC in >0% of the sample, in at least 1% of the sample, in at least 5% of the sample, in at least 10% of the sample, in at least 15% of the sample, in at least 15% of the sample, in at least 20% of the sample, in at least 25% of the sample, in at least 30% of the sample, in at least 35% of the sample, in at least 40% of the sample, in at least 45% of the sample, in at least 50% of the sample, in at least 55% of the sample, in at least 60% of the sample, in at least 65% of the sample, in at least 70% of the sample, in at least 75% of the sample, in at least 80% of the sample, in at least 85% of the sample, in at least 90% of the sample, in at least 95% of the sample, or more. Samples may be scored using any of the criteria described herein (see, e.g., Table 2), for example, by a pathologist or automated image analysis.

In some instances of any of the methods described herein, PD-L1 is detected by immunohistochemistry using an anti-PD-L1 diagnostic antibody. In some instances, the PD-L1 diagnostic antibody specifically binds human PD-L1. In some instances, the PD-L1 diagnostic antibody is a non-human antibody. In some instances, the PD-L1 diagnostic antibody is a rat, mouse, or rabbit antibody. In some instances, the PD-L1 diagnostic antibody is a rabbit antibody. In some instances, the PD-L1 diagnostic antibody is a monoclonal antibody. In some instances, the PD-L1 diagnostic antibody is directly labeled. In other instances, the PD-L1 diagnostic antibody is indirectly labeled.

In some instances of any of the preceding methods, the expression level of PD-L1 is detected in tumor-infiltrating immune cells, tumor cells, or combinations thereof using IHC. Tumor-infiltrating immune cells include, but are not limited to, intratumoral immune cells, peritumoral immune cells or any combinations thereof, and other tumor stroma cells (e.g., fibroblasts). Such tumor infiltrating immune cells may be T lymphocytes (such as CD8+T lymphocytes and/or CD4+T lymphocytes), B lymphocytes, or other bone marrow-lineage cells including granulocytes (neutrophils, eosinophils, basophils), monocytes, macrophages, dendritic cells (e.g., interdigitating dendritic cells), histiocytes, and natural killer cells. In some instances, the staining for PD-L1 is detected as membrane staining, cytoplasmic staining and combinations thereof. In other instances, the absence of PD-L1 is detected as absent or no staining in the sample.

In any of the preceding methods, the expression level of a biomarker (e.g., PD-L1) may be a nucleic acid expression level. In some instances, the nucleic acid expression level is determined using qPCR, rtPCR, RNA-seq, multiplex qPCR or RT-qPCR, microarray analysis, SAGE, MassARRAY technique, or in situ hybridization (e.g., FISH). In some instances, the expression level of a biomarker (e.g., PD-L1) is determined in tumor cells, tumor infiltrating immune cells, stromal cells, or combinations thereof. In some instances, the expression level of a biomarker (e.g., PD-L1) is determined in tumor-infiltrating immune cells. In some instances, the expression level of a biomarker (e.g., PD-L1) is determined in tumor cells.

Methods for the evaluation of mRNAs in cells are well known and include, for example, hybridization assays using complementary DNA probes (such as in situ hybridization using labeled riboprobes specific for the one or more genes, Northern blot and related techniques) and various nucleic acid amplification assays (such as RT-PCR using complementary primers specific for one or more of the genes, and other amplification type detection methods, such as, for example, branched DNA, SISBA, TMA and the like). In addition, such methods can include one or more steps that allow one to determine the levels of target mRNA in a biological sample (e.g., by simultaneously examining the levels a comparative control mRNA sequence of a "housekeeping" gene such as an actin family member). Optionally, the sequence of the amplified target cDNA can be determined. Optional methods include protocols which examine or detect mRNAs, such as target mRNAs, in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support.

The array is configured such that the sequence and position of each member of the array is known. For example, a selection of genes whose expression correlates with increased or reduced clinical benefit of treatment comprising a PD-L1 axis binding antagonist may be arrayed on a solid support. Hybridization of a labeled probe with a particular array member indicates that the sample from which the probe was derived expresses that gene.

In certain instances, the presence and/or expression levels/amount of a biomarker in a first sample is increased or elevated as compared to presence/absence and/or expression levels/amount in a second sample. In certain instances, the presence/absence and/or expression levels/amount of a biomarker in a first sample is decreased or reduced as compared to presence and/or expression levels/amount in a second sample. In certain instances, the second sample is a reference sample, reference cell, reference tissue, control sample, control cell, or control tissue. Additional disclosures for determining the presence/absence and/or expression levels/amount of a gene are described herein.

In certain instances, a reference sample, reference cell, reference tissue, control sample, control cell, or control tissue is a single sample or a combination of multiple samples from the same subject or individual that are obtained at one or more different time points than when the test sample is obtained. For example, a reference sample, reference cell, reference tissue, control sample, control cell, or control tissue is obtained at an earlier time point from the same subject or individual than when the test sample is obtained. Such reference sample, reference cell, reference tissue, control sample, control cell, or control tissue may be useful if the reference sample is obtained during initial diagnosis of cancer and the test sample is later obtained when the cancer becomes metastatic.

In certain embodiments, a reference sample, reference cell, reference tissue, control sample, control cell, or control tissue is a combination of multiple samples from one or more healthy individuals who are not the patient. In certain embodiments, a reference sample, reference cell, reference tissue, control sample, control cell, or control tissue is a combination of multiple samples from one or more individuals with a disease or disorder (e.g., cancer) who are not the subject or individual. In certain embodiments, a reference sample, reference cell, reference tissue, control sample, control cell, or control tissue is pooled RNA samples from normal tissues or pooled plasma or serum samples from one or more individuals who are not the patient. In certain embodiments, a reference sample, reference cell, reference tissue, control sample, control cell, or control tissue is pooled RNA samples from tumor tissues or pooled plasma or serum samples from one or more individuals with a disease or disorder (e.g., cancer) who are not the patient.

In some embodiments of any of the methods, elevated or increased expression refers to an overall increase of about any of 10%, 20%, 30%, 40%, 50%, 60%, 70%, 80%, 90%, 95%, 96%, 97%, 98%, 99% or greater, in the level of biomarker (e.g., protein or nucleic acid (e.g., gene or mRNA)), detected by standard art-known methods such as those described herein, as compared to a reference sample, reference cell, reference tissue, control sample, control cell, or control tissue. In certain embodiments, the elevated expression refers to the increase in expression level/amount of a biomarker in the sample wherein the increase is at least about any of 1.5×, 1.75×, 2×, 3×, 4×, 5×, 6×, 7×, 8×, 9×, 10×, 25×, 50×, 75×, or 100× the expression level/amount of the respective biomarker in a reference sample, reference cell, reference tissue, control sample, control cell, or control tissue. In some embodiments, elevated expression refers to an overall increase of greater than about 1.5-fold, about 1.75-fold, about 2-fold, about 2.25-fold, about 2.5-fold, about 2.75-fold, about 3.0-fold, or about 3.25-fold as compared to a reference sample, reference cell, reference tissue, control sample, control cell, control tissue, or internal control (e.g., housekeeping gene).

In some embodiments of any of the methods, reduced expression refers to an overall reduction of about any of 10%, 20%, 30%, 40%, 50%, 60%, 70%, 80%, 90%, 95%, 96%, 97%, 98%, 99% or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue. In certain embodiments, reduced expression refers to the decrease in expression level/amount of a biomarker in the sample wherein the decrease is at least about any of 0.9×, 0.8×, 0.7×, 0.6×, 0.5×, 0.4×, 0.3×, 0.2×, 0.1×, 0.05×, or 0.01× the expression level/amount of the respective biomarker in a reference sample, reference cell, reference tissue, control sample, control cell, or control tissue.

C. Therapeutic Methods The present invention provides methods for treating a patient suffering from a cancer (e.g., a bladder cancer (e.g., an urothelial bladder cancer)). In some instances, the methods of the invention include administering to the patient an anti-cancer therapy that includes a PD-L1 axis binding antagonist. Any of the PD-L1 axis binding antagonists described herein (see, for example, Section D, below) or known in the art may used in the methods. In some instances, the methods involve determining the presence and/or expression level of PD-L1 in a sample (for example, in tumor-infiltrating immune cells in a tumor sample) obtained from a patient and administering an anti-cancer therapy to the patient based on the presence and/or expression level of PD-L1 in the sample, for example, using any of the methods described herein (for example, those described in Section A, Section B, or in the Examples below) or known in the art.

The invention provides a method of treating a patient suffering from a bladder cancer, the method comprising administering to the patient a therapeutically effective amount of a PD-L1 axis binding antagonist, wherein a tumor sample obtained from the patient has been determined to have a detectable expression level of PD-L1 in tumor-infiltrating immune cells that comprise 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, or about 50% or more) of the tumor sample.

The invention further provides a method of treating a patient suffering from a bladder cancer, the method comprising administering to the patient a therapeutically effective amount of a PD-L1 axis binding antagonist, wherein a tumor sample obtained from the patient has been determined to be a luminal subtype tumor. In some instances, the tumor has been determined to be a luminal subtype II tumor.

In any of the preceding methods, the tumor-infiltrating immune cells may cover about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, or about 50% or more) of the tumor area in a section of the tumor sample obtained from the patient. For example, in some instances, the tumor-infiltrating immune cells may cover about 1% or more of the tumor area in a section of the tumor sample. In some instances, the tumor-infiltrating immune cells may cover about 5% or more of the tumor area in a section of the tumor sample. In other instances, the tumor-infiltrating immune cells may cover about 10% or more of the tumor area in a section of the tumor sample. In some instances, the tumor-infiltrating immune cells may cover about 15% or more of the tumor area in a section of the tumor sample. In yet other instances, the tumor-infiltrating immune cells may cover about 20% or more of the tumor area in a section of the tumor sample. In further instances, the tumor-infiltrating immune cells may cover about 25% or more of the tumor area in a section of the tumor sample. In some instances, the tumor-infiltrating immune cells may cover about 30% or more of the tumor area in a section of the tumor sample. In some instances, the tumor-infiltrating immune cells may cover about 35% or more of the tumor area in a section of the tumor sample. In some instances, the tumor-infiltrating immune cells may cover about 40% or more of the tumor area in a section of the tumor sample. In some instances, the tumor-infiltrating immune cells may cover about 50% or more of the tumor area in a section of the tumor sample.

In any of the preceding methods, about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 99% or more) of the tumor-infiltrating immune cells in the tumor sample may express a detectable expression level of PD-L1.

The invention provides a method for treating a patient suffering from a bladder cancer, the method comprising administering to the patient a therapeutically effective amount of a PD-L1 axis binding antagonist, wherein a tumor sample obtained from the patient has been determined to have a detectable expression level of PD-L1 in tumor-infiltrating immune cells that comprise about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, or about 50% or more) of the tumor sample indicates that the patient is likely to respond to treatment comprising a PD-L1 axis binding antagonist. For example, in some instances, a detectable expression level of PD-L1 in tumor-infiltrating immune cells that comprise about 1% or more of the tumor sample indicates that the patient is likely to respond to treatment comprising a PD-L1 axis binding antagonist. In some instances, a detectable expression level of PD-L1 in tumor-infiltrating immune cells that comprise about 5% or more of the tumor sample indicates that the patient is likely to respond to treatment comprising a PD-L1 axis binding antagonist. In other instances, a detectable expression level of PD-L1 in tumor-infiltrating immune cells that comprise about 10% or more of the tumor sample indicates that the patient is likely to respond to treatment comprising a PD-L1 axis binding antagonist.

In some instances, a change in the level of one or more (e.g., 1, 2, 3, 4, 5, 6, 7, 8, 9, 10, 11, 12, 13, 14, 15, or 16) of the biomarkers listed in Table 1 may be used to help determine tumor subtype. In some instances, the tumor sample (e.g., a UBC tumor sample) is a luminal subtype tumor (e.g., a luminal subtype II tumor). The invention provides a method for treating a patient suffering from a bladder cancer, the method comprising administering to the patient a therapeutically effective amount of a PD-L1 axis binding antagonist, wherein a tumor sample obtained from the patient has been determined to be a luminal subtype tumor (e.g., a UBC luminal subtype tumor). In some instances, the tumor has been determined to be a luminal subtype II tumor.

In some instances, the level of expression of at least one or more (e.g., 1, 2, 3, or 4) biomarkers selected from Table 1, Group A (e.g., FGFR3, miR-99a-5p, miR-100-5p, CDKN2A) and at least one or more (e.g., 1, 2, 3, or 4) biomarkers selected from Table 1, Group B (e.g., KRT5, KRT6A, KRT14, EGFR) can be used to determine luminal subtype II classification. In some instances, the level of expression of at least one or more (e.g., 1, 2, 3, or 4) biomarkers selected from Table 1, Group A (e.g., FGFR3, miR-99a-5p, miR-100-5p, CDKN2A) and at least one or more (e.g., 1, 2, 3, 4, 5, or 6) biomarkers selected from Table 1, Group C (e.g., GATA3, FOXA1, UPK3A, miR-200a-3p, miR-200b-3p, E-cadherin) can be used to determine luminal subtype II classification. In some instances, the level of expression of at least one or more (e.g., 1, 2, 3, or 4) biomarkers selected from Table 1, Group A (e.g., FGFR3, miR-99a-5p, miR-100-5p, CDKN2A) and at least one or more (e.g., 1 or 2) biomarkers selected from Table 1, Group D (e.g., ERBB2, ESR2) can be used to determine luminal subtype II classification. In some instances, the level of expression of at least one or more (e.g., 1, 2, 3, or 4) biomarkers selected from Table 1, Group A (e.g., FGFR3, miR-99a-5p, miR-100-5p, CDKN2A); at least one or more (e.g., 1, 2, 3, 4, 5, or 6) biomarkers selected from Table 1, Group C (e.g., GATA3, FOXA1, UPK3A, miR-200a-3p, miR-200b-3p, E-cadherin); and at least one or more (e.g., 1 or 2) biomarkers selected from Table 1, Group D (e.g., ERBB2, ESR2) can be used to determine luminal subtype II classification. In some instances, the level of expression of at least one or more (e.g., 1, 2, 3, or 4) biomarkers selected from Table 1, Group A (e.g., FGFR3, miR-99a-5p, miR-100-5p, CDKN2A); at least one or more (e.g., 1, 2, 3, or 4)

biomarkers selected from Table 1, Group B (e.g., KRT5, KRT6A, KRT14, EGFR); at least one or more (e.g., 1, 2, 3, 4, 5, or 6) biomarkers selected from Table 1, Group C (e.g., GATA3, FOXA1, UPK3A, miR-200a-3p, miR-200b-3p, E-cadherin); and at least one or more (e.g., 1 or 2) biomarkers selected from Table 1, Group D (e.g., ERBB2, ESR2) can be used to determine luminal subtype II classification. In any of the preceding instances the level of a biomarker is an mRNA level, a protein level, and/or a microRNA (e.g., miRNA) level.

In some instances, an increased level of expression of at least one of miR-99a-5p, miR-100-5p, and CDKN2A and/or a decreased level of expression of FGFR3 in combination with a decreased level of expression of at least one of KRT5, KRT6A, KRT14, and EGFR compared to reference levels of the biomarkers can be used to determine luminal subtype II classification. In some instances, an increased level of expression of at least one of miR-99a-5p, miR-100-5p, and CDKN2A and/or a decreased level of expression of FGFR3 in combination with an increased level of at least one of GATA3, FOXA1, UPK3A, miR-200a-3p, miR-200b-3p, and E-cadherin compared to reference levels of the biomarkers can be used to determine luminal subtype II classification. In some instances, an increased level of expression of at least one of miR-99a-5p, miR-100-5p, and CDKN2A and/or a decreased level of expression of FGFR3 in combination with an increased level of ERBB2 and/or ESR2 compared to reference levels of the biomarkers can be used to determine luminal subtype II classification. In some instances, an increased level of expression of at least one of miR-99a-5p, miR-100-5p, and CDKN2A and/or a decreased level of expression of FGFR3; an increased level of at least one of GATA3, FOXA1, UPK3A, miR-200a-3p, miR-200b-3p, and E-cadherin; and an increased level of ERBB2 and/or ESR2 compared to reference levels of the biomarkers can be used to determine luminal subtype II classification. In some instances, an increased level of expression of at least one of miR-99a-5p, miR-100-5p, and CDKN2A and/or a decreased level of expression of FGFR3; a decreased level of expression of at least one of KRT5, KRT6A, KRT14, and EGFR; and an increased level of ERBB2 and/or ESR2 compared to reference levels of the biomarkers can be used to determine luminal subtype II classification. In some instances, an increased level of expression of at least one of miR-99a-5p, miR-100-5p, and CDKN2A and/or a decreased level of expression of FGFR3; a decreased level of expression of at least one of KRT5, KRT6A, KRT14, and EGFR; an increased level of expression of at least one of GATA3, FOXA1, UPK3A, miR-200a-3p, miR-200b-3p, and E-cadherin; and an increased level of ERBB2 and/or ESR2 compared to reference levels of the biomarkers can be used to determine luminal subtype II classification. In any of the preceding instances the level of a biomarker is an mRNA level, a protein level, and/or a miRNA level.

In any of the preceding methods, the PD-L1 axis binding antagonist may be any PD-L1 axis binding antagonist known in the art or described herein, for example, in Section D, below.

For example, in some instances, the PD-L1 axis binding antagonist is selected from the group consisting of a PD-L1 binding antagonist, a PD-1 binding antagonist, and a PD-L2 binding antagonist. In some instances, the PD-L1 axis binding antagonist is a PD-L1 binding antagonist. In some instances, the PD-L1 binding antagonist inhibits the binding of PD-L1 to one or more of its ligand binding partners. In other instances, the PD-L1 binding antagonist inhibits the binding of PD-L1 to PD-1. In yet other instances, the PD-L1 binding antagonist inhibits the binding of PD-L1 to B7-1. In some instances, the PD-L1 binding antagonist inhibits the binding of PD-L1 to both PD-1 and B7-1. In some instances, the PD-L1 binding antagonist is an antibody. In some instances, the antibody is selected from the group consisting of: YW243.55.S70, MPDL3280A (atezolizumab), MDX-1105, MED14736 (durvalumab), and MSB0010718C (avelumab). In some instances, the antibody comprises a heavy chain comprising HVR-H1 sequence of SEQ ID NO:19, HVR-H2 sequence of SEQ ID NO:20, and HVR-H3 sequence of SEQ ID NO:21; and a light chain comprising HVR-L1 sequence of SEQ ID NO:22, HVR-L2 sequence of SEQ ID NO:23, and HVR-L3 sequence of SEQ ID NO:24.

In some instances, the antibody comprises a heavy chain variable region comprising the amino acid sequence of SEQ ID NO:26 and a light chain variable region comprising the amino acid sequence of SEQ ID NO:4.

In some instances, the PD-L1 axis binding antagonist is a PD-1 binding antagonist. For example, in some instances, the PD-1 binding antagonist inhibits the binding of PD-1 to one or more of its ligand binding partners. In some instances, the PD-1 binding antagonist inhibits the binding of PD-1 to PD-L1. In other instances, the PD-1 binding antagonist inhibits the binding of PD-1 to PD-L2. In yet other instances, the PD-1 binding antagonist inhibits the binding of PD-1 to both PD-L1 and PD-L2. In some instances, the PD-1 binding antagonist is an antibody. In some instances, the antibody is selected from the group consisting of: MDX 1106 (nivolumab), MK-3475 (pembrolizumab), CT-011 (pidilizumab), MEDI-0680 (AMP-514), PDR001, REGN2810, and BGB-108. In some instances, the PD-1 binding antagonist is an Fc-fusion protein. For example, in some instances, the Fc-fusion protein is AMP-224.

In some instances, the method further includes administering to the patient an effective amount of a second therapeutic agent. In some instances, the second therapeutic agent is selected from the group consisting of a cytotoxic agent, a growth-inhibitory agent, a radiation therapy agent, an anti-angiogenic agent, and combinations thereof. In some instances, the second therapeutic agent is an agonist directed against an activating co-stimulatory molecule. In some instances, the second therapeutic agent is an antagonist directed against an inhibitory co-stimulatory molecule.

In any of the preceding instances, the urothelial bladder cancer may be, for example, a non-muscle invasive urothelial bladder cancer, a muscle-invasive urothelial bladder cancer, or metastatic urothelial bladder cancer.

In a further aspect, the invention provides for the use of a PD-L1 axis binding antagonist in the manufacture or preparation of a medicament. In one instance, the medicament is for treatment of a cancer.

In a further instance, the medicament is for use in a method of treating a cancer comprising administering to a patient suffering from a cancer (e.g., a bladder cancer (e.g., an urothelial bladder cancer)) an effective amount of the medicament. In one such instance, the method further comprises administering to the individual an effective amount of at least one additional therapeutic agent, e.g., as described below.

The compositions utilized in the methods described herein (e.g., PD-L1 axis binding antagonists) can be administered by any suitable method, including, for example, intravenously, intramuscularly, subcutaneously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subconjunctivally, intravesicularly, mucosally, intrapericardially, intraumbilically, intraocularly, intraorbitally, orally, topically, transdermally, intravitreally (e.g., by intravitreal injection), by eye drop, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered and the severity of the condition, disease, or disorder being treated). In some instances, the PD-L1 axis binding antagonist is administered intravenously, intramuscularly, subcutaneously, topically, orally, transdermally, intraperitoneally, intraorbitally, by implantation, by inhalation, intrathecally, intraventricularly, or intranasally. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

PD-L1 axis binding antagonists (e.g., an antibody, binding polypeptide, and/or small molecule) described herein (any additional therapeutic agent) may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The PD-L1 axis binding antagonist need not be, but is optionally formulated with and/or administered concurrently with one or more agents currently used to prevent or treat the disorder in question. The effective amount of such other agents depends on the amount of the PD-L1 axis binding antagonist present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of a cancer (e.g., a bladder cancer (e.g., an urothelial bladder cancer)), the appropriate dosage of a PD-L1 axis binding antagonist described herein (when used alone or in combination with one or more other additional therapeutic agents) will depend on the type of disease to be treated, the severity and course of the disease, whether the PD-L1 axis binding antagonist is administered for preventive or therapeutic purposes, previous therapy, the patient's clinical history and response to the PD-L1 axis binding antagonist, and the discretion of the attending physician. The PD-L1 axis binding antagonist is suitably administered to the patient at one time or over a series of treatments. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. Such doses may be administered intermittently, e.g., every week or every three weeks (e.g., such that the patient receives, for example, from about two to about twenty, or e.g., about six doses of the PD-L1 axis binding antagonist). An initial higher loading dose, followed by one or more lower doses may be administered. However, other dosage regimens may be useful. The progress of this therapy is easily monitored by conventional techniques and assays.

For example, as a general proposition, the therapeutically effective amount of a PD-L1 axis binding antagonist antibody administered to human will be in the range of about 0.01 to about 50 mg/kg of patient body weight, whether by one or more administrations. In some instances, the antibody used is about 0.01 mg/kg to about 45 mg/kg, about 0.01 mg/kg to about 40 mg/kg, about 0.01 mg/kg to about 35 mg/kg, about 0.01 mg/kg to about 30 mg/kg, about 0.01 mg/kg to about 25 mg/kg, about 0.01 mg/kg to about 20 mg/kg, about 0.01 mg/kg to about 15 mg/kg, about 0.01 mg/kg to about 10 mg/kg, about 0.01 mg/kg to about 5 mg/kg, or about 0.01 mg/kg to about 1 mg/kg administered daily, weekly, every two weeks, every three weeks, or monthly, for example. In some instances, the antibody is administered at 15 mg/kg. However, other dosage regimens may be useful. In one instance, an anti-PD-L1 antibody described herein is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, or about 1800 mg on day 1 of 21-day cycles (every three weeks, q3w). In some instances, anti-PD-L1 antibody MPDL3280A is administered at 1200 mg intravenously every three weeks (q3w). The dose may be administered as a single dose or as multiple doses (e.g., 2 or 3 doses), such as infusions. The dose of the antibody administered in a combination treatment may be reduced as compared to a single treatment. The progress of this therapy is easily monitored by conventional techniques.

In some instances, the methods further involve administering to the patient an effective amount of a second therapeutic agent. In some instances, the second therapeutic agent is selected from the group consisting of a cytotoxic agent, a chemotherapeutic agent, a growth-inhibitory agent, a radiation therapy agent, an anti-angiogenic agent, and combinations thereof. In some instances, a PD-L1 axis binding antagonist may be administered in conjunction with a chemotherapy or chemotherapeutic agent. In some instances, a PD-L1 axis binding antagonist may be administered in conjunction with a radiation therapy agent. In some instances, a PD-L1 axis binding antagonist may be administered in conjunction with a targeted therapy or targeted therapeutic agent. In some instances, a PD-L1 axis binding antagonist may be administered in conjunction with an immunotherapy or immunotherapeutic agent, for example a monoclonal antibody. In some instances, the second therapeutic agent is an agonist directed against an activating co-stimulatory molecule. In some instances, the second therapeutic agent is an antagonist directed against an inhibitory co-stimulatory molecule.

Such combination therapies noted above encompass combined administration (where two or more therapeutic agents are included in the same or separate formulations), and separate administration, in which case, administration of a PD-L1 axis binding antagonist can occur prior to, simultaneously, and/or following, administration of the additional therapeutic agent or agents. In one instance, administration of PD-L1 axis binding antagonist and administration of an additional therapeutic agent occur within about one month, or within about one, two or three weeks, or within about one, two, three, four, five, or six days, of each other.

Without wishing to be bound to theory, it is thought that enhancing T-cell stimulation, by promoting an activating co-stimulatory molecule or by inhibiting a negative co-stimulatory molecule, may promote tumor cell death thereby treating or delaying progression of cancer. In some instances, a PD-L1 axis binding antagonist may be administered in conjunction with an agonist directed against an activating co-stimulatory molecule. In some instances, an activating co-stimulatory molecule may include CD40, CD226, CD28, OX40, GITR, CD137, CD27, HVEM, or CD127. In some instances, the agonist directed against an activating co-stimulatory molecule is an agonist antibody that binds to CD40, CD226, CD28, OX40, GITR, CD137, CD27, HVEM, or CD127. In some instances, a PD-L1 axis binding antagonist may be administered in conjunction with an antagonist directed against an inhibitory co-stimulatory molecule. In some instances, an inhibitory co-stimulatory molecule may include CTLA-4 (also known as CD152), TIM-3, BTLA, VISTA, LAG-3, B7-H3, B7-H4, IDO, TIGIT, MICA/B, or arginase. In some instances, the antagonist directed against an inhibitory co-stimulatory molecule is an antagonist antibody that binds to CTLA-4, TIM-3, BTLA, VISTA, LAG-3, B7-H3, B7-H4, IDO, TIGIT, MICA/B, or arginase.

In some instances, a PD-L1 axis binding antagonist may be administered in conjunction with an antagonist directed against CTLA-4 (also known as CD152), e.g., a blocking antibody. In some instances, a PD-L1 axis binding antagonist may be administered in conjunction with ipilimumab (also known as MDX-010, MDX-101, or YERVOY®). In some instances, a PD-L1 axis binding antagonist may be administered in conjunction with tremelimumab (also known as ticilimumab or CP-675,206). In some instances, a PD-L1 axis binding antagonist may be administered in conjunction with an antagonist directed against B7-H3 (also known as CD276), e.g., a blocking antibody. In some instances, a PD-L1 axis binding antagonist may be administered in conjunction with MGA271. In some instances, a PD-L1 axis binding antagonist may be administered in conjunction with an antagonist directed against a TGF-beta, e.g., metelimumab (also known as CAT-192), fresolimumab (also known as GC1008), or LY2157299.

In some instances, a PD-L1 axis binding antagonist may be administered in conjunction with a treatment comprising adoptive transfer of a T-cell (e.g., a cytotoxic T-cell or CTL) expressing a chimeric antigen receptor (CAR). In some instances, a PD-L1 axis binding antagonist may be administered in conjunction with a treatment comprising adoptive transfer of a T-cell comprising a dominant-negative TGF beta receptor, e.g., a dominant-negative TGF beta type II receptor. In some instances, a PD-L1 axis binding antagonist may be administered in conjunction with a treatment comprising a HERCREEM protocol (see, e.g., ClinicalTrials.gov Identifier NCT00889954).

In some instances, a PD-L1 axis binding antagonist may be administered in conjunction with an agonist directed against CD137 (also known as TNFRSF9, 4-1BB, or ILA), e.g., an activating antibody. In some instances, a PD-L1 axis binding antagonist may be administered in conjunction with urelumab (also known as BMS-663513). In some instances, a PD-L1 axis binding antagonist may be administered in conjunction with an agonist directed against CD40, e.g., an activating antibody. In some instances, a PD-L1 axis binding antagonist may be administered in conjunction with CP-870893. In some instances, a PD-L1 axis binding antagonist may be administered in conjunction with an agonist directed against OX40 (also known as CD134), e.g., an activating antibody. In some instances, a PD-L1 axis binding antagonist may be administered in conjunction with an anti-OX40 antibody (e.g., AgonOX). In some instances, a PD-L1 axis binding antagonist may be administered in conjunction with an agonist directed against CD27, e.g., an activating antibody. In some instances, a PD-L1 axis binding antagonist may be administered in conjunction with CDX-1127. In some instances, a PD-L1 axis binding antagonist may be administered in conjunction with an antagonist directed against indoleamine-2,3-dioxygenase (IDO). In some instances, with the IDO antagonist is 1-methyl-D-tryptophan (also known as 1-D-MT).

In some instances, a PD-L1 axis binding antagonist may be administered in conjunction with an antibody-drug conjugate. In some instances, the antibody-drug conjugate comprises mertansine or monomethyl auristatin E (MMAE). In some instances, a PD-L1 axis binding antagonist may be administered in conjunction with an anti-*NaPi*2b antibody-MMAE conjugate (also known as DNIB0600A or RG7599). In some instances, a PD-L1 axis binding antagonist may be administered in conjunction with trastuzumab emtansine (also known as T-DM1, ado-trastuzumab emtansine, or KADCYLA®, Genentech). In some instances, a PD-L1 axis binding antagonist may be administered in conjunction with DMUC5754A. In some instances, a PD-L1 axis binding antagonist may be administered in conjunction with an antibody-drug conjugate targeting the endothelin B receptor (EDNBR), e.g., an antibody directed against EDNBR conjugated with MMAE.

In some instances, a PD-L1 axis binding antagonist may be administered in conjunction with an anti-angiogenesis agent. In some instances, a PD-L1 axis binding antagonist may be administered in conjunction with an antibody directed against a VEGF, e.g., VEGF-A. In some instances, a PD-L1 axis binding antagonist may be administered in conjunction with bevacizumab (also known as AVASTIN®, Genentech).

In some instances, a PD-L1 axis binding antagonist may be administered in conjunction with an antibody directed against angiopoietin 2 (also known as Ang2). In some instances, a PD-L1 axis binding antagonist may be administered in conjunction with MEDI3617.

In some instances, a PD-L1 axis binding antagonist may be administered in conjunction with an antineoplastic agent. In some instances, a PD-L1 axis binding antagonist may be administered in conjunction with an agent targeting CSF-1R (also known as M-CSFR or CD115). In some instances, a PD-L1 axis binding antagonist may be administered in conjunction with anti-CSF-1R (also known as IMC-CS4). In some instances, a PD-L1 axis binding antagonist may be administered in conjunction with an interferon, for example interferon alpha or interferon gamma. In some instances, a PD-L1 axis binding antagonist may be administered in conjunction with Roferon-A (also known as recombinant Interferon alpha-2a). In some instances, a PD-L1 axis binding antagonist may be administered in conjunction with GM-CSF (also known as recombinant human granulocyte macrophage colony stimulating factor, rhu GM-CSF, sargramostim, or LEUKINE®). In some instances, a PD-L1 axis binding antagonist may be administered in conjunction with IL-2 (also known as aldesleukin or PROLEUKIN®). In some instances, a PD-L1 axis binding antagonist may be administered in conjunction with IL-12. In some instances, a PD-L1 axis binding antagonist may be administered in conjunction with an antibody targeting CD20. In some instances, the antibody targeting CD20 is obinutuzumab (also known as GA101 or GAZYVA®) or rituximab. In some instances, a PD-L1 axis binding antagonist may be administered in conjunction with an antibody targeting GITR. In some instances, the antibody targeting GITR is TRX518.

In some instances, a PD-L1 axis binding antagonist may be administered in conjunction with a cancer vaccine. In some instances, the cancer vaccine is a peptide cancer vaccine, which in some instances is a personalized peptide vaccine. In some instances the peptide cancer vaccine is a multivalent long peptide, a multi-peptide, a peptide cocktail, a hybrid peptide, or a peptide-pulsed dendritic cell vaccine (see, e.g., Yamada et al., Cancer Sci. 104:14-21, 2013). In some instances, a PD-L1 axis binding antagonist may be administered in conjunction with an adjuvant. In some instances, a PD-L1 axis binding antagonist may be administered in conjunction with a treatment comprising a TLR agonist, e.g., Poly-ICLC (also known as HILTONOL®), LPS, MPL, or CpG ODN. In some instances, a PD-L1 axis binding antagonist may be administered in conjunction with tumor necrosis factor (TNF) alpha. In some instances, a PD-L1 axis binding antagonist may be administered in conjunction with IL-1. In some instances, a PD-L1 axis binding antagonist may be administered in conjunction with HMGB1. In some instances, a PD-L1 axis binding antagonist may be administered in conjunction with an IL-10 antagonist. In some instances, a PD-L1 axis binding antagonist may be administered in conjunction with an IL-4 antagonist. In some instances, a PD-L1 axis binding antagonist may be administered in conjunction with an IL-13 antagonist. In some instances, a PD-L1 axis binding antagonist may be administered in conjunction with an HVEM antagonist. In some instances, a PD-L1 axis binding antagonist may be administered in conjunction with an ICOS agonist, e.g., by administration of ICOS-L, or an agonistic antibody directed against ICOS. In some instances, a PD-L1 axis binding antagonist may be administered in conjunction with a treatment targeting CX3CL1. In some instances, a PD-L1 axis binding antagonist may be administered in conjunction with a treatment targeting CXCL9. In some instances, a PD-L1 axis binding antagonist may be administered in conjunction with a treatment targeting CXCL10. In some instances, a PD-L1 axis binding antagonist may be administered in conjunction with a treatment targeting CCL5. In some instances, a PD-L1 axis binding antagonist may be administered in conjunction with an LFA-1 or ICAM1 agonist. In some instances, a PD-L1 axis binding antagonist may be administered in conjunction with a Selectin agonist.

In some instances, a PD-L1 axis binding antagonist may be administered in conjunction with a targeted therapy. In some instances, a PD-L1 axis binding antagonist may be administered in conjunction with an inhibitor of B-Raf. In some instances, a PD-L1 axis binding antagonist may be administered in conjunction with vemurafenib (also known as ZELBORAF®). In some instances, a PD-L1 axis binding antagonist may be administered in conjunction with dabrafenib (also known as TAFINLAR®). In some instances, a PD-L1 axis binding antagonist may be administered in conjunction with erlotinib (also known as TARCEVA®). In some instances, a PD-L1 axis binding antagonist may be administered in conjunction with an inhibitor of a MEK, such as MEK1 (also known as MAP2K1) or MEK2 (also known as MAP2K2). In some instances, a PD-L1 axis binding antagonist may be administered in conjunction with cobimetinib (also known as GDC-0973 or XL-518). In some instances, a PD-L1 axis binding antagonist may be administered in conjunction with trametinib (also known as MEKINIST®). In some instances, a PD-L1 axis binding antagonist may be administered in conjunction with an inhibitor of K-Ras. In some instances, a PD-L1 axis binding antagonist may be administered in conjunction with an inhibitor of c-Met. In some instances, a PD-L1 axis binding antagonist may be administered in conjunction with onartuzumab (also known as MetMAb). In some instances, a PD-L1 axis binding antagonist may be administered in conjunction with an inhibitor of Alk. In some instances, a PD-L1 axis binding antagonist may be administered in conjunction with AF802 (also known as CH5424802 or alectinib). In some instances, a PD-L1 axis binding antagonist may be administered in conjunction with an inhibitor of a phosphatidylinositol 3-kinase (PI3K). In some instances, a PD-L1 axis binding antagonist may be administered in conjunction with BKM120. In some instances, a PD-L1 axis binding antagonist may be administered in conjunction with idelalisib (also known as GS-1101 or CAL-101).

In some embodiments, a PD-L1 axis binding antagonist may be administered in conjunction with perifosine (also known as KRX-0401). In some embodiments, a PD-L1 axis binding antagonist may be administered in conjunction with an inhibitor of an Akt. In some embodiments, a PD-L1 axis binding antagonist may be administered in conjunction with MK2206. In some instances, a PD-L1 axis binding antagonist may be administered in conjunction with GSK690693. In some instances, a PD-L1 axis binding antagonist may be administered in conjunction with GDC-0941. In some instances, a PD-L1 axis binding antagonist may be administered in conjunction with an inhibitor of mTOR. In some instances, a PD-L1 axis binding antagonist may be administered in conjunction with sirolimus (also known as rapamycin). In some instances, a PD-L1 axis binding antagonist may be administered in conjunction with temsirolimus (also known as CCI-779 or TORISEL®). In some instances, a PD-L1 axis binding antagonist may be administered in conjunction with everolimus (also known as RAD001). In some instances, a PD-L1 axis binding antagonist may be administered in conjunction with ridaforolimus (also known as AP-23573, MK-8669, or deforolimus). In some instances, a PD-L1 axis binding antagonist may be administered in conjunction with OSI-027. In some instances, a PD-L1 axis binding antagonist may be administered in conjunction with AZD8055. In some instances, a PD-L1 axis binding antagonist may be administered in conjunction with INK128. In some instances, a PD-L1 axis binding antagonist may be administered in conjunction with a dual PI3K/mTOR inhibitor. In some instances, a PD-L1 axis binding antagonist may be administered in conjunction with XL765. In some instances, a PD-L1 axis binding antagonist may be administered in conjunction with GDC-0980. In some instances, a PD-L1 axis binding antagonist may be administered in conjunction with BEZ235 (also known as NVP-BEZ235). In some instances, a PD-L1 axis binding antagonist may be administered in conjunction with BGT226. In some instances, a PD-L1 axis binding antagonist may be administered in conjunction with GSK2126458. In some instances, a PD-L1 axis binding antagonist may be administered in conjunction with PF-04691502. In some instances, a PD-L1 axis binding antagonist may be administered in conjunction with PF-05212384 (also known as PKI-587).

D. PD-L1 Axis Binding Antagonists for Use in the Methods of the Invention

Provided herein are methods for treating or delaying progression of a cancer (e.g., a bladder cancer (e.g., an urothelial bladder cancer)) in a patient comprising administering to the patient a therapeutically effective amount of a PD-L1 axis binding antagonist. Provided herein are methods for determining whether a patient suffering from a cancer (e.g., a bladder cancer (e.g., an urothelial bladder cancer)) is likely to respond to treatment comprising a PD-L1 axis binding antagonist. Provided herein are methods for predicting responsiveness of a patient suffering from a cancer (e.g., a bladder cancer (e.g., an urothelial bladder cancer)) to treatment comprising a PD-L1 axis binding antagonist. Provided herein are methods for selecting a therapy for a patient suffering from a cancer (e.g., a bladder cancer (e.g., an urothelial bladder cancer)).

Any of the preceding methods may be based on the expression level of a biomarker provided herein, for example, PD-L1 expression in a tumor sample, e.g., in tumor-infiltrating immune cells.

For example, a PD-L1 axis binding antagonist includes a PD-1 binding antagonist, a PD-L1 binding antagonist, and a PD-L2 binding antagonist. PD-1 (programmed death 1) is also referred to in the art as "programmed cell death 1," "PDCD1," "CD279," and "SLEB2." An exemplary human PD-1 is shown in UniProtKB/Swiss-Prot Accession No. Q15116. PD-L1 (programmed death ligand 1) is also referred to in the art as "programmed cell death 1 ligand 1," "PDCD1 LG1," "CD274," "B7-H," and "PDL1." An exemplary human PD-L1 is shown in UniProtKB/Swiss-Prot Accession No. Q9NZQ7.1. PD-L2 (programmed death ligand 2) is also referred to in the art as "programmed cell death 1 ligand 2," "PDCD1 LG2," "CD273," "B7-DC," "Btdc," and "PDL2." An exemplary human PD-L2 is shown in UniProtKB/Swiss-Prot Accession No. Q9BQ51. In some instances, PD-1, PD-L1, and PD-L2 are human PD-1, PD-L1 and PD-L2.

In some instances, the PD-1 binding antagonist is a molecule that inhibits the binding of PD-1 to its ligand binding partners. In a specific aspect the PD-1 ligand binding partners are PD-L1 and/or PD-L2. In another instance, a PD-L1 binding antagonist is a molecule that inhibits the binding of PD-L1 to its binding ligands. In a specific aspect, PD-L1 binding partners are PD-1 and/or B7-1. In another instance, the PD-L2 binding antagonist is a molecule that inhibits the binding of PD-L2 to its ligand binding partners. In a specific aspect, the PD-L2 binding ligand partner is PD-1. The antagonist may be an antibody, an antigen binding fragment thereof, an immunoadhesin, a fusion protein, or oligopeptide.

In some instances, the PD-1 binding antagonist is an anti-PD-1 antibody (e.g., a human antibody, a humanized antibody, or a chimeric antibody), for example, as described below. In some instances, the anti-PD-1 antibody is selected from the group consisting of MDX-1106 (nivolumab), MK-3475 (pembrolizumab), CT-011 (pidilizumab), MEDI-0680 (AMP-514), PDR001, REGN2810, and BGB-108. MDX-1106, also known as MDX-1106-04, ONO-4538, BMS-936558, or nivolumab, is an anti-PD-1 antibody described in WO2006/121168. MK-3475, also known as pembrolizumab or lambrolizumab, is an anti-PD-1 antibody described in WO 2009/114335. CT-011, also known as hBAT, hBAT-1 or pidilizumab, is an anti-PD-1 antibody described in WO 2009/101611. In some instances, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In some instances, the PD-1 binding antagonist is AMP-224. AMP-224, also known as B7-DCIg, is a PD-L2-Fc fusion soluble receptor described in WO 2010/027827 and WO 2011/066342.

In some instances, the anti-PD-1 antibody is MDX-1106. Alternative names for "MDX-1106" include MDX-1106-04, ONO-4538, BMS-936558, and nivolumab. In some instances, the anti-PD-1 antibody is nivolumab (CAS Registry Number: 946414-94-4). In a still further instance, provided is an isolated anti-PD-1 antibody comprising a heavy chain variable region comprising the heavy chain variable region amino acid sequence from SEQ ID NO:1 and/or a light chain variable region comprising the light chain variable region amino acid sequence from SEQ ID NO:2. In a still further instance, provided is an isolated anti-PD-1 antibody comprising a heavy chain and/or a light chain sequence, wherein:

(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence:
QVQLVESGGGVVQPGRSLRLDCK-ASGITFSNSGMHWVRQAPGKGLEWVAVIWYDG-SKRYYADSVKGRFTI SRDNSKNTLFLQMNSLRAED-TAVYYCATNDDYWGQGTLVTVSSASTKGPSVFPLAP CSRSTSESTAALGCL VKDYFPEPVTVSWNSGALT-SGVHTFPAVLQSSGLYS-LSSVVTVPSSSLGTKTYTCNVDHKPSNTKVDKRVES KYGPPCPPCPAPEFLGGPSVFLFPPKPKDTLMISRTPE-VTCVVVDVSQEDPEVQFNWYVDGVEVHNAKTKP REEQFN-STYRVVSVLTVLHQDWLNGKEYKCKVSNKGLPSSIE KTISKAKGQPREPQVYTLPPSQEEMTKNQV SLT-CLVKGFYPSDIAVEWESNGQPEN-NYKTTPPVLDSDGSFFLY-SRLTVDKSRWQEGNVFSCSVMHEALHN HYTQKSLSLSLGK (SEQ ID NO:1), and (b) the light chain sequences has at least 85%, at least 90%, at least 91%, at least 92%, at least 93%, at least 94%, at least 95%, at least 96%, at least 97%, at least 98%, at least 99% or 100% sequence identity to the light chain sequence:

```
                                              (SEQ ID NO: 2)
EIVLTQSPATLSLSPGERATLSCRASQSVSSYLAWYQQKPGQAPRLL

IYDASNRATGIPARFSGSGSGTDFTLTISSLEPEDFAVYYCQQSSNW

PRTFGQGTKVEIKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC.
```

In some instances, the PD-L1 axis binding antagonist is a PD-L2 binding antagonist. In some instances, the PD-L2 binding antagonist is an anti-PD-L2 antibody (e.g., a human antibody, a humanized antibody, or a chimeric antibody). In some instances, the PD-L2 binding antagonist is an immunoadhesin.

In some instances, the PD-L1 binding antagonist is an anti-PD-L1 antibody, for example, as described below. In some instances, the anti-PD-L1 antibody is capable of inhibiting binding between PD-L1 and PD-1 and/or between PD-L1 and B7-1. In some instances, the anti-PD-L1 antibody is a monoclonal antibody. In some instances, the anti-PD-L1 antibody is an antibody fragment selected from the group consisting of Fab, Fab'-SH, Fv, scFv, and (Fab')$_2$ fragments. In some instances, the anti-PD-L1 antibody is a humanized antibody. In some instances, the anti-PD-L1 antibody is a human antibody. In some instances, the anti-PD-L1 antibody is selected from the group consisting of YW243.55.S70, MPDL3280A (atezolizumab), MDX-1105, and MEDI4736 (durvalumab), and MSB0010718C (avelumab). Antibody YW243.55.S70 is an anti-PD-L1 described in WO 2010/077634. MDX-1105, also known as BMS-936559, is an anti-PD-L1 antibody described in WO2007/005874. MED14736 (durvalumab) is an anti-PD-L1 monoclonal antibody described in WO2011/066389 and US2013/034559. Examples of anti-PD-L1 antibodies useful for the methods of this invention, and methods for making thereof are described in PCT patent application WO 2010/077634, WO 2007/005874, WO 2011/066389, U.S. Pat. No. 8,217,149, and US 2013/034559, which are incorporated herein by reference.

Anti-PD-L1 antibodies described in WO 2010/077634 A1 and U.S. Pat. No. 8,217,149 may be used in the methods described herein. In some instances, the anti-PD-L1 antibody comprises a heavy chain variable region sequence of SEQ ID NO:3 and/or a light chain variable region sequence of SEQ ID NO:4. In a still further instance, provided is an isolated anti-PD-L1 antibody comprising a heavy chain variable region and/or a light chain variable region sequence, wherein:

(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence: EVQLVESGGGLVQPGGSLRLSCAASGFTFSD- SWIHWVRQAPGKGLEWVAWISPYGGSTYY- ADSVKGRFTIS ADTSKNTAYLQMNSLRAEDTAVYY- CARRHWPGGFDYWGQGTLVTVSA (SEQ ID NO:3), and (b) the light chain sequence has at least 85%, at least 90%, at least 91%, at least 92%, at least 93%, at least 94%, at least 95%, at least 96%, at least 97%, at least 98%, at least 99% or 100% sequence identity to the light chain sequence:

```
                                      (SEQ ID NO: 4)
DIQMTQSPSSLSASVGDRVTITCRASQDVSTAVAWYQQKPGKAPKLL

IYSASFLYSGVPSRFSGSGSGTDFTLTISSLQPEDFATYYCQQYLYH

PATFGQGTKVEIKR.
```

In one instance, the anti-PD-L1 antibody comprises a heavy chain variable region comprising an HVR-H1, HVR-H2 and HVR-H3 sequence, wherein:

```
    (a) the HVR-H1 sequence is
                                       (SEQ ID NO: 5)
    GFTFSX₁SWIH;

(b) the HVR-H2 sequence is
                                       (SEQ ID NO: 6)
    AWIX₂PYGGSX₃YYADSVKG;

(c) the HVR-H3 sequence is
                                       (SEQ ID NO: 7)
    RHWPGGFDY;
``` further wherein: $X_1$ is D or G; $X_2$ is S or L; $X_3$ is T or S. In one specific aspect, $X_1$ is D; $X_2$ is S and $X_3$ is T. In another aspect, the polypeptide further comprises variable region heavy chain framework sequences juxtaposed between the HVRs according to the formula: (FR-H1)-(HVR-H1)-(FR-H2)-(HVR-H2)-(FR-H3)-(HVR-H3)-(FR-H4). In yet another aspect, the framework sequences are derived from human consensus framework sequences. In a further aspect, the framework sequences are VH subgroup III consensus framework. In a still further aspect, at least one of the framework sequences is the following:

```
    FR-H1 is
                                       (SEQ ID NO: 8)
    EVQLVESGGGLVQPGGSLRLSCAAS

FR-H2 is
                                       (SEQ ID NO: 9)
    WVRQAPGKGLEWV

FR-H3 is
                                       (SEQ ID NO: 10)
    RFTISADTSKNTAYLQMNSLRAEDTAVYYCAR

FR-H4 is
                                       (SEQ ID NO: 11)
    WGQGTLVTVSA.
```

In a still further aspect, the heavy chain polypeptide is further combined with a variable region light chain comprising an HVR-L1, HVR-L2 and HVR-L3, wherein:

```
    (a) the HVR-L1 sequence is
                                       (SEQ ID NO: 12)
    RASQX₄X₅X₆TX₇X₈A;

(b) the HVR-L2 sequence is
                                       (SEQ ID NO: 13)
    SASX₉LX₁₀S,;

(c) the HVR-L3 sequence is
                                       (SEQ ID NO: 14)
    QQX₁₁X₁₂X₁₃X₁₄PX₁₅T;
``` wherein: $X_4$ is D or V; $X_5$ is V or I; $X_6$ is S or N; $X_7$ is A or F; $X_8$ is V or L; $X_9$ is F or T; $X_{10}$ is Y or A; $X_{11}$ is Y, G, F, or S; $X_{12}$ is L, Y, F or W; $X_{13}$ is Y, N, A, T, G, F or I; $X_{14}$ is H, V, P, T or I; $X_{15}$ is A, W, R, P or T. In a still further aspect, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H; $X_{15}$ is A.

In a still further aspect, the light chain further comprises variable region light chain framework sequences juxtaposed between the HVRs according to the formula: (FR-L1)-(HVR-L1)-(FR-L2)-(HVR-L2)-(FR-L3)-(HVR-L3)-(FR-L4). In a still further aspect, the framework sequences are derived from human consensus framework sequences. In a still further aspect, the framework sequences are VL kappa I consensus framework. In a still further aspect, at least one of the framework sequence is the following:

```
    FR-L1 is
                                       (SEQ ID NO: 15)
    DIQMTQSPSSLSASVGDRVTITC

FR-L2 is
                                       (SEQ ID NO: 16)
    WYQQKPGKAPKLLIY

FR-L3 is
                                       (SEQ ID NO: 17)
    GVPSRFSGSGSGTDFTLTISSLQPEDFATYYC

FR-L4 is
                                       (SEQ ID NO: 18)
    FGQGTKVEIKR.
```

In another instance, provided is an isolated anti-PD-L1 antibody or antigen binding fragment comprising a heavy chain and a light chain variable region sequence, wherein:

(a) the heavy chain comprises an HVR-H1, HVR-H2 and HVR-H3, wherein further:

(i) the HVR-H1 sequence is
(SEQ ID NO: 5)
GFTFSX₁SWIH;

(ii) the HVR-H2 sequence is
(SEQ ID NO: 6)
AWIX₂PYGGSX₃YYADSVKG (iii) the HVR-H3 sequence is
(SEQ ID NO: 7)
RHWPGGFDY,
and (b) the light chain comprises an HVR-L1, HVR-L2 and HVR-L3, wherein further:

(i) the HVR-L1 sequence is
(SEQ ID NO: 12)
RASQX₄X₅X₆TX₇X₈A (ii) the HVR-L2 sequence is
(SEQ ID NO: 13)
SASX₉LX₁₀S;
and (iii) the HVR-L3 sequence is
(SEQ ID NO: 14)
QQX₁₁X₁₂X₁₃X₁₄PX₁₅T;

wherein: $X_1$ is D or G; $X_2$ is S or L; $X_3$ is T or S; $X_4$ is D or V; $X_5$ is V or I; $X_6$ is S or N; $X_7$ is A or F; $X_8$ is V or L; $X_9$ is F or T; $X_{10}$ is Y or A; $X_{11}$ is Y, G, F, or S; $X_{12}$ is L, Y, F or W; $X_{13}$ is Y, N, A, T, G, F or I; $X_{14}$ is H, V, P, T or I; $X_{15}$ is A, W, R, P or T. In a specific aspect, $X_1$ is D; $X_2$ is S and $X_3$ is T. In another aspect, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H; $X_{15}$ is A. In yet another aspect, $X_1$ is D; $X_2$ is S and $X_3$ is T, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H and $X_{15}$ is A.

In a further aspect, the heavy chain variable region comprises one or more framework sequences juxtaposed between the HVRs as: (FR-H1)-(HVR-H1)-(FR-H2)-(HVR-H2)-(FR-H3)-(HVR-H3)-(FR-H4), and the light chain variable regions comprises one or more framework sequences juxtaposed between the HVRs as: (FR-L1)-(HVR-L1)-(FR-L2)-(HVR-L2)-(FR-L3)-(HVR-L3)-(FR-L4). In a still further aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences are set forth as SEQ ID NOs:8, 9, 10 and 11. In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences are set forth as SEQ ID NOs:15, 16, 17 and 18.

In a still further specific aspect, the antibody further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further aspect, the murine constant region in IgG2A. In a still further specific aspect, the antibody has reduced or minimal effector function. In a still further specific aspect the minimal effector function results from an "effector-less Fc mutation" or aglycosylation. In still a further instance, the effector-less Fc mutation is an N297A or D265A/N297A substitution in the constant region.

In yet another instance, provided is an anti-PD-L1 antibody comprising a heavy chain and a light chain variable region sequence, wherein:

(a) the heavy chain further comprises an HVR-H1, HVR-H2 and an HVR-H3 sequence having at least 85% sequence identity to GFTFSDSWIH (SEQ ID NO:19), AWISPYGGSTYYADSVKG (SEQ ID NO:20) and RHWPGGFDY (SEQ ID NO:21), respectively, or (b) the light chain further comprises an HVR-L1, HVR-L2 and an HVR-L3 sequence having at least 85% sequence identity to RASQDVSTAVA (SEQ ID NO:22), SASFLYS (SEQ ID NO:23) and QQYLYHPAT (SEQ ID NO:24), respectively.

In a specific aspect, the sequence identity is 86%, 87%, 88%, 89%, 90%, 91%, 92%, 93%, 94%, 95%, 96%, 97%, 98%, 99% or 100%.

In another aspect, the heavy chain variable region comprises one or more framework sequences juxtaposed between the HVRs as: (FR-H1)-(HVR-H1)-(FR-H2)-(HVR-H2)-(FR-H3)-(HVR-H3)-(FR-H4), and the light chain variable regions comprises one or more framework sequences juxtaposed between the HVRs as: (FR-L1)-(HVR-L1)-(FR-L2)-(HVR-L2)-(FR-L3)-(HVR-L3)-(FR-L4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences are set forth as SEQ ID NOs:8, 9, 10 and 11. In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences are set forth as SEQ ID NOs:15, 16, 17 and 18.

In a still further specific aspect, the antibody further comprises a human or murine constant region.

In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further aspect, the murine constant region in IgG2A. In a still further specific aspect, the antibody has reduced or minimal effector function. In a still further specific aspect the minimal effector function results from an "effector-less Fc mutation" or aglycosylation. In still a further instance, the effector-less Fc mutation is an N297A or D265A/N297A substitution in the constant region.

In another further instance, provided is an isolated anti-PD-L1 antibody comprising a heavy chain and a light chain variable region sequence, wherein:

(a) the heavy chain sequence has at least 85% sequence identity to the heavy chain sequence: EVQLVESGG-GLVQPGGSLRLSCAASGFTFSDSWIHWVRQAPGK-GLEWVAWISPYGGSTYYADSVKGRFTIS ADTSKN-TAYLQMNSLRAEDTAVYYCARRHWPGGFDYWGQG TLVTVSS (SEQ ID NO:25), and/or (b) the light chain sequences has at least 85% sequence identity to the light chain sequence:

```
                                              (SEQ ID NO: 4)
DIQMTQSPSSLSASVGDRVTITCRASQDVSTAVAWYQQKPGKAPKLL
IYSASFLYSGVPSRFSGSGSGTDFTLTISSLQPEDFATYYCQQYLYH
PATFGQGTKVEIKR.
```

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (FR-H1)-(HVR-H1)-(FR-H2)-(HVR-H2)-(FR-H3)-(HVR-H3)-(FR-H4), and the light chain variable regions comprises one or more framework sequences juxtaposed between the HVRs as: (FR-L1)-(HVR-L1)-(FR-L2)-(HVR-L2)-(FR-L3)-(HVR-L3)-(FR-L4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences are set forth as SEQ ID NOs:8, 9, 10 and WGQGTLVTVSS (SEQ ID NO:27).

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences are set forth as SEQ ID NOs:15, 16, 17 and 18.

In a still further specific aspect, the antibody further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further aspect, the murine constant region in IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further instance, the effector-less Fc mutation is an N297A or D265A/N297A substitution in the constant region.

In a further aspect, the heavy chain variable region comprises one or more framework sequences juxtaposed between the HVRs as: (FR-H1)-(HVR-H1)-(FR-H2)-(HVR-H2)-(FR-H3)-(HVR-H3)-(FR-H4), and the light chain variable regions comprises one or more framework sequences juxtaposed between the HVRs as: (FR-L1)-(HVR-L1)-(FR-L2)-(HVR-L2)-(FR-L3)-(HVR-L3)-(FR-L4). In a still further aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
FR-H1
                                              (SEQ ID NO: 29)
EVQLVESGGGLVQPGGSLRLSCAASGFTFS

FR-H2
                                              (SEQ ID NO: 30)
WVRQAPGKGLEWVA

FR-H3
                                              (SEQ ID NO: 10)
RFTISADTSKNTAYLQMNSLRAEDTAVYYCAR

FR-H4
                                              (SEQ ID NO: 27)
WGQGTLVTVSS.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
FR-L1
                                              (SEQ ID NO: 15)
DIQMTQSPSSLSASVGDRVTITC

FR-L2
                                              (SEQ ID NO: 16)
WYQQKPGKAPKLLIY

FR-L3
                                              (SEQ ID NO: 17)
GVPSRFSGSGSGTDFTLTISSLQPEDFATYYC

FR-L4
                                              (SEQ ID NO: 28)
FGQGTKVEIK.
```

In a still further specific aspect, the antibody further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further aspect, the murine constant region in IgG2A. In a still further specific aspect, the antibody has reduced or minimal effector function. In a still further specific aspect the minimal effector function results from an "effector-less Fc mutation" or aglycosylation. In still a further instance, the effector-less Fc mutation is an N297A or D265A/N297A substitution in the constant region.

In yet another instance, provided is an anti-PD-L1 antibody comprising a heavy chain and a light chain variable region sequence, wherein:
  (c) the heavy chain further comprises an HVR-H1, HVR-H2 and an HVR-H3 sequence having at least 85% sequence identity to GFTFSDSWIH (SEQ ID NO:19), AWISPYGGSTYYADSVKG (SEQ ID NO:20) and RHWPGGFDY (SEQ ID NO:21), respectively, and/or
  (d) the light chain further comprises an HVR-L1, HVR-L2 and an HVR-L3 sequence having at least 85% sequence identity to RASQDVSTAVA (SEQ ID NO:22), SASFLYS (SEQ ID NO:23) and QQYLYHPAT (SEQ ID NO:24), respectively.

In a specific aspect, the sequence identity is 86%, 87%, 88%, 89%, 90%, 91%, 92%, 93%, 94%, 95%, 96%, 97%, 98%, 99% or 100%.

In another aspect, the heavy chain variable region comprises one or more framework sequences juxtaposed between the HVRs as: (FR-H1)-(HVR-H1)-(FR-H2)-(HVR-H2)-(FR-H3)-(HVR-H3)-(FR-H4), and the light chain variable regions comprises one or more framework sequences juxtaposed between the HVRs as: (FR-L1)-(HVR-L1)-(FR-L2)-(HVR-L2)-(FR-L3)-(HVR-L3)-(FR-L4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences are set forth as SEQ ID NOs:8, 9, 10 and WGQGTLVTVSSASTK (SEQ ID NO:31).

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences are set forth as SEQ ID NOs:15, 16, 17 and 18. In a still further specific aspect, the antibody further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further aspect, the murine constant region in IgG2A. In a still further specific aspect, the antibody has reduced or minimal effector function. In a still further specific aspect the minimal effector function results from an "effector-less Fc mutation" or aglycosylation. In still a further instance, the effector-less Fc mutation is an N297A or D265A/N297A substitution in the constant region.

In a still further instance, provided is an isolated anti-PD-L1 antibody comprising a heavy chain and a light chain variable region sequence, wherein:

(a) the heavy chain sequence has at least 85% sequence identity to the heavy chain sequence: EVQLVESGG-GLVQPGGSLRLSCAASGFTFSDSWIHWVRQAPGK-GLEWVAWISPYGGSTYYADSVKGRFTIS ADTSKN-TAYLQMNSLRAEDTAVYYCARRHWPGGFDYWGQG TLVTVSSASTK (SEQ ID NO:26), or (b) the light chain sequences has at least 85% sequence identity to the light chain sequence:

(SEQ ID NO: 4)
DIQMTQSPSSLSASVGDRVTITCRASQDVSTAVAWYQQKPGKAPKLL

IYSASFLYSGVPSRFSGSGSGTDFTLTISSLQPEDFATYYCQQYLYH

PATFGQGTKVEIKR.

In some instances, provided is an isolated anti-PD-L1 antibody comprising a heavy chain and a light chain variable region sequence, wherein the light chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO:4. In some instances, provided is an isolated anti-PD-L1 antibody comprising a heavy chain and a light chain variable region sequence, wherein the heavy chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO:26. In some instances, provided is an isolated anti-PD-L1 antibody comprising a heavy chain and a light chain variable region sequence, wherein the light chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:4 and the heavy chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:26. In some instances, one, two, three, four or five amino acid residues at the N-terminal of the heavy and/or light chain may be deleted, substituted or modified.

In a still further instance, provided is an isolated anti-PD-L1 antibody comprising a heavy chain and a light chain sequence, wherein:

(a) the heavy chain sequence has at least 85% sequence identity to the heavy chain sequence: EVQLVESGG-GLVQPGGSLRLSCAASGFTFSDSWIHWVRQAPGK-GLEWVAWISPYGGSTYYADSVKGRFTIS ADTSKN-TAYLQMNSLRAEDTAVYYCARRHWPGGFDYWGQG TLVTVSSASTKGPSVFPLAPSSKSTSGGTA ALGCLVKDYFPEPVTVSWNSGALT-SGVHTFPAVLQSSGLYS-LSSVVTVPSSSLGTQTYICNVNHKPSNTKVD KKVE-PKSCDKTHTCPPCPAPELLGGPSVFLFPPKPKDTLMIS-RTPEVTCVVVDVSHEDPEVKFNWYVDGVEV HNAKTKPRE-EQYASTYRVVSVLTVLHQDWLNGKEYKCKVSNKA-LPAPIEKTISKAKGQPREPQVYTLPPSRE EMT-KNQVSLTCLVKGFYPSDIAVEWESNGQPENNYKTTP PVLDSDGSFFLYSKLTVDKSRWQQGNVFSCSV MHEALHNHYTQKSLSLSPG (SEQ ID NO:32), and/or (b) the light chain sequences has at least 85% sequence identity to the light chain sequence:

(SEQ ID NO: 33)
DIQMTQSPSSLSASVGDRVTITCRASQDVSTAVAWYQQKPGKAPKLL

IYSASFLYSGVPSRFSGSGSGTDFTLTISSLQPEDFATYYCQQYLYH

PATFGQGTKVEIKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC.

In some instances, provided is an isolated anti-PD-L1 antibody comprising a heavy chain and a light chain sequence, wherein the light chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:33. In some instances, provided is an isolated anti-PD-L1 antibody comprising a heavy chain and a light chain sequence, wherein the heavy chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:32. In some instances, provided is an isolated anti-PD-L1 antibody comprising a heavy chain and a light chain sequence, wherein the light chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:33 and the heavy chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:32.

In some instances, the isolated anti-PD-L1 antibody is aglycosylated. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Removal of glycosylation sites form an antibody is conveniently accomplished by altering the amino acid sequence such that one of the above-described tripeptide sequences (for N-linked glycosylation sites) is removed. The alteration may be made by substitution of an asparagine, serine or threonine residue within the glycosylation site another amino acid residue (e.g., glycine, alanine or a conservative substitution).

In any of the instances herein, the isolated anti-PD-L1 antibody can bind to a human PD-L1, for example a human PD-L1 as shown in UniProtKB/Swiss-Prot Accession No.Q9NZQ7.1, or a variant thereof.

In a still further instance, provided is an isolated nucleic acid encoding any of the antibodies described herein. In some instances, the nucleic acid further comprises a vector suitable for expression of the nucleic acid encoding any of the previously described anti-PD-L1 antibodies. In a still further specific aspect, the vector is in a host cell suitable for expression of the nucleic acid. In a still further specific aspect, the host cell is a eukaryotic cell or a prokaryotic cell. In a still further specific aspect, the eukaryotic cell is a mammalian cell, such as Chinese hamster ovary (CHO) cell.

The antibody or antigen binding fragment thereof, may be made using methods known in the art, for example, by a process comprising culturing a host cell containing nucleic acid encoding any of the previously described anti-PD-L1 antibodies or antigen-binding fragments in a form suitable for expression, under conditions suitable to produce such antibody or fragment, and recovering the antibody or fragment.

It is expressly contemplated that such PD-L1 axis binding antagonist antibodies (e.g., anti-PD-L1 antibodies, anti-PD-1 antibodies, and anti-PD-L2 antibodies), or other antibodies described herein (e.g., anti-PD-L1 antibodies for detection of PD-L1 expression levels) for use in any of the instances enumerated above may have any of the features, singly or in combination, described in Sections 1-7 below.

1. Antibody Affinity

In certain instances, an antibody provided herein (e.g., an anti-PD-L1 antibody or an anti-PD-1 antibody) has a dissociation constant (Kd) of <1 µM, <100 nM, <10 nM, <1 nM, <0.1 nM, <0.01 nM, or ≤0.001 nM (e.g., $10^{-8}$ M or less, e.g., from $10^{-8}$ M to $10^{-13}$ M, e.g., from $10^{-9}$ M to $10^{-13}$ M).

In one instance, Kd is measured by a radiolabeled antigen binding assay (RIA). In one instance, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 µM or 26 µM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another instance, Kd is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one instance, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, for example, Chen et al., J. Mol. Biol. 293:865-881 (1999). If the on-rate exceeds $10^6$ $M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain instances, an antibody (e.g., an anti-PD-L1 antibody or an anti-PD-1 antibody) provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al. *Nat. Med.* 9:129-134 (2003); and Hollinger et al. *Proc. Natl. Acad. Sci. USA* 90: 6444-6448 (1993). Triabodies and tetrabodies are also described in Hudson et al. *Nat. Med.* 9:129-134 (2003).

Single-domain antibodies are antibody fragments comprising all or a portion of the heavy chain variable domain or all or a portion of the light chain variable domain of an antibody. In certain instances, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain instances, an antibody (e.g., an anti-PD-L1 antibody or an anti-PD-1 antibody) provided herein is a chimeric antibody. Certain chimeric antibodies are described, e.g., in U.S. Pat. No. 4,816,567; and Morrison et al. *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain instances, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some instances, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Natl. Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain instances, an antibody (e.g., an anti-PD-L1 antibody or an anti-PD-1 antibody) provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology. Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention (e.g., anti-PD-L1 antibodies and anti-PD-1 antibodies) may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); *Fellouse, Proc. Natl. Acad. Sci. USA* 101 (34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments.

Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In any one of the above aspects, an antibody (e.g., an anti-PD-L1 antibody or an anti-PD-1 antibody) provided herein may be a multispecific antibody, for example, a bispecific antibody. Multispecific antibodies are monoclonal antibodies that have binding specificities for at least two different sites. In certain instances, an antibody provided herein is a multispecific antibody, e.g., a bispecific antibody. In certain instances, one of the binding specificities is for PD-L1 and the other is for any other antigen. In certain instances, bispecific antibodies may bind to two different epitopes of PD-L. Bispecific antibodies may also be used to localize cytotoxic agents to cells which express PD-L. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (see, e.g., WO 2009/089004A1); cross-linking two or more antibodies or fragments (see, e.g., U.S. Pat. No. 4,676,980, and Brennan et al., *Science* 229: 81 (1985)); using leucine zippers to produce bi-specific antibodies (see, e.g., Kostelny et al., *J. Immunol.* 148(5): 1547-1553 (1992)); using "diabody" technology for making bispecific antibody fragments (see, e.g., Hollinger et al., *Proc. Natl. Acad. Sci. USA* 90:6444-6448 (1993)); using single-chain Fv (sFv) dimers (see, e.g., Gruber et al., *J. Immunol.* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g., US 2006/0025576A1).

The antibody or fragment herein also includes a "Dual Acting FAb" or "DAF" comprising an antigen binding site that binds to PD-L1 as well as another, different antigen.

7. Antibody Variants

In certain instances, amino acid sequence variants of the antibodies of the invention (e.g., anti-PD-L1 antibodies and anti-PD-1 antibodies) are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

I. Substitution, Insertion, and Deletion Variants

In certain instances, antibody variants having one or more amino acid substitutions are provided. Sites of interest for substitutional mutagenesis include the HVRs and FRs. Conservative substitutions are shown in Table 2 under the heading of "preferred substitutions." More substantial changes are provided in Table 2 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved Antibody-Dependent Cell-Mediated Cytotoxicity (ADCC) or Complement Dependant Cytotoxicity (CDC).

TABLE 2

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity and/or reduced immunogenicity) relative to the parent antibody and/or will have substantially retained certain biological properties of the parent antibody. An exemplary substitutional variant is an affinity matured antibody, which may be conveniently generated, for example, using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196 (2008)), and/or residues that contact antigen, with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001)). In some instances of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain instances, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen-contacting residues in the HVRs. In certain instances of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

II. Glycosylation variants

In certain instances, antibodies of the invention can be altered to increase or decrease the extent to which the antibody is glycosylated. Addition or deletion of glycosylation sites to an antibody of the invention may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some instances, modifications of the oligosaccharide in an antibody of the invention may be made in order to create antibody variants with certain improved properties.

In one instance, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, for example, U.S. Patent Publication Nos. US 2003/0157108 and US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); U.S. Pat. Appl. No. US 2003/0157108 A1; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4): 680-688 (2006); and WO2003/085107).

Antibody variants are further provided with bisected oligosaccharides, for example, in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

III. Fc region variants

In certain instances, one or more amino acid modifications may be introduced into the Fc region of an antibody of the invention, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions.

In certain instances, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability.

The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest are described in U.S. Pat. No. 5,500,362 (see, e.g., Hellstrom, I. et al. *Proc. Natl. Acad. Sci. USA* 83:7059-7063 (1986)) and Hellstrom, I et al., Proc. Natl. Acad. Sci. USA 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CYTOTOX 96® non-radioactive cytotoxicity assay (Promega, Madison, Wis.))). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Natl. Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, e.g., Gazzano-Santoro et al., *J. Immunol. Methods* 202:163 (1996); Cragg et al., *Blood.* 101:1045-1052 (2003); and Cragg et al., *Blood.* 103:2738-2743 (2004)). FcRn binding and in vivo clearance/half life determinations can also be performed using methods known in the art (see, e.g., Petkova et al. *Int'l. Immunol.* 18(12):1759-1769 (2006)).

Antibodies with reduced effector function include those with substitution of one or more of Fc region residues 238, 265, 269, 270, 297, 327 and 329 (U.S. Pat. Nos. 6,737,056 and 8,219,149). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. Nos. 7,332,581 and 8,219,149).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain instances, an antibody variant comprises an Fc region with one or more amino acid substitutions which improve ADCC, e.g., substitutions at positions 298, 333, and/or 334 of the Fc region (EU numbering of residues).

In some instances, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn.

Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

IV. Cysteine Engineered Antibody Variants

In certain instances, it may be desirable to create cysteine engineered antibodies, e.g., "thioMAbs," in which one or more residues of an antibody are substituted with cysteine residues. In particular instances, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain instances, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

V. Antibody Derivatives

In certain instances, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another instance, conjugates of an antibody and nonproteinaceous moiety that may be selectively heated by exposure to radiation are provided. In one instance, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

VI. Immunoconjugates

The invention also provides immunoconjugates comprising an antibody herein (e.g., an anti-PD-L1 antibody or an anti-PD-1 antibody) conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one instance, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another instance, an immunoconjugate comprises an antibody as described herein conjugated to an enzymatically active toxin or fragment thereof, including but not limited to diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), Momordica charantia inhibitor, curcin, crotin, Sapaonaria officinalis inhibitor, gelonin, mitogellin, restrictocin, phenomycin, enomycin, and the tricothecenes.

In another instance, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or 1123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, sulfo-SMPB, and SVSB (succinimidyl-(4-vinylsulfone)benzoate) which are commercially available (e.g., from Pierce Biotechnology, Inc., Rockford, Ill., U.S.A).

V. Pharmaceutical Formulations

Therapeutic formulations of the PD-L1 axis binding antagonists used in accordance with the present invention (e.g., an anti-PD-L1 antibody (e.g., MPDL3280A)) are prepared for storage by mixing the antagonist having the desired degree of purity with optional pharmaceutically acceptable carriers, excipients, or stabilizers in the form of lyophilized formulations or aqueous solutions. For general information concerning formulations, see, e.g., Gilman et al. (eds.) *The Pharmacological Bases of Therapeutics*, 8th Ed., Pergamon Press, 1990; A. Gennaro (ed.), *Remington's Pharmaceutical Sciences*, 18th Edition, Mack Publishing Co., Pennsylvania, 1990; Avis et al. (eds.) *Pharmaceutical Dosage Forms: Parenteral Medications Dekker*, New York, 1993; Lieberman et al. (eds.) *Pharmaceutical Dosage Forms: Tablets Dekker*, New York, 1990; Lieberman et al. (eds.), *Pharmaceutical Dosage Forms: Disperse Systems Dekker*, New York, 1990; and Walters (ed.) *Dermatological and Transdermal Formulations* (Drugs and the Pharmaceutical Sciences), Vol 119, Marcel Dekker, 2002.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG).

The formulation herein may also contain more than one active compound, preferably those with complementary activities that do not adversely affect each other. The type and effective amounts of such medicaments depend, for example, on the amount and type of antagonist present in the formulation, and clinical parameters of the subjects.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antagonist, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid.

The formulations to be used for in vivo administration must be sterile. This is readily accomplished by filtration through sterile filtration membranes.

It is to be understood that any of the above articles of manufacture may include an immunoconjugate described herein in place of or in addition to a PD-L1 axis binding antagonist.

VI. Diagnostic Kits and Articles of Manufacture

Provided herein are diagnostic kits comprising one or more reagents for determining the presence of a biomarker (e.g., PD-L1 expression levels, for instance, in tumor-infiltrating immune cells) in a sample from an individual or patient with a disease or disorder (e.g., cancer, including bladder cancer). In some instances, the presence of the biomarker in the sample indicates a higher likelihood of efficacy when the individual is treated with a PD-L1 axis binding antagonist. In some instances, the absence of the biomarker in the sample indicates a lower likelihood of efficacy when the individual with the disease is treated with the PD-L1 axis binding antagonist. Optionally, the kit may further include instructions to use the kit to select a medicament (e.g., a PD-L1 axis binding antagonist, such as an anti-PD-L1 antibody such as MPDL3280A) for treating the disease or disorder if the individual expresses the biomarker in the sample. In another instance, the instructions are to use the kit to select a medicament other than PD-L1 axis binding antagonist if the individual does not express the biomarker in the sample.

Provided herein are also articles of manufacture including, packaged together, a PD-L1 axis binding antagonist (e.g., an anti-PD-L1 antibody) in a pharmaceutically acceptable carrier and a package insert indicating that the PD-L1 axis binding antagonist (e.g., anti-PD-L1 antibody) is for treating a patient with a disease or disorder (e.g., cancer) based on the expression of a biomarker. Treatment methods include any of the treatment methods disclosed herein. The invention also concerns a method for manufacturing an article of manufacture comprising combining in a package a pharmaceutical composition comprising a PD-L1 axis binding antagonist (e.g., an anti-PD-L1 antibody) and a package insert indicating that the pharmaceutical composition is for treating a patient with a disease or disorder based on expression of a biomarker (e.g., PD-L1 expression levels, for instance, in tumor cells and/or tumor-infiltrating immune cells).

The article of manufacture may include, for example, a container and a label or package insert on or associated with the container. Suitable containers include, for example, bottles, vials, syringes, and the like. The container may be formed from a variety of materials such as glass or plastic. The container holds or contains a composition comprising the cancer medicament as the active agent and may have a sterile access port (e.g., the container may be an intravenous solution bag or a vial having a stopper pierceable by a hypodermic injection needle).

The article of manufacture may further include a second container comprising a pharmaceutically-acceptable diluent buffer, such as bacteriostatic water for injection (BWFI), phosphate-buffered saline, Ringer's solution, and/or dextrose solution. The article of manufacture may further include other materials desirable from a commercial and user standpoint, including other buffers, diluents, filters, needles, and syringes.

The article of manufacture of the present invention also includes information, for example in the form of a package insert, indicating that the composition is used for treating cancer based on the expression level of the biomarker(s) herein. The insert or label may take any form, such as paper or on electronic media such as a magnetically recorded medium (e.g., floppy disk), a CD-ROM, a Universal Serial Bus (USB) flash drive, and the like. The label or insert may also include other information concerning the pharmaceutical compositions and dosage forms in the kit or article of manufacture.

EXAMPLES

The following examples are provided to illustrate, but not to limit the presently claimed invention.

Example 1: Immunohistochemical (IHC) Analysis of PD-L1 Expression in Tumor Samples Immunohistochemistry (IHC): Formalin-fixed, paraffin-embedded tissue sections were deparaffinized prior to antigen retrieval, blocking and incubation with primary anti-PD-L1 antibody. Following incubation with secondary antibody and enzymatic color development, sections were counterstained and dehydrated in series of alcohols and xylenes before coverslipping.

The following protocol was used for IHC. The Ventana BENCHMARK XT™ automated staining instrument or BENCHMARK ULTRA™ automated staining instrument system was used to perform PD-L1 IHC staining using the following reagents and materials:
Primary antibody: anti-PD-L1 Rabbit Monoclonal Primary Antibody
Specimen Type: Formalin-fixed paraffin embedded (FFPE) section of tumor samples
Epitope Recovery Conditions: Cell Conditioning, standard 1 (CC1, Ventana, cat #950-124)
Primary Antibody Conditions: 1/100, 6.5 µg/ml for 16 minutes at 36° C.
Diluent: Antibody dilution buffer (Tris-buffered saline containing carrier protein and BRIJ™-35)
Negative control: Naive Rabbit IgG at 6.5 µg/ml (Cell Signaling) or diluent alone
Detection: Optiview or ultraView Universal DAB Detection kit (Ventana), and amplification kit (if applicable) were used according to manufacturer's instructions (Ventana).
Counterstain: Ventana Hematoxylin II (cat #790-2208)/with Bluing reagent (Cat #760-2037) (4 minutes and 4 minutes, respectively)

The Ventana BENCHMARK™ automated staining instrument Protocol was as follows:
1. paraffin (Selected)
2. Deparaffinization (Selected)
3. Cell Conditioning (Selected)
4. Conditioner #1 (Selected)
5. Standard CC1 (Selected)
6. Ab Incubation Temperatures (Selected)
7. 36C Ab Inc. (Selected)
8. Titration (Selected)
9. Auto-dispense (Primary Antibody), and Incubate for (16 minutes)
10. Countstain (Selected)
11. Apply One Drop of (Hematoxylin II) (Countstain), Apply Coverslip, and Incubate for (4 minutes)
12. Post Counterstain (Selected)
13. Apply One Drop of (BLUING REAGENT) (Post Countstain), Apply Coverslip, and Incubate for (4 minutes)
14. Wash slides in soap water to remove oil
15. Rinse slides with water
16. Dehydrate slides through 95% Ethanol, 100% Ethanol to xylene (Leica autostainer program #9)
17. Cover slip.

Example 2: Association Between PD-L1 Expression in Tumor-Infiltrating Immune Cells (ICs) and Response to Treatment with PD-L1 Axis Binding Antagonists The association between PD-L1 expression in tumor-infiltrating immune cells within urothelial bladder cancer (UBC) tumors with benefit from treatment with PD-L1 axis binding antagonists was evaluated. The UBC patients studied were enrolled in an ongoing phase Ia study that includes a cohort of UBC patients (safety-evaluable UBC population=92). Key eligibility criteria included measurable disease per Response Evaulation Criteria In Solid Tumors (RECIST) v1.1 and an Eastern Cooperative Oncology Group (ECOG) Performance Status (PS) of 0 or 1. The UBC cohort originally enrolled patients with PD-L1 IC scores of IC2/3 but was then expanded to include all-comers, primarily recruiting PD-L1 IC0/1 patients. PD-L1 IC scores were scored as shown in Table 3. Atezolizumab (MPDL3280A) was administered intravenously (IV) every three weeks (q3w) at 15 mg/kg or 1200 mg flat dose.

TABLE 3

| Tumor-infiltrating immune cell (IC) IHC diagnostic criteria | |
|---|---|
| PD-L1 Diagnostic Assessment | IC Score |
| Absence of any discernible PD-L1 staining OR Presence of discernible PD-L1 staining of any intensity in tumor-infiltrating immune cells covering <1% of tumor area occupied by tumor cells, associated intratumoral stroma, and contiguous peri-tumoral desmoplastic stroma | IC0 |
| Presence of discernible PD-L1 staining of any intensity in tumor-infiltrating immune cells covering ≥1% to <5% of tumor area occupied by tumor cells, associated intratumoral stroma, and contiguous peri-tumoral desmoplastic stroma | IC1 |
| Presence of discernible PD-L1 staining of any intensity in tumor-infiltrating immune cells covering ≥5% to <10% of tumor area occupied | IC2 |

TABLE 3-continued

Tumor-infiltrating immune cell (IC) IHC diagnostic criteria

| PD-L1 Diagnostic Assessment | IC Score |
|---|---|
| by tumor cells, associated intratumoral stroma, and contiguous peri-tumoral desmoplastic stroma | |
| Presence of discernible PD-L1 staining of any intensity in tumor-infiltrating immune cells covering ≥10% of tumor area occupied by tumor cells, associated intratumoral stroma, and contiguous peri-tumoral desmoplastic stroma | IC3 |

The expression level of PD-L1 in the UBC tumor microenvironment was evaluated by performing IHC using a rabbit monoclonal anti-PD-L1 primary antibody (see Example 1). This assay is optimized for detection of PD-L1 expression level in both tumor-infiltrating immune cells and in tumor cells (TC). FIG. 1B shows the prevalence of PD-L1 expression at the different IC score cutoffs in archival tumor tissue from patients prescreened in the phase Ia study. FIG. 1C shows an example of a UBC tumor section showing PD-L1 expression in IC as assessed by PD-L1 IHC. The IHC assay was highly sensitive and specific for PD-L1 expression.

Figure 3:
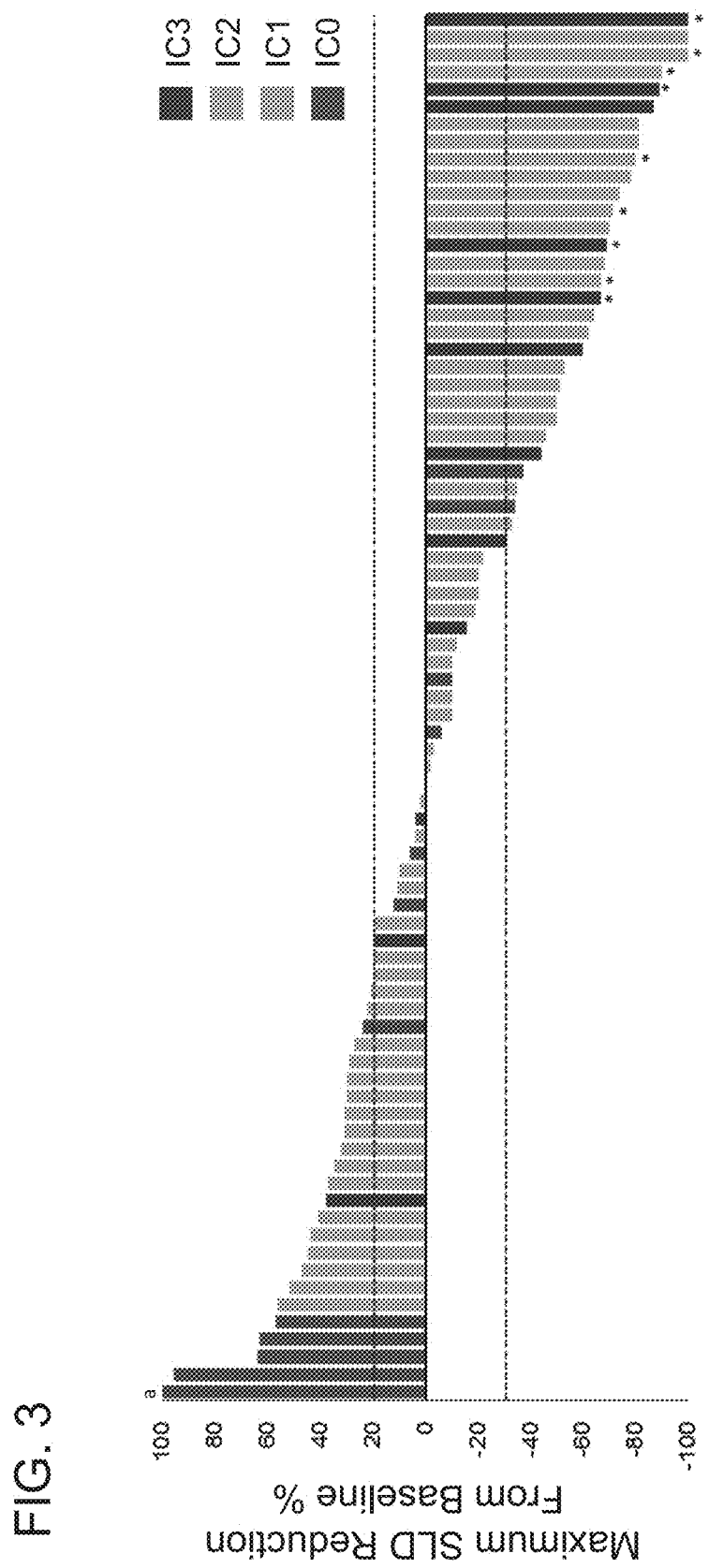
FIG. 3 is a graph showing response of UBC patients to treatment with atezolizumab (MPDL3280A). The IC score of the patients are indicated. SLD, sum of longest diameter of the target lesions. Seven patients without post-baseline tumor assessments were not included. Asterisks denote 9 CR patients who had not all been confirmed by the data cutoff date, 7 of whom had <100% reduction due to lymph node target lesions. All lymph notes returned to normal size per RECIST v1.1. $^a$Change in SLD>100%.

Responses to treatment with atezolizumab (MPDL3280A) were observed in all PD-L1 subgroups, with higher objective response rates (ORRs) associated with higher PD-L1 expression in ICs (FIG. 2). For example, ORRs were 50% and 17% in IC2/3 and IC0/1 patients, respectively (FIG. 2). 20% of IC2/3 patients had a complete response (CR), and 30% had a partial response (PR) (FIG. 2). Responders also included patients with visceral metastases at baseline: 38% ORR (95% confidence interval (CI), 21-56) in 32 IC2/3 patients and 14% (95% CI, 5-30) ORR in 36 IC0/1 patients. Forty-four of 80 (55%) of patients with post-baseline tumor assessments experienced a reduction in tumor burden (FIG. 3). Decreased circulating inflammatory marker (CRP) and tumor markers (CEA, CA-19-9) were also observed in patients responding to atezolizumab.

Figure 4:
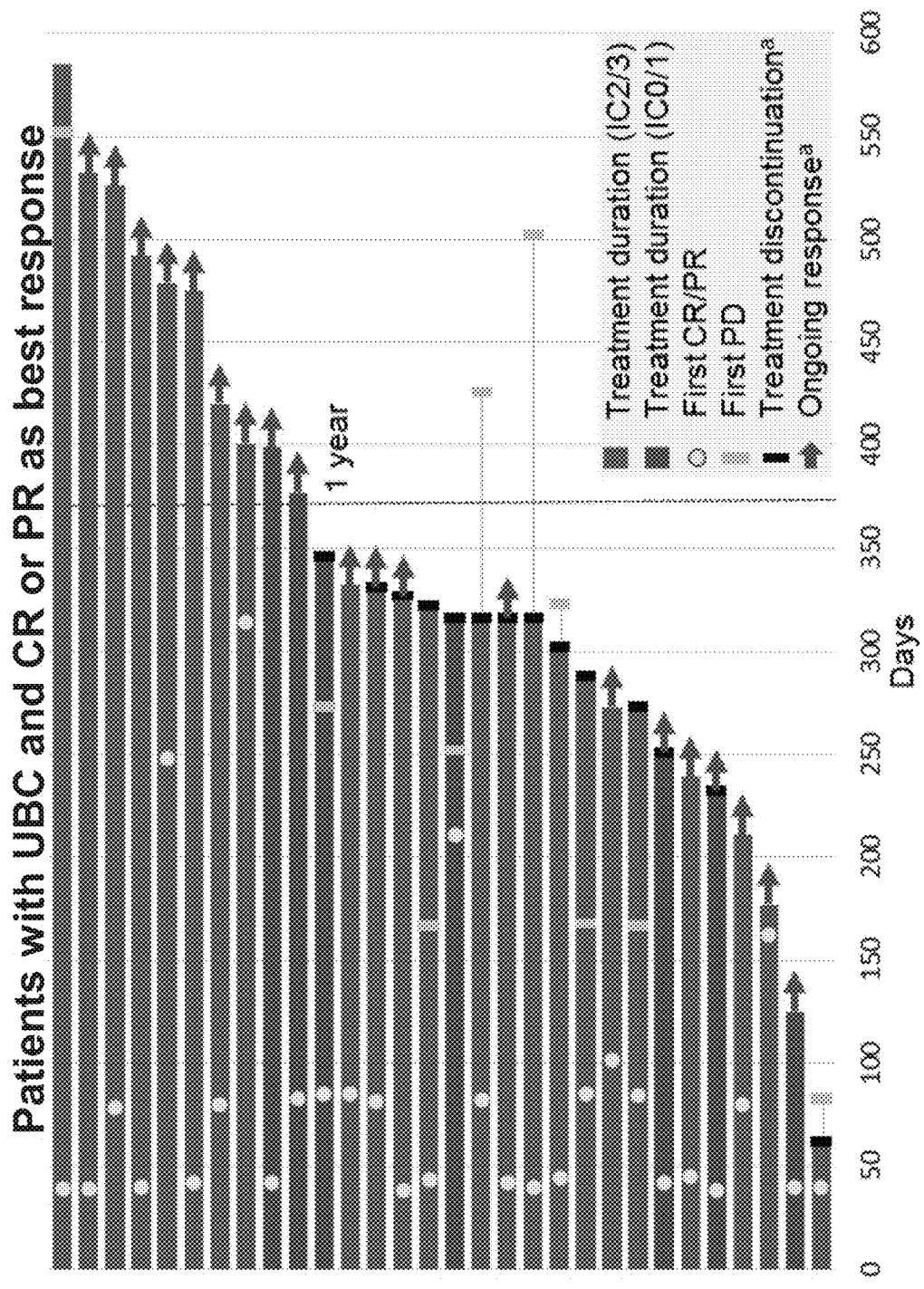
FIG. 4 is a graph showing duration of treatment and response in UBC patients treated with atezolizumab (MPDL3280A). Markers for discontinuation and ongoing response status have no implication on timing.

Duration of treatment and response for UBC patients treated with atezolizumab (MPDL3280A) is shown in FIG. 4. The median time to response was 62 days (IC2/3 patients, range 1+ to 10+ months; IC0/1 patients, range 1+ to 7+ months). 20 of 30 responding patients had ongoing responses at the time of data cutoff (Dec. 2, 2014). The median duration of response (DOR) was not reached as of the data cutoff.

PD-L1 expression in ICs appeared to be predictive of benefit from atezolizumab treatment (FIGS. 5A and 5B). The median progression free-survival (mPFS) and 1-year PFS rates were higher in atezolizumab-treated patients with higher PD-L1 expression (FIG. 5A). The same association was observed for 1-year overall survival (OS) rates, and the median overall survival (OS) was not yet reached as of the data cutoff (FIGS. 5A and 5B). The 1-year OS rates were 57% and 38% for IC2/3 and IC0/1 patients, respectively (FIG. 5A).

In summary, atezolizumab (MPDL3280A) has demonstrated promising clinical activity in a heavily pre-treated metastatic UBC cohort with encouraging survival and clinically meaningful responses. PD-L1 expression in ICs appeared to be a predictive biomarker for response to PD-L1 axis binding antagonists such as the anti-PD-L1 antibody atezolizumab (MPDL3280A).

Example 3: Phase La Study Examining the Association of Immunoblocker Signature and CTLA4 Expression Levels On Therapy With Response of UBC Patients To Atezolizumab The association between response to treatment with atezolizimab with expression of a "immunoblocker" signature (including the genes CTLA4, BTLA, LAG3, HAVCR2, and PD1) during therapy was evaluated during the course of a Phase Ia clinical study that included a cohort of UBC patients.

Figure 6:
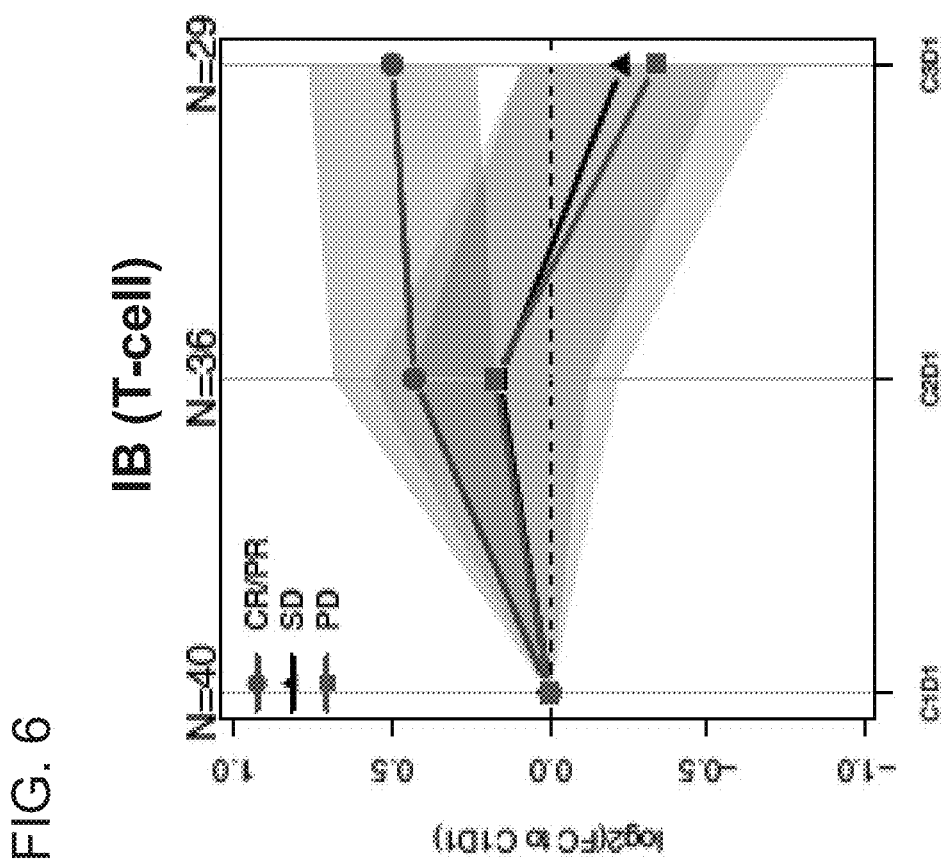
FIG. 6 is a series of graphs showing an association between the expression level of the immunoblocker gene signature (CTLA4, BTLA, LAG3, HAVCR2, PD1) or CTLA4 in peripheral blood mononuclear cells (PBMCs) with response during treatment of UBC patients with atezolizumab. C, cycle; D, day.

As shown in FIG. 6, increased mRNA expression (as determined by a custom Nanostring assay) of the immunoblocker signature, as well as CTLA4, by T-cells by cycle 3, day 1 of treatment was associated with response to atezolizumab in UBC patients. Therefore, the expression levels of CTLA4, BTLA, LAG3, HAVCR2, and PD1 represent potential biomarkers for response of UBC patients to treatment with PD-L1 axis binding antagonists, including the anti-PD-L1 antibody atezolizumab.

Example 4: Overview of Phase II Study Examining the Association of Atezolizumab and TCGA Subtype in Patients with Locally Advanced and Metastatic Carcinoma Study oversight and conduct The study was approved by the independent review board at each participating site and was conducted in full conformance of the provisions of the Declaration of Helsinki and the Good Clinical Practice Guidelines. An independent Data Monitoring Committee reviewed the available safety data every six months after the first patient enrolled.

Figure 7:
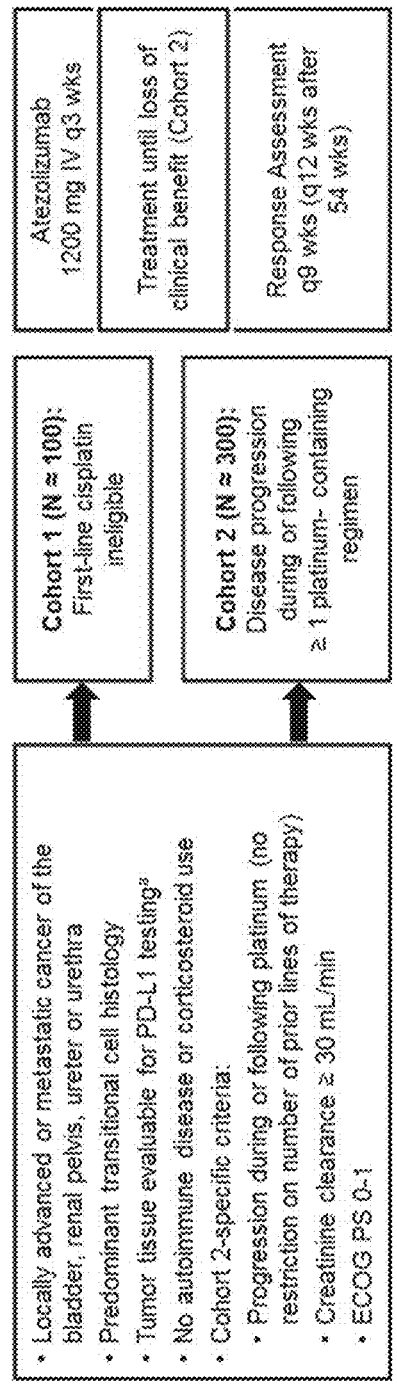
FIG. 7 is a schematic diagram of the overall design of the phase II trial. The tumor tissue evaluable for PD-L1 testing was prospectively assessed by a central laboratory. The patients and investigators were blinded to PD-L1 IHC status.

Study design and treatment This was a Phase 2, global, multicenter, single-arm two-cohort trial, as outlined in FIG. 7. One cohort consisted of patients who were treatment naive in the metastatic setting and considered to be cisplatin-ineligible. The second cohort consisted of patients with inoperable locally advanced or metastatic urothelial carcinoma whose disease had progressed after prior platinum-based chemotherapy and received a fixed dose of 1200 mg intravenous atezolizumab administered on Day 1 of each 21-day cycle. Dose interruptions were allowed, but dose reductions were not permitted. Patients were informed of the potential for pseudo-progression as part of the consent process and advised to discuss treatment beyond progression with their study physician. Patients were permitted to continue atezolizumab treatment after RECIST v1.1 criteria for progressive disease if they met pre-specified criteria for clinical benefit to allow for identification of non-conventional responses.

The primary efficacy endpoint of this study was objective response rate (ORR) based upon two distinct methods: independent review facility (IRF)-assessed per RECIST version 1.1, and investigator-assessed per modified RECIST criteria to better evaluate atypical response kinetics observed with immunotherapy (see Eisehauer et al. Eur. J. Cancer. 45:228-47, 2009; Nishino et al. Eur. J. Radiol. 84:1259-68, 2015). Dual endpoints were chosen due to the emerging recognition that RECIST v1.1 may be inadequate to fully capture the benefit of the unique patterns of response from immunotherapeutic agents (see Chiou et al. J. Clin. Oncol. 33:3541-3, 2015). Secondary efficacy endpoints included: duration of response and progression-free survival by both independent review per RECIST v1.1 and investigator assessed per modified RECIST, overall survival, 12-month overall survival, and safety. Exploratory analyses included the association between gene expression profiling and CD8+ T cell infiltration with clinical outcomes.

Patients Patients were eligible for enrollment in the study if they had histologically or cytologically documented locally advanced (T4b, any N; or any T, N 2-3) or metastatic (M1, Stage IV) urothelial carcinoma (including renal pelvis, ureter, urinary bladder, urethra). Eligible patients had an Eastern Cooperative Oncology Group (ECOG) performance status of 0 or 1; measurable disease defined by RECIST v1.1; adequate hematologic and end-organ function; and no autoimmune disease or active infections. Formalin-fixed paraffin-embedded (FFPE) tumor specimens with sufficient viable tumor content were required prior to study enrollment.

Study assessments Measurable and evaluable lesions were assessed and documented prior to treatment. Patients underwent tumor assessments every nine weeks for the first 12 months following Cycle 1, Day 1. After 12 months, tumor assessments were performed every 12 weeks. Safety assessments were performed according to National Cancer Institute Common Terminology Criteria for Adverse Events (NCI CTCAE), Version 4.0. Samples of archived tumor tissues, as well as serum and plasma samples, were collected for exploratory biomarker assessments.

PD-L1 immunohistochemistry Patient tumor samples were prospectively and centrally assessed for PD-L1 expression by immunohistochemistry using the diagnostic anti-human PD-L1 monoclonal antibody SP142 (see Powles et al. Nature 515:558-62, 2014). The PD-L1 tumor-infiltrating immune cell (IC) status was defined by the percentage of PD-L1 positive ICs: IC0 (<1%); IC1 (≥1% but <5%); and IC2/3 (≥5%). Areas of *Bacillus* Calmette-Guérin (BCG) inflammatory response were excluded from the assessment of PD-L1 IC status. An analysis of PD-L1 expression on tumor cells and CD8+ infiltration by immunohistochemistry was also performed (see Herbst et al. Nature 515:563-7, 2014; Ferlay et al. Int. J. Cancer 136:E359-86, 2012). The pre-screening biopsies were collected from archived paraffin-embedded tissue. Patients were required to have tissue sent to the central laboratory before study entry. Samples were processed at the time of screening. Formalin-fixed paraffin-embedded tumor tissue was stained prospectively for PD-L1 by immunohistochemistry using SP142. Samples were scored for PD-L1 expression on tumor-infiltrating immune cells, which included macrophages, dendritic cells and lymphocytes. Specimens were scored as immunohistochemistry IC 0, 1, 2, or 3 if <1%, ≥1% but <5%, ≥5% but <10%, or ≥10% of tumor-infiltrating immune cells were PD-L1 positive, respectively. PD-L1 scores in patients with multiple specimens from different time points or samples were based on the highest score. This assay was validated for investigational use in clinical trials at the IC1 and IC2 cutoff. An exploratory analysis of PD-L1 expression on tumor cells (TC) was conducted. Specimens were scored as immunohistochemistry TC0, TC1, TC2, or TC3 if <1%, ≥1% but <5%, ≥5% but <50%, or ≥50% of tumor cells were PD-L1 positive, respectively.

Exploratory biomarker analyses Gene expression levels were quantified by Illumina TruSeq RNA Access RNA-seq (see Wu et al.

Bioinformatics 26:873-81, 2010; Law et al. Genome Biol. 15:R29, 2014; Ritchie et al. Nucleic Acids Res. 43:e47, 2015). Molecular subtypes were assigned following TCGA (see, e.g., Cancer Genome Atlas Research Network Nature 507:315-22, 2014 and Jiang et al. Bioinformatics 23:306-13, 2007, each of which is herein incorporated by reference in its entirety), with some modifications to adapt for the use of RNA Access RNA-seq platform for FFPE tissues.

RNA-SEQ library preparation RNA was isolated from slides of FFPE tumor samples as previously described in Torre et al. (2012) Cancer J Clin. 65:87-108. RNA-Seq was performed using the Illumina TruSeq RNA Access Kit. Libraries and hybrid capture was performed as per the manufacturer's protocol. Briefly, approximately 100ng of RNA, as quantified by RiboGreen® was used as input. Quality was assessed by running the samples on the Bioanalyzer to determine the DV200 (% of RNA fragments >200 bp) value. First strand cDNA synthesis was primed from total RNA using random primers, followed by second strand cDNA synthesis with dUTP to preserve strand information. Double stranded cDNA underwent end-repair, A-tailing, and ligation of Illumina specific adapters include index sequences for sample barcoding. The resulting libraries were PCR amplified and quantified to determine yield and size distribution. All libraries were normalized and four libraries were pooled into a single hybridization/capture reaction. Pooled libraries were incubated with a cocktail of biotinylated oligos corresponding to coding regions of the genome. Targeted library molecules were captured via hybridized biotinylated oligo probes using streptavidin-conjugated beads. After two rounds of hybridization/capture reactions, the enriched library molecules were subjected to a second round of PCR amplification prior to paired-end 2×50 sequencing on the Illumina HiSeq.

Alignment, normalization and gene expression quantitation Reads were filtered for quality and to remove rRNA contamination, and then aligned to the genome (GRCh38) using GSNAP (version 2013-10-10) with the following options: -M 2-n 10-B 2-i 1-N 1-w 200000-E 1—pairmax-rna=200000—clip-overlap (see Morales et al. J Urol. 116: 180-3, 1976). We obtained an average of 54.7 million concordantly and uniquely aligned read pairs per sample. For purposes of normalization, size factors were computed using the DESeq algorithm (see vo der Maase et al. J Clin. Oncol. 23:4602-8, 2005). Read counts were then transformed using the voom algorithm, which provides log-transformed results suitable for visualization. In addition to transforming count data, voom also provides per-observation weights which permit application of the limma empirical Bayes framework for differential expression testing, relative to PD-L1 IHC IC or response (see De Santis et al. J Clin. Oncol. 30:191-9, 2012; Bellmunt et al. J. Clin. Oncol. 27:4454-61, 2009).

Subtype assignment

Molecular subtyping was based on molecular subtypes in bladder suggested by The Cancer Genome Atlas (TCGA) and described in TCGA Research Network, Nature. 507: 315-22, 2014. The TCGA classifier could not be directly applied to our data, due to significant differences in per-gene signal behavior between standard poly(A) RNA-seq for fresh material and RNA Access RNA-seq for FFPE material. Instead, our samples were clustered according to the expression of the following genes, which correspond to TCGA's FIG. 3: FGFR3, CDKN2A, KRT5, KRT14, EGFR, GATA3, FOXA1, and ERBB2 (see TCGA Research Network, Nature. 507:315-22, 2014). CDKN2A was used as a replacement for TCGA's miR-99a-5p and miR-100-5p because like miR-99a-5p and miR-100-5p, TCGA found CDKN2A to be strongly anti-correlated with FGFR3. See TCGA FIG. 1 in TCGA Research Network, Nature. 507:315-22, 2014. Clusters of patients could then be assigned in a straightforward fashion to the TCGA molecular subtypes by matching the gene expression patterns of each cluster with the patterns reported by TCGA. One outgroup with mixed expression behavior that was not consistent with the TCGA I, II, III, or IV data (n=18) was left unclassified and omitted from downstream analysis.

Statistical analysis

Efficacy analyses were based on the intent-to-treat (ITT) population. Objective response rate was determined on the objective response-evaluable population, defined as intent-to-treat patients who had measureable disease per RECIST v1.1 at baseline, and duration-of-response analyses were performed on the subset of patients who achieved an objective response. For the primary endpoint of objective response rate, a hierarchical fixed-sequence testing procedure was used to compare the objective response rate between the treatment arm and a historical control of 10% for three pre-specified populations: objective response-evaluable patients with a PD-L1 IHC score of [i] IC2/3; [ii] IC1/2/3; and [iii] all objective response-evaluable patients. The hypothesis tests on these three populations were sequentially performed on the basis of IRF-assessed objective response rate according to RECIST v1.1 and the investigator-assessed objective response rate according to modified RECIST at a specific two-sided α level of 0.05 for each test, while controlling the overall Type I error at the same α level, triggered by a minimum of 24-weeks of follow-up from the last patient enrolled. Safety analyses were performed on all treated patients, defined as enrolled patients who received any amount of the study drug. Additional biomarker analyses beyond PD-L1 IC were exploratory only and not pre-specified. The biomarker evaluable population was based upon objective response-evaluable population who had available associated gene expression data.

Figure 8:
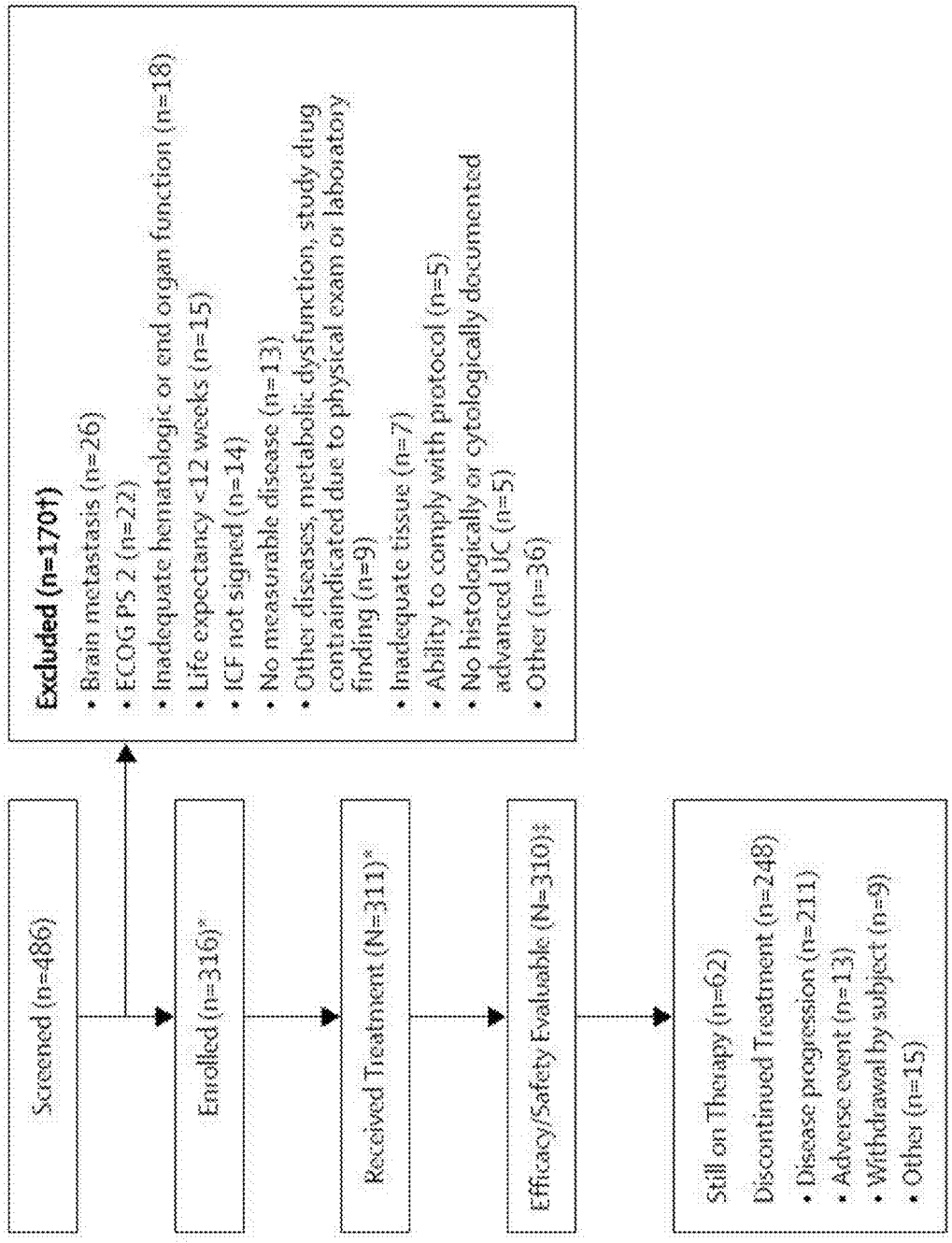
FIG. 8 is an overview of the cohort enrolled in the phase II trial. The excluded group includes re-screened patients. The treatment group is composed of 311 patients, and the efficacy evaluable group is composed of 310 patients. One patient was removed from the treatment group due to their tumor sample being from an unknown site.

Example 5: Results of Phase II Study Examining the Association of Atezolizumab and TCGA Subtype in Patients with Locally Advanced and Metastatic Carcinoma Patient characteristics A total of 486 patients were screened and 315 patients were enrolled in the study in Cohort 2, as seen in FIGS. 7 and 8. 310 patients received at least one dose of atezolizumab and were evaluable for efficacy and safety. At the time of the data cutoff, 202 patients (65%) had discontinued treatment (193 patients had died, eight due to withdrawal by patient, and one due to other reasons) and 9 patients discontinued from the study) with 118 patients (35%) remaining in the study after a minimum of 9.9 months of follow-up from the last enrolled patient.

Table 4 summarizes the baseline characteristics of the patients. 41% of patients had received two or more prior systemic regimens for metastatic disease. Many patients had adverse prognostic risk factors, including, visceral and/or liver metastasis at study entry (78% and 31%, respectively), and baseline hemoglobin <10 g/dL (22%).

Tissue for PD-L1 immunohistochemistry analysis consisted of surgical resection specimens (n=215), biopsies from primary lesions (n=23) or metastatic sites (n=41), transurethral resection of bladder tumor (TURBT) samples (n=29), and biopsy from unknown lesion (n=2). PD-L1 IC2/3 prevalence was higher in resection and TURBT specimens versus biopsies from primary lesions or metastatic sites (39% and 34% versus 17% and 8%, respectively). Patients were evenly distributed between the PD-L1 IC groups: IC0 (33%), IC1 (35%), and IC2/3 (32%). Baseline characteristics were well balanced between the IC2/3 group, IC1/2/3 group and the intent to treat population (Table 4).

TABLE 4

| | IC1/2/3 Group and Intent-to-Treat Population | | |
|---|---|---|---|
| Characteristic | IC2/3 n = 100 | IC1/2/3 n = 207 | All Patients N = 310 |
| Age, Median, years (range) | 66 (41-84) | 67 (32-91) | 66 (32-91) |
| Sex, male, n (%) | 78 (78) | 160 (77) | 241 (78) |
| Race, Caucasian, n (%) | 87 (87) | 184 (89) | 282 (91) |
| Site of primary tumor, n (%) | | | |
| Bladder | 79 (79) | 159 (77) | 230 (74) |
| Renal pelvis | 11 (11) | 27 (13) | 42 (14) |
| Ureter | 5 (5) | 12 (6) | 23 (7) |
| Urethra | 3 (3) | 5 (2) | 5 (2) |
| Other | 2 (2) | 4 (2) | 10 (3) |
| Baseline creatinine clearance, mL/min, n (%) | 40 (40) | 69 (33) | 110 (36) |
| ECOG PS, n (%) | | | |
| 0 | 42 (42) | 83 (40) | 117 (38) |
| 1 | 58 (58) | 124 (60) | 193 (62) |
| Hemoglobin, <10 g/dL, n (%) | 24 (24) | 50 (24) | 69 (22) |
| Tobacco use, n (%) | | | |
| Current | 6 (6) | 19 (9) | 35 (11) |
| Never | 34 (34) | 72 (35) | 107 (35) |
| Previous | 60 (60) | 116 (56) | 168 (54) |
| Bellmunt risk factors, number, n (%) | | | |
| 0 | 31 (31) | 61 (30) | 83 (27) |
| 1 | 35 (35) | 72 (35) | 117 (38) |
| 2 | 28 (28) | 59 (29) | 89 (29) |
| 3 | 6 (6) | 15 (7) | 21 (7) |
| Metastatic sites at baseline, n (%) | | | |
| Visceral[a] | 66 (66) | 152 (73) | 243 (78) |
| Liver | 27 (27) | 61 (30) | 96 (31) |

TABLE 4-continued

| | IC1/2/3 Group and Intent-to-Treat Population | | |
|---|---|---|---|
| Characteristic | IC2/3 n = 100 | IC1/2/3 n = 207 | All Patients N = 310 |
| Lymph node only | 24 (24) | 39 (19) | 43 (14) |
| Prior cystectomy, yes, n (%) | 44 (44) | 83 (40) | 115 (37) |
| Time from prior chemotherapy ≤3 months, n (%) | 43 (43) | 87 (42) | 121 (39) |
| Prior therapy with platinum-based regimen, n (%) | | | |
| Cisplatin-based | 83 (83) | 161 (78) | 227 (73) |
| Carboplatin-based | 17 (17) | 43 (21) | 80 (26) |
| Other platinum combination | 0 | 3 (1) | 3 (1) |
| Prior neoadjuvant or adjuvant chemotherapy, with first progression ≤ 12 months, n (%) | 24 (24) | 42 (20) | 57 (18) |
| Number of prior systemic regimens in the metastatic setting, % | | | |
| 0 | 24 (24) | 42 (20) | 59 (19) |
| 1 | 36 (36) | 83 (40) | 124 (40) |
| 2 | 19 (19) | 41 (20) | 64 (21) |
| 3 | 11 (11) | 24 (12) | 39 (13) |
| ≥4 | 10 (10) | 17 (8) | 24 (8) |
| Intravesical bacillus Calmette-Guérin administered, n (%) | 15 (15) | 46 (22) | 73 (24) |

Efficacy

Figure 9A:
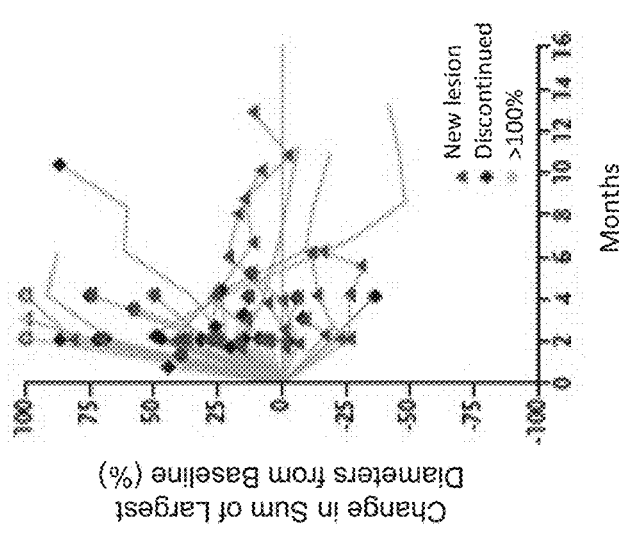
FIG. 9A is a graph depicting the change in sum of the largest diameters of tumors from baseline over time in the IC2/3 patients demonstrating a partial or complete response to atezolizumab (MPDL3280A).
Figure 9B:
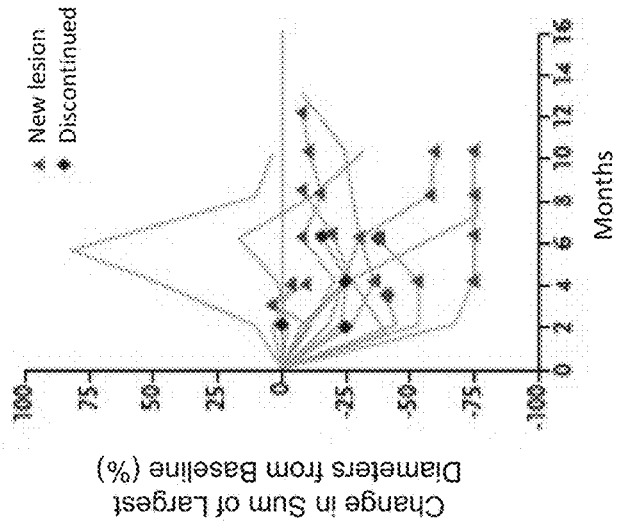
FIG. 9B is a graph depicting the change in sum of the largest diameters of tumors from baseline over time in the IC2/3 patients with stable disease to atezolizumab (MPDL3280A).
Figure 9C:
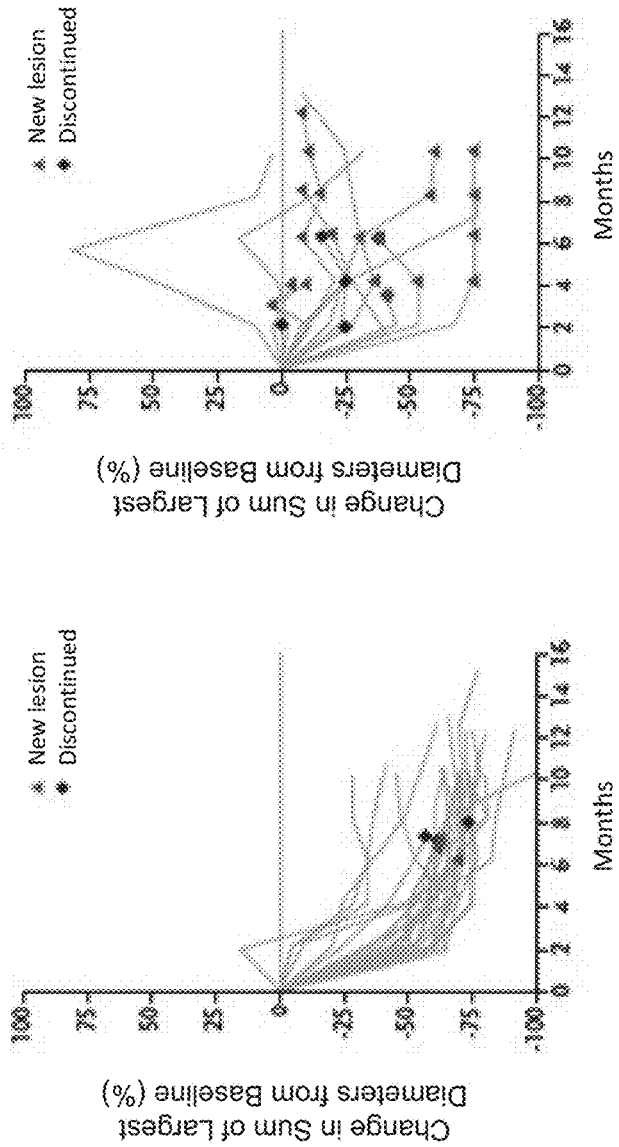
FIG. 9C is a graph depicting the change in sum of the largest diameters of tumors from baseline over time in the IC2/3 patients with progressive disease to atezolizumab (MPDL3280A).

The 24-week, pre-planned primary analysis demonstrated that treatment with atezolizumab resulted in a significantly improved RECIST v1.1 objective response rate (ORR) for each pre-specified IC group (IC2/3, 27% (95% CI 19 to 37), p<0.0001); IC1/2/3, 18% (95% CI 13 to 24), p=0.0004); and all patients, 15% (95% CI, 11 to 20), p=0.0058) compared to a historical control ORR of 10% (Table 5). The updated analysis of efficacy described herein was later conducted to assess the durability of response (Table 6). By independent radiological review (RECIST v1.1), the updated analysis of efficacy showed an ORR of 26% (95% CI, 18 to 36) in the IC2/3 group, including 11% of patients who achieved a complete response (CR). In the IC1/2/3 group, the ORR was 18% (95% CI, 13 to 24), with CR observed in 13 patients (6%). For all evaluable patients, the objective response rate was 15% (95% CI, 11 to 19); with complete response observed in 15 patients (5%). Investigator-assessed response rates (per modified RECIST) were similar to the RECIST v1.1 results (Table 6). With a median follow-up of 11.7 months, the median duration of response was not yet reached in any of the PD-L1 immunohistochemistry groups (range, 2.0*, 13.7* months, *censored values) (data for IC2/3 group is shown in FIGS. 9A-9C; IC0 and IC1 groups shown in FIGS. 10A-10F). At the time of the data cut-off, ongoing responses were observed in 38 of the 45 responding patients (84%). The median time to response was 2.1 months (95% CI, 2.0 to 2.2). From a multivariate logistic regression model of ORR on PD-L1 IC status and Bellmunt risk score, the odds ratio of having a confirmed responder by IRF per RECIST v1.1 is 4.12 (95% CI: 1.71, 9.90) for the IC2/3 group compared with the IC0 group and 1.30 (95% CI: 0.49, 3.47) for the IC1 group compared with the IC0 group, when Bellmunt risk score is controlled. The logistic regression results are consistent with the subgroup analyses.

Exploratory subset analysis of patients demonstrating complete response with regard to clinical factors demonstrates that the absence of visceral metastasis (e.g., lymph node-only disease) at baseline was associated with the highest complete response rate (CRR) (e.g., presence of visceral metastases (Yes/No): Yes (n=243), 1.2% (95% CI 0.26-3.57) vs 17.9% (95% CI, 9.61-29.20 for No (n=67). Analysis of the association of the primary tumor site with CRR was also conducted (e.g., bladder (n=230), 6.5% (95 CI, 3.70-10.53); renal/pelvis (n=42), 0% (95% CI, 0.00-8.41); ureter (n=23), 0% (95% CI, 0.00-14.82); urethra (n=5), 0% (95% CI, 0.00-52.18) and other (n=10), 0% (95% CI, 0.00, 30.85)). Additionally, the association of performance status with CRR was examined (e.g., ECOG PS of 0 (n=117), 8.5% (95% CI, 4.17-15.16) compared to 2.6% (95% CI, 0.85-5.94) for ECOG PS of 1 (n=193)). Finally, the association of IC PD-L1 status with CRR was analyzed (e.g., IC0 (n=103) 1.9% (95% CI, 0.24-6.84) compared to IC1 (n=107) 1.9% (95% CI, 0.23-6.59) compared to IC2/3 (n=100) 11% (95% CI, 5.62-18.83) compared to all patients (n=310) 4.8% (2.73-7.86)).

Analyses of ORR per IRF RECIST v.1.1 by primary compared to metastatic tissue specimens, were supportive of an association of PD-L1 IHC status and clinical response irrespective of anatomic site. Among the 311 patients in the primary analysis, 233 were assessed for PD-L1 expression based on tumor specimens obtained from the primary site of disease while 78 were assessed for PD-L1 expression in tumor specimens obtained from the metastatic site of disease. Among the patients who were assessed for PD-L1 expression on the basis of tissue from the primary sites of disease, the ORR per IRF RECIST v1.1 was 26% (95% CI 16 to 37), 18% (95% CI 12 to 25), and 16% (95% CI 11 to 21) for the IC2/3, IC1/2/3, and all-comer populations, respectively. Among the patients who were assessed for PD-L1 expression on the basis of tissue from metastatic sites of disease, the ORR per IRF RECIST v1.1 was 32% (95% CI 14 to 55), 20% (95% CI 10 to 35), and 14% (95% CI 7 to 24) for the IC2/3, IC1/2/3, and all-comer populations, respectively.

TABLE 5

Objective Response Rate by IC Score—RECIST v1.1 Criteria by Independent Review

| PD-L1 subgroup | n | CR (%) | ORR (%) | 95% CI | P value[b] |
|---|---|---|---|---|---|
| IC2/3 | 100 | 8% | 27% | 19, 37 | <0.0001 |
| IC1/2/3 | 208 | 5% | 18% | 13, 24 | 0.0004 |
| All | 311 | 4% | 15% | 11, 20 | 0.0058 |
| IC1 | 108 | 3% | 10% | 5, 18 | N/A |
| IC0 | 103 | 1% | 9% | 4, 16 | N/A |

[a]Objective response evaluable population: all treated patients had measurable disease at baseline per investigator-assessed RECIST v1.1.
[b]P-value for $H_o$: ORR = 10% versus $H_a$: ORR ≠ 10%, where 10% ORR is historical control, $\alpha = 0.05$.

TABLE 6

Efficacy of Response Rate

| PD-L1 Subgroup | n | ORR, n (%) (95% CI) | CR, n (%) | PR, n (%) | SD, n (%) | PD, n (%) |
|---|---|---|---|---|---|---|
| RECIST version 1.1 Criteria by Independent Review | | | | | | |
| IC2/3 | 100 | 26 (26) (18, 36) | 11 (11) | 15 (15) | 16 (16) | 44 (44) |
| IC1/2/3 | 207 | 37 (18) (13, 24) | 13 (6) | 24 (12) | 34 (16) | 107 (52) |
| All | 310 | 45 (15) (11, 19) | 15 (5) | 30 (10) | 59 (19) | 159 (51) |
| IC1 | 107 | 11 (10) (5, 18) | 2 (2) | 9 (8) | 18 (17) | 63 (59) |
| IC0 | 103 | 8 (8) (3, 15) | 2 (2) | 6 (6) | 25 (24) | 52 (51) |
| Modified RECIST Criteria by Investigator Review | | | | | | |
| IC2/3 | 100 | 27 (27) (19, 37) | 8 (8) | 19 (19) | 31 (31) | 28 (28) |
| IC1/2/3 | 207 | 45 (22) (16, 28) | 14 (7) | 31 (15) | 58 (28) | 74 (36) |
| All | 310 | 58 (19) (15, 24) | 16 (5) | 42 (14) | 92 (30) | 110 (35) |
| IC1 | 107 | 18 (17) (10, 25) | 6 (6) | 12 (11) | 27 (25) | 46 (43) |
| IC0 | 103 | 13 (13) (7, 21) | 2 (2) | 11 (11) | 34 (33) | 36 (35) |

Figure 11A:
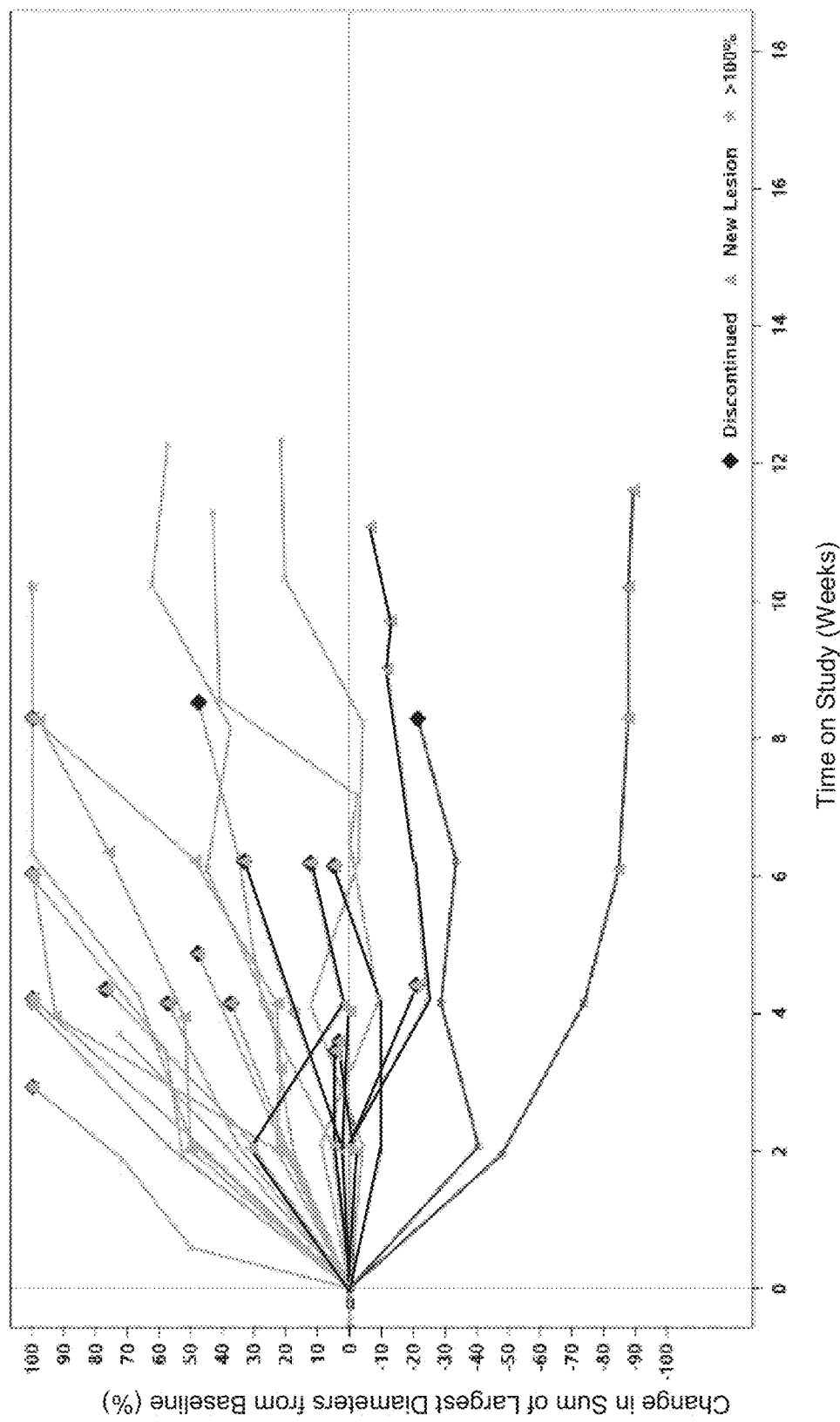
FIG. 11A is a graph depicting the change in sum of the longest diameters of tumors over time by the best response in the ICO patients treated beyond progression with atezolizumab. Medium gray lines=≤-30 (n=2), black lines=>-30 and ≤20 (n=8), light gray lines=>20 (n=17).
Figure 11B:
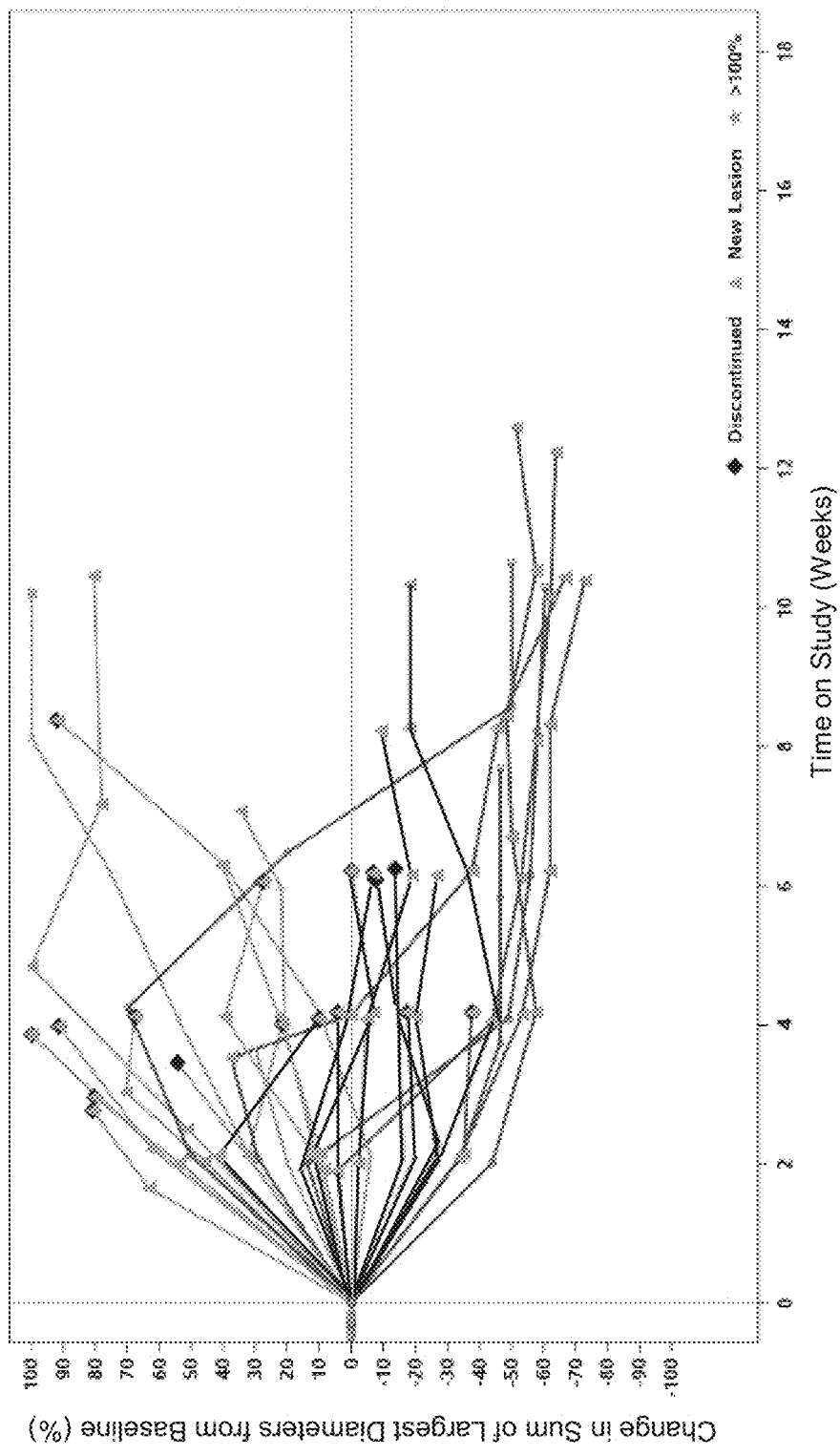
FIG. 11B is a graph depicting the change in sum of the longest diameters of tumors over time by the best response in the IC1 patients treated beyond progression with atezolizumab. Medium gray lines=≤-30 (n=8), black lines=>-30 and ≤20 (n=10), light gray lines=>20 (n=14).
Figure 11C:
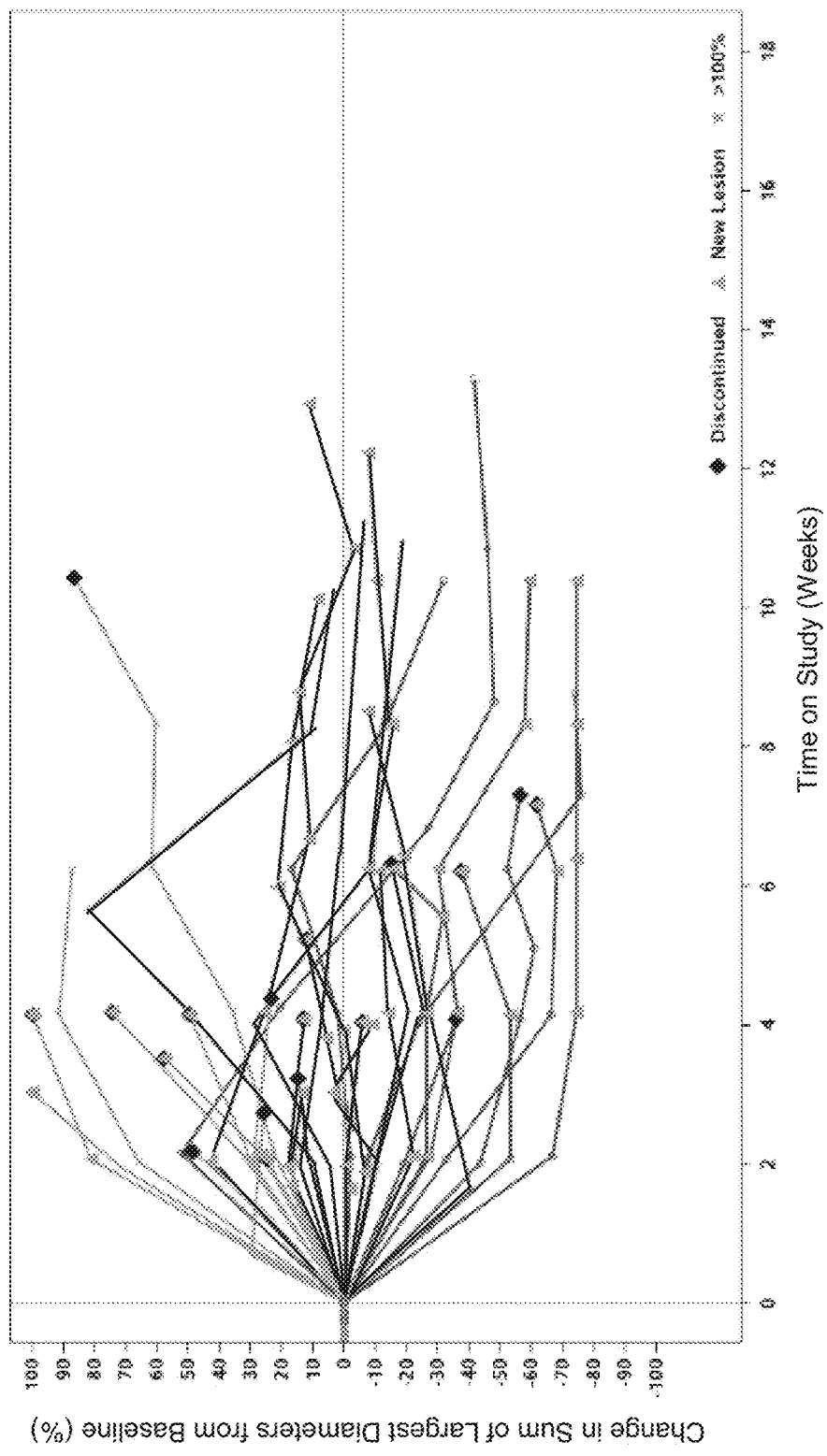
FIG. 11C is a graph depicting the change in sum of the longest diameters of tumors over time by the best response in the IC2/3 patients treated beyond progression with atezolizumab. Medium gray lines=≤-30 (n=10), black lines=>-30 and ≤20 (n=15), light gray lines=>20 (n=11).

To account for the occurrence of pseudoprogression, patients were allowed treatment beyond IRF RECIST v1.1 progression. 121 patients were treated beyond progression for a median of 7.8 weeks, and of these, 21 (17%) subsequently experienced target lesion reduction of at least 30% from their baseline scans as shown in FIG. 11B. Approximately 27% of patients treated beyond RECIST progression demonstrated stability of disease.

Durable responses observed included patients with upper tract disease and patients with poor prognostic features. While the presence of liver metastasis in patients resulted in a lower objective response rate compared to patients with no liver metastases (5% compared to 19%, Table 7), these responses were durable with the duration of response not reached at the time of the data cut-off. A similar trend was observed in patients with visceral metastases (10% vs 31% for patients with no visceral metastases) and ECOG PS 1 (8% compared to 25% for patients with ECOG PS 0). The median duration of response was not yet reached across any subgroup analyzed.

TABLE 7

Overall Response Rates by RECIST v1.1 and Modified RECIST for Patient Subgroups in IMvigor 210 (Updated Analysis. Data Cutoff Sep. 14, 2015)

| Patient Subgroup | Parameter | n | RECIST v1.1 Independent Reviewed ORR, n (%) | Modified RECIST— Investigator Assessed ORR, n (%) |
|---|---|---|---|---|
| Sex | Male | 241 | 40 (17) | 52 (22) |
| | Female | 69 | 5 (7) | 6 (9) |
| Age | <65 | 127 | 17 (13) | 20 (16) |
| | ≥65 | 183 | 28 (15) | 38 (21) |
| Race | Caucasian | 282 | 40 (14) | 49 (17) |
| | Other | 28 | 5 (18) | 9 (32) |
| ECOG PS | 0 | 117 | 29 (25) | 34 (29) |
| | 1 | 193 | 16 (8) | 24 (12) |
| Site of Primary Tumor | Bladder | 230 | 39 (17) | 50 (22) |
| | Renal pelvis | 42 | 3 (7) | 5 (12) |
| | Ureter | 23 | 2 (9) | 2 (9) |
| | Urethra | 5 | 0 (0) | 1 (20) |
| | Other | 10 | 1 (10) | 0 (0) |
| Lymph node only disease | Yes | 43 | 13 (30) | 18 (42) |
| | No | 267 | 32 (12) | 40 (15) |
| Liver metastasis | Yes | 96 | 5 (5) | 9 (9) |
| | No | 214 | 40 (19) | 49 (23) |
| Visceral metastasis | Yes | 243 | 24 (10) | 32 (13) |
| | No | 67 | 21 (31) | 26 (39) |

TABLE 7-continued

Overall Response Rates by RECIST v1.1 and Modified RECIST for Patient Subgroups in IMvigor 210 (Updated Analysis. Data Cutoff Sep. 14, 2015)

| Patient Subgroup | Parameter | n | RECIST v1.1 Independent Reviewed ORR, n (%) | Modified RECIST— Investigator Assessed ORR, n (%) |
|---|---|---|---|---|
| Hemoglobin < 10 g/dL | Yes | 69 | 5 (7) | 5 (7) |
|  | No | 241 | 40 (17) | 53 (22) |
| Baseline creatinine clearance | <60 ml/min | 110 | 13 (12) | 14 (13) |
|  | ≥60 ml/min | 172 | 26 (15) | 37 (22) |
|  | Unknown | 28 | 6 (21) | 7 (25) |
| Bellmunt risk factors, number | 0 | 83 | 24 (29) | 30 (36) |
|  | 1 | 117 | 16 (14) | 18 (15) |
|  | 2 | 89 | 5 (6) | 10 (11) |
|  | 3 | 21 | 0 (0) | 0 (0) |
| Prior therapy with platinum-based regimen | Cisplatin | 227 | 32 (14) | 46 (20) |
|  | Carboplatin | 80 | 13 (16) | 12 (15) |
|  | Other platinum | 3 | 0 (0) | 0 (0) |
| Number of prior systemic regimens in metastatic setting, number | 0 | 59 | 13 (22) | 15 (24) |
|  | 1 | 124 | 16 (13) | 24 (19) |
|  | 2 | 64 | 8 (13) | 9 (14) |
|  | 3 | 39 | 6 (15) | 7 (18) |
|  | ≥4 | 24 | 2 (8) | 3 (13) |
| Prior systemic regimen setting | Adjuvant or neoadjuvant with 1$^{st}$ PD ≤12 months | 57 | 13 (23) | 15 (26) |
|  | Adjuvant or neoadjuvant with 1$^{st}$ PD >12 months | 2 | 0 (0) | 0 (0) |
| Number of prior lines of therapy | 0 | 2 | 0 (0) | 0 (0) |
|  | 1 | 145 | 23 (16) | 31 (21) |
|  | 2 | 87 | 12 (14) | 15 (17) |
|  | 3 | 46 | 7 (15) | 8 (17) |
|  | ≥4 | 30 | 3 (10) | 4 (13) |
| Time from prior chemotherapy (≤3 months) | Yes | 121 | 13 (11) | 16 (13) |
|  | No | 189 | 32 (17) | 42 (22) |
| Prior BCG | Yes | 73 | 9 (12) | 9 (12) |
|  | No | 237 | 36 (15) | 49 (21) |
| PD-L1 expression by immunohistochemistry on tumor cells (TC score) | TC3 | 12 | 2 (17) | 2 (17) |
|  | TC2 | 28 | 5 (18) | 6 (21) |
|  | TC1 | 22 | 3 (14) | 5 (23) |
|  | TC0 | 248 | 35 (14) | 45 (18) |

With a median survival follow-up of approximately 11.7 months (range, 0.2* to 15.2; *denotes a censored value), the median progression-free survival (PFS) (RECIST v1.1) was 2.1 months among all patients (95% CI, 2.1 to 2.1) and similar across all IC groups. The investigator-assessed median PFS by modified RECIST criteria was 4.0 months (95% CI, 2.6 to 5.9) in the IC2/3 group compared to 2.9 months (95% CI, 2.1 to 4.1) in the IC1/2/3 group and 2.7 months (95% CI, 2.1 to 3.9) in all patients.

Figure 9D:
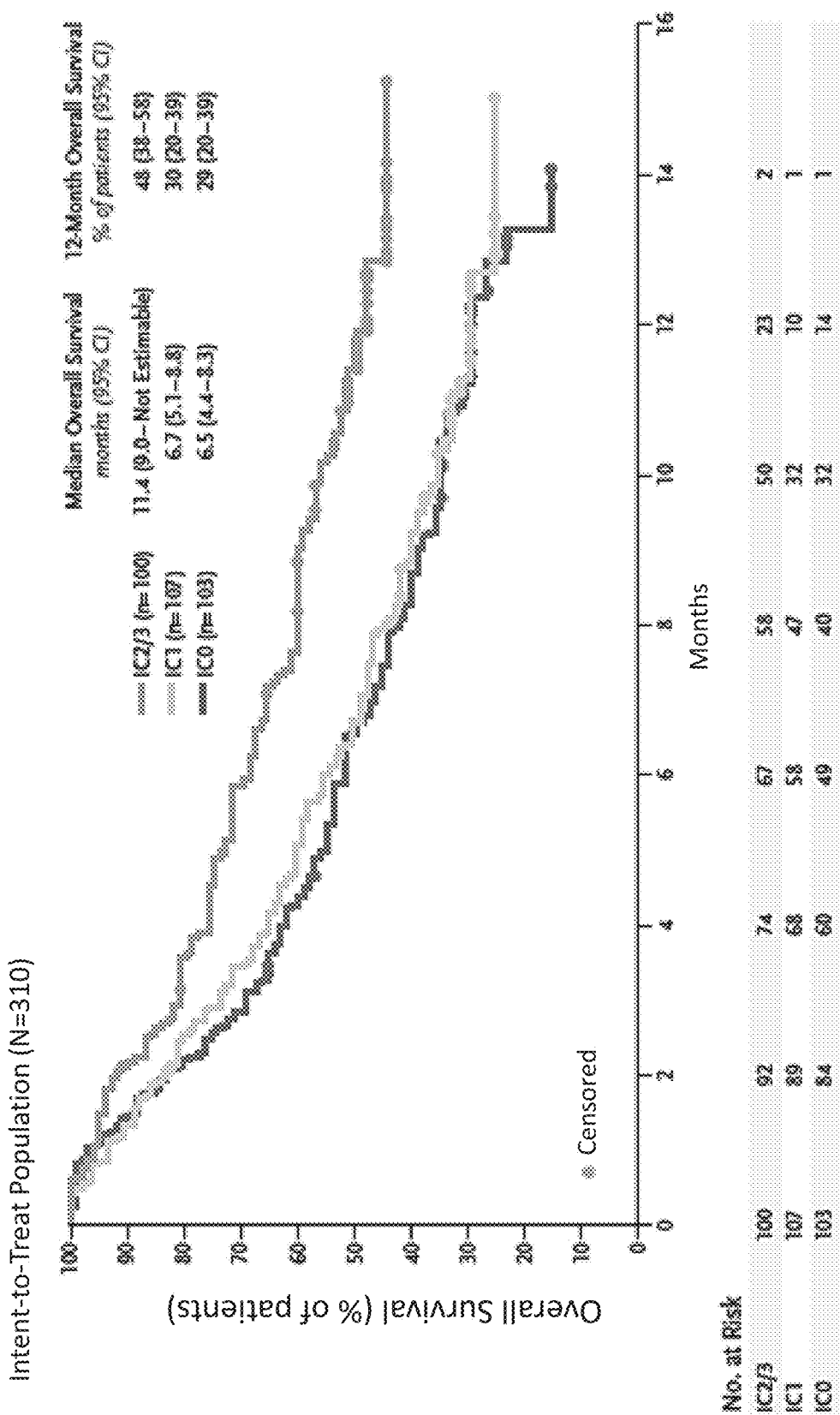
FIG. 9D is a graph depicting the overall survival of the ICO, IC1, and IC2/3 patients.
Figure 10A:
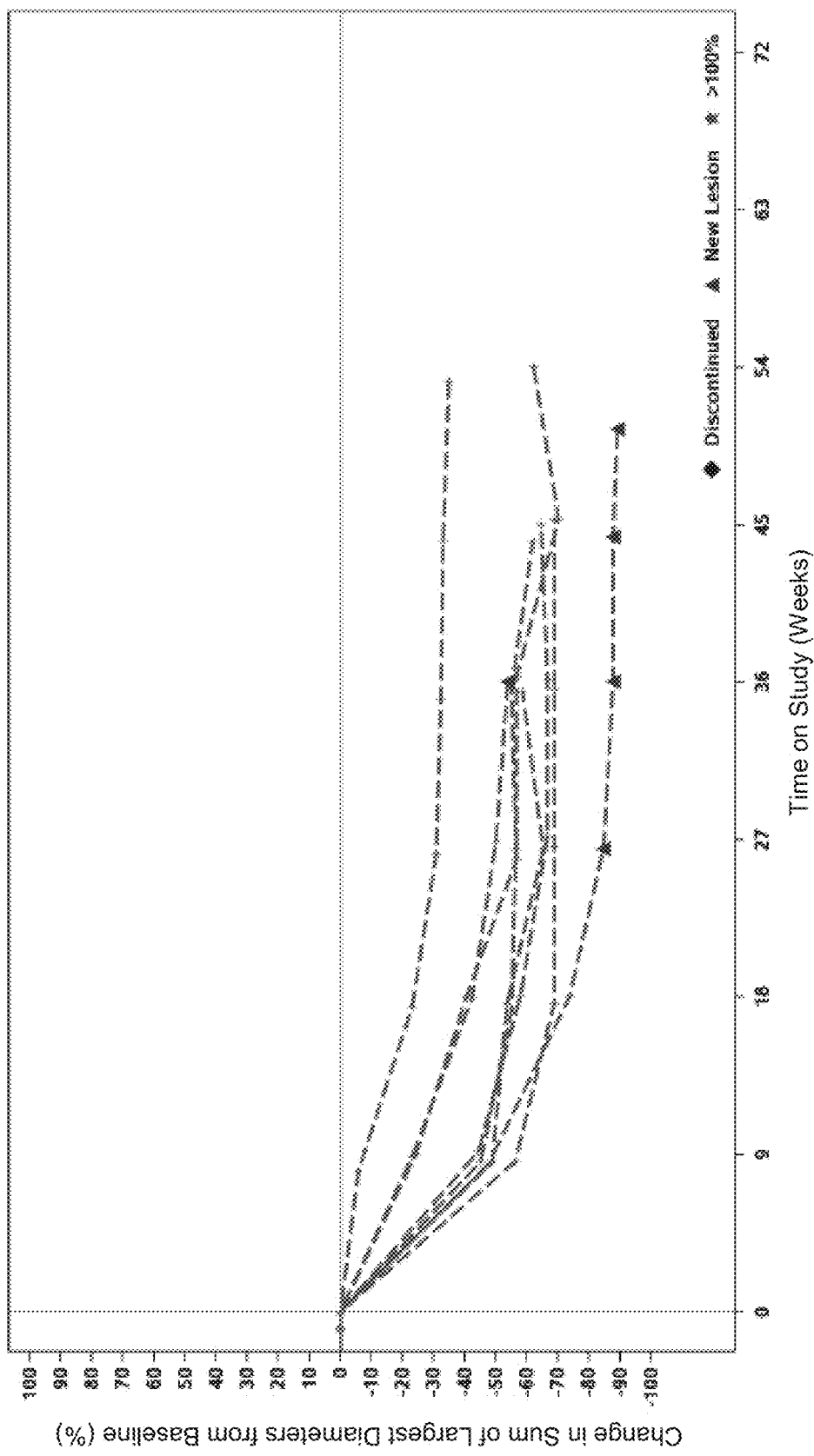
FIG. 10A is a graph depicting the sum of the longest diameters of tumors from baseline over in the ICO patients with response to treated with atezolizumab. Green dashed lines=PR/CR (n=8).
Figure 10B:
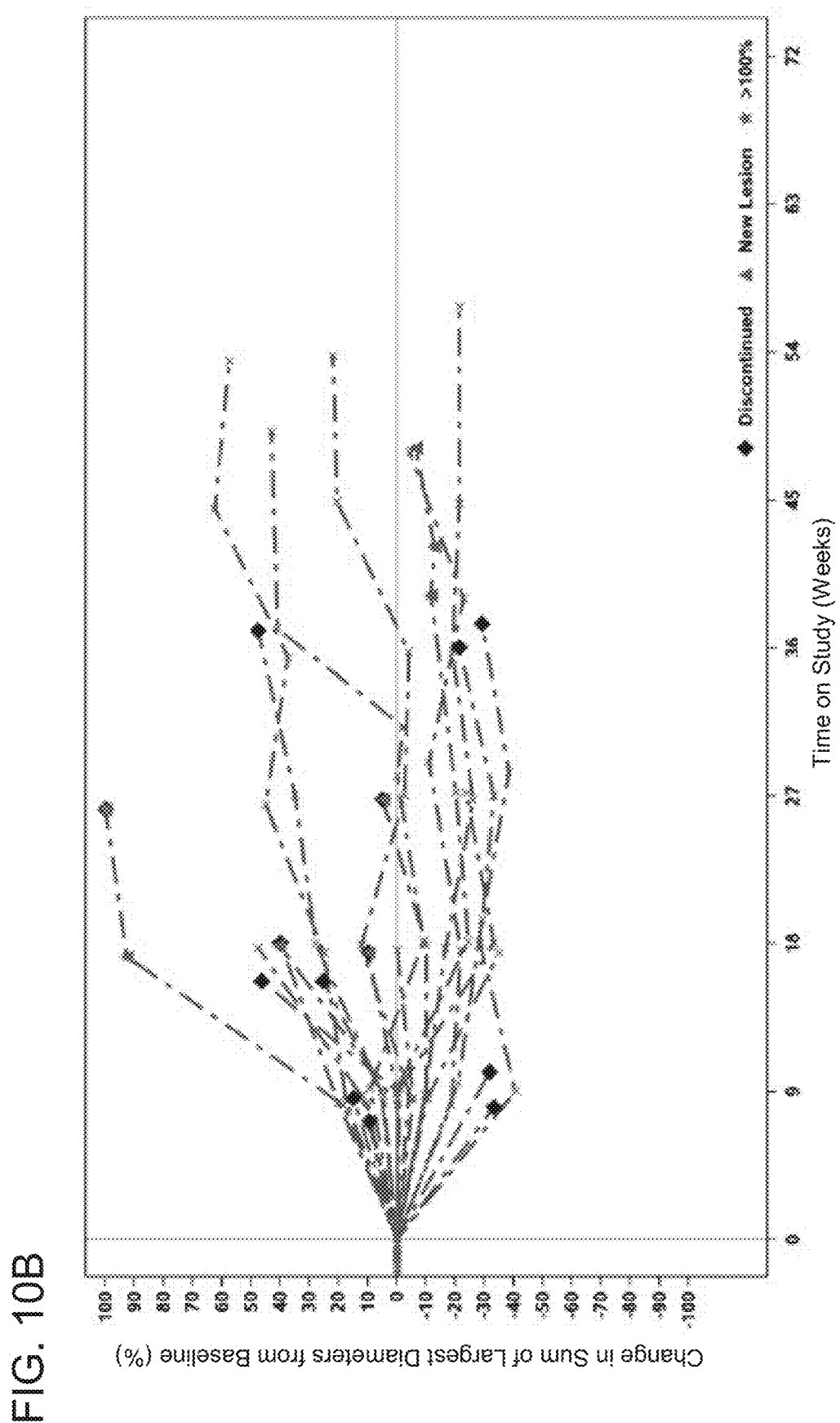
FIG. 10B is a graph depicting the sum of the longest diameters of tumors from baseline over in the ICO patients with stable disease treated with atezolizumab. Blue dashed lines=SD (n=25).
Figure 10C:
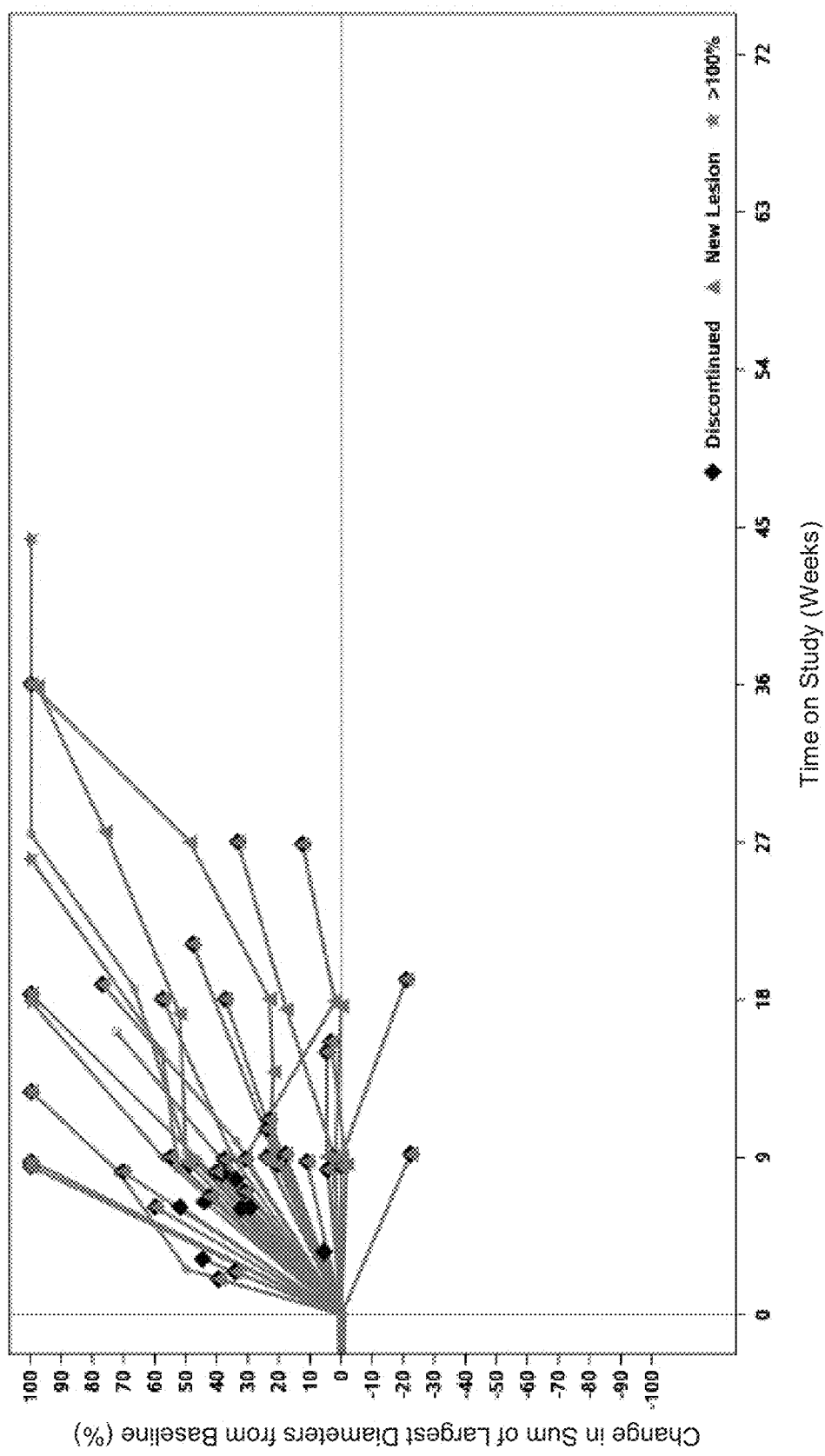
FIG. 10C is a graph depicting the sum of the longest diameters of tumors from baseline over in the ICO patients with progressive disease treated with atezolizumab. Red lines=PD (n=52).
Figure 10D:
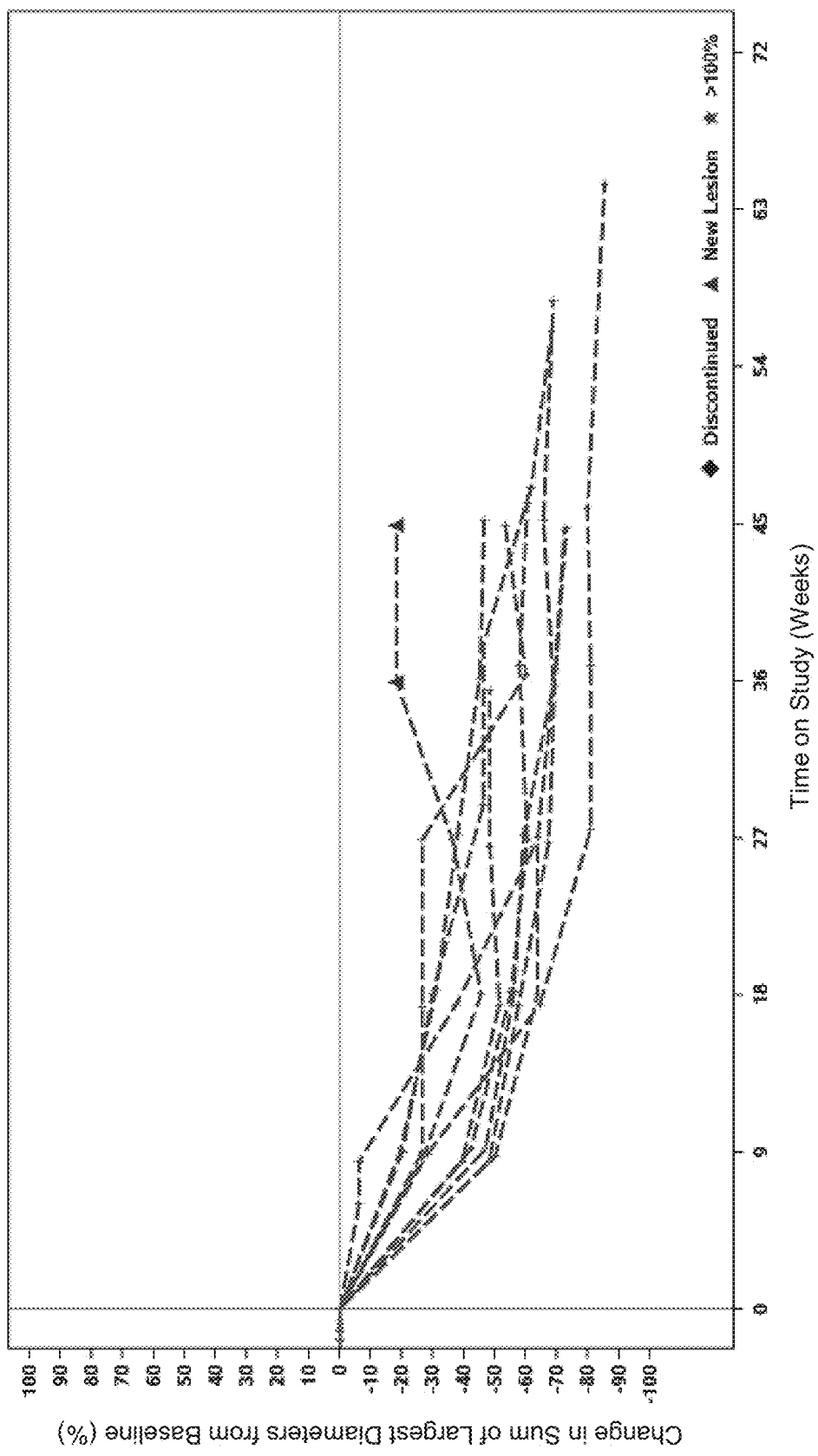
FIG. 10D is a graph depicting the sum of the longest diameters of tumors from baseline over in the IC1 patients with response to treated with atezolizumab. Green dashed lines=PR/CR (n=1).
Figure 10E:
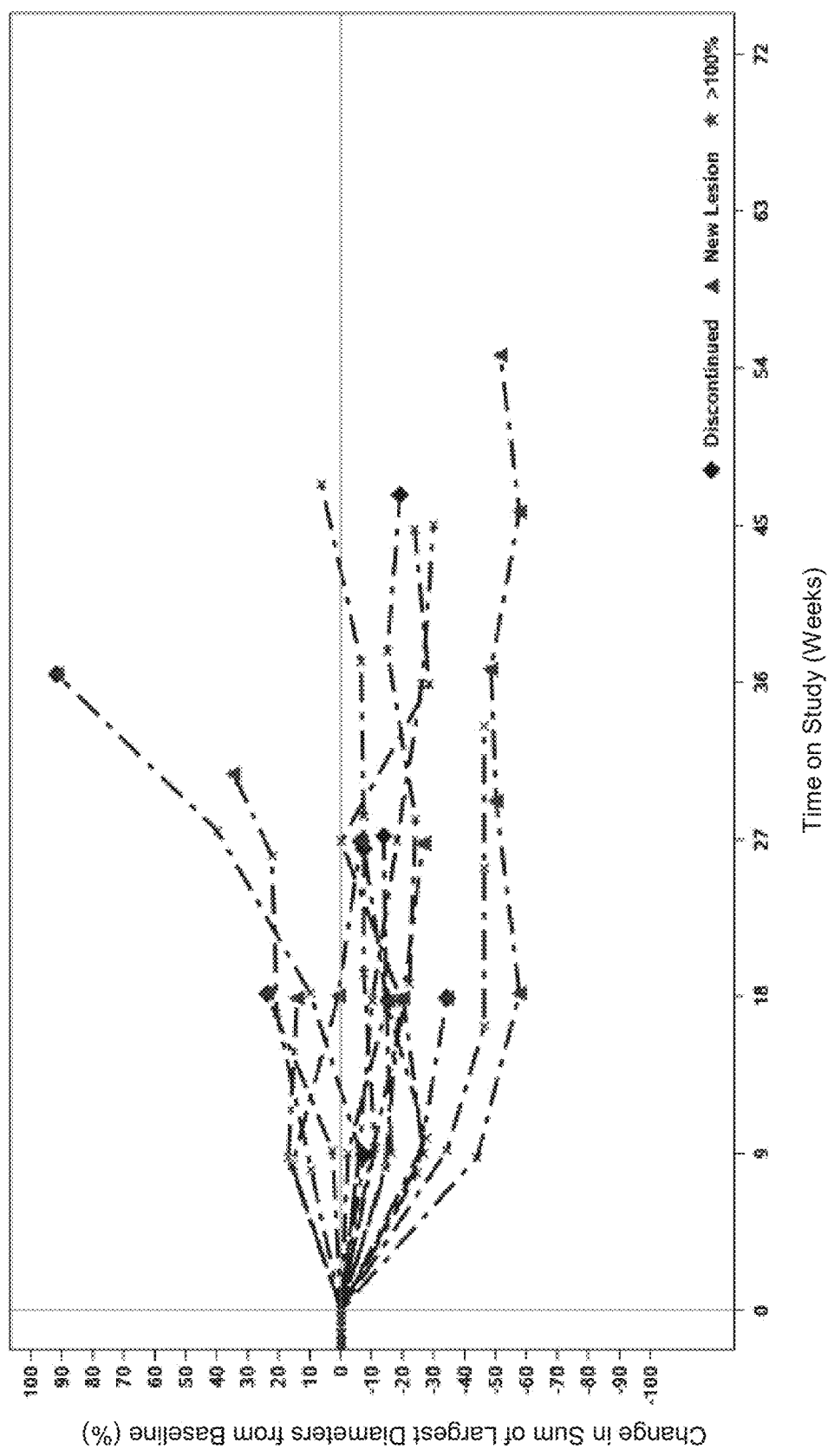
FIG. 10E is a graph depicting the sum of the longest diameters of tumors from baseline over in the IC1 patients with stable disease treated with atezolizumab. Blue dashed lines=SD (n=18).
Figure 10F:
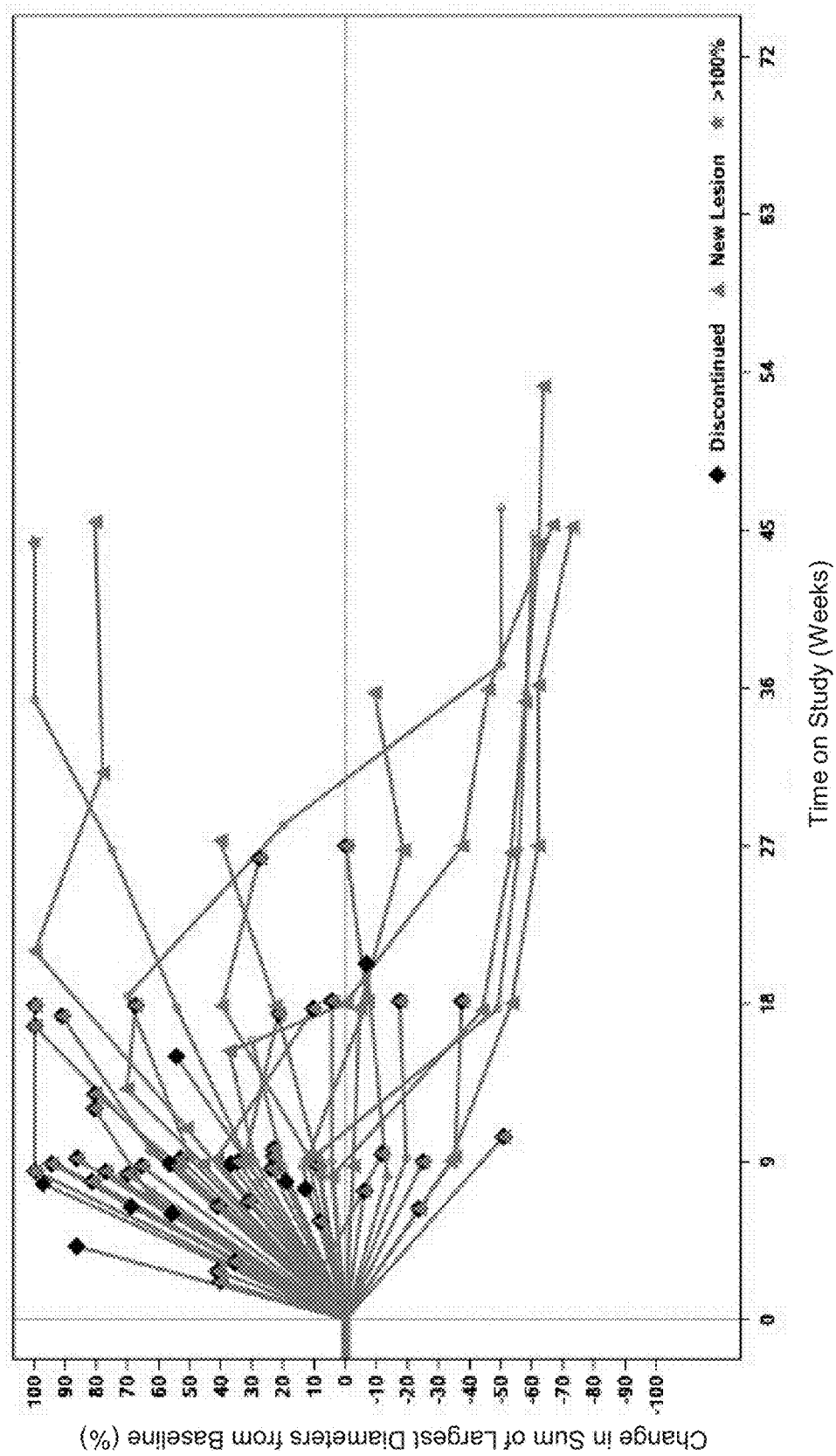
FIG. 10F is a graph depicting the sum of the longest diameters of tumors from baseline over in the IC1 patients with progressive disease treated with atezolizumab. Red lines=PD (n=61).

The median overall survival was 11.4 months (95% CI, 9.0 to not estimable) for the IC2/3 group, 8.8 months (95% CI, 7.1 to 10.6) in the IC1/2/3 group, and 7.9 months (95% CI, 6.6 to 9.3) for the entire cohort of patients (FIG. 9D). The 12-month landmark overall survival rate was 48% in the IC2/3 (95% CI, 38 to 58) group, 39% in the IC1/2/3 (95% CI, 32 to 46) group, and 36% (95% CI, 30 to 41) in the intent to treat population. In patients who received only one prior line of therapy (n=124) in the metastatic setting and no prior adjuvant/neoadjuvant therapy, the median overall survival was not estimable (95% CI, 9.3 to not estimable) for the IC2/3 group, 10.3 months (95% CI, 7.5 to 12.7) in the IC1/2/3 group, and 9.0 months (95% CI, 7.1 to 10.9) for the entire second-line population.

Safety The median duration of treatment was 12 weeks (range, 0 to 66). All cause, any grade adverse events were reported in 97% of patients, with 55% of patients experiencing a grade 3-4 event (see Table 9).

Sixty-nine percent of patients had a treatment-related adverse event (AE) of any grade, and 16% of patients had a grade 3-4 related event. Treatment-related serious adverse events were observed in 11% of patients.

There were no treatment-related deaths reported on study. The majority of treatment-related adverse events were mild to moderate in nature, with fatigue (30%), nausea (14%), decreased appetite (12%) pruritus (10%), pyrexia (9%), diarrhea (8%), rash (7%), and arthralgia (7%) among the most common any grade events (Table 8; see Table 9 for all cause adverse events). The incidence of grade 3-4 treatment-related adverse events was low with fatigue the most commonly occurring at 2% (Table 8). There were no reports of febrile neutropenia.

TABLE 8

Treatment Related Adverse Events Occuring in 310 Patients Receiving Atezolizumab

| Event | All Grade n (%) | Grade 3-4 n (%) |
|---|---|---|
| Any AE | 215 (69) | 50 (16) |
| Fatigue | 93 (30) | 5 (2) |
| Nausea | 42 (14) | 0 (0) |
| Decreased Appetite | 36 (12) | 2 (1) |
| Pruritis | 31 (10) | 1 (<1) |

TABLE 8-continued

Treatment Related Adverse Events Occuring in 310
Patients Receiving Atezolizumab

| Event | All Grade n (%) | Grade 3-4 n (%) |
|---|---|---|
| Pyrexia | 28 (9) | 1 (<1) |
| Diarrhea | 24 (8) | 1 (<1) |
| Rash | 23 (7) | 1 (<1) |
| Arthralgia | 21 (7) | 2 (1) |
| Vomiting | 18 (6) | 1 (<1) |
| Dyspnea | 10 (3) | 2 (1) |
| Anemia | 9 (3) | 3 (1) |
| Aspartate aminotransferase increased | 10 (3) | 2 (1) |
| Pneumonitis | 7 (2) | 2 (1) |
| Hypotension | 5 (2) | 2 (1) |
| Hypertension | 3 (1) | 3 (1) |

TABLE 9

All Causes Adverse Events Occurring in 310
Patients Receiving Atezolizumab

| AE, n (%) (N = 310) | Any Grade | Grade 3-4 |
|---|---|---|
| Any AE | 300 (97) | 170 (55) |
| Fatigue | 152 (49) | 18 (6) |
| Nausea | 81 (26) | 7 (2) |
| Decreased Appetite | 82 (27) | 4 (1) |
| Pruritis | 41 (13) | 1 (<1) |
| Pyrexia | 68 (22) | 2 (<1) |
| Diarrhea | 61 (20) | 3 (1) |
| Rash | 32 (10) | 1 (<1) |
| Arthralgia | 52 (17) | 3 (1) |
| Vomiting | 55 (18) | 4 (1) |
| Dyspnea | 53 (17) | 11 (4) |
| Anemia | 48 (15) | 28 (9) |
| Aspartate aminotransferase increased | 16 (5) | 3 (1) |
| Pneumonitis | 7 (2) | 2 (1) |
| Hypotension | 13 (4) | 3 (1) |
| Hypertension | 11 (4) | 6 (2) |

Seven percent of patients had an immune-mediated adverse event of any grade, with pneumonitis (2%), increased aspartate aminotransferase (1%), increased alanine aminotransferase (1%) and rash (1%) being the most common adverse events. Five percent had a grade 3-4 immune-mediated adverse event (all cause). No immune-mediated renal toxicity was observed. 30% of patients had an adverse event leading to dose interruption. Four percent of patients experienced an adverse event that lead to treatment withdrawal. 22% (69/310) of patients had an adverse event requiring steroid use.

Figure 12B:
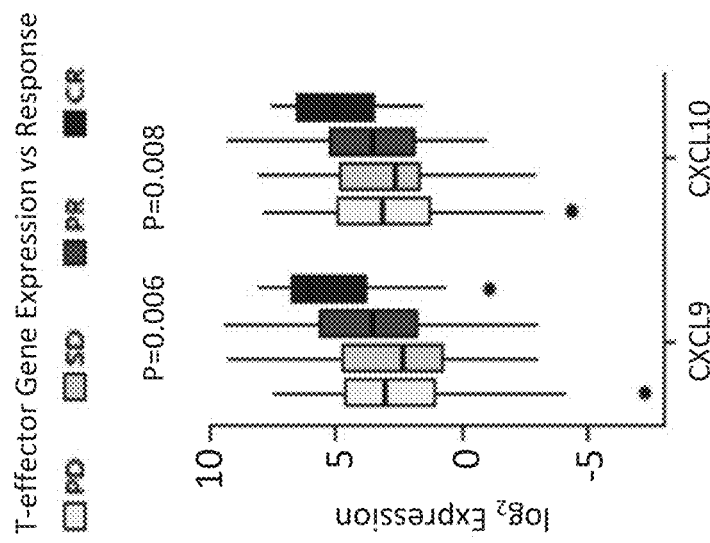
FIG. 12B is a graph depicting the association between PD-L1 immunohistochemistry expression (e.g., IC score) with genes in a CD8 effector set (e.g., CXCL9 and CXCL10).
Figure 12A:
FIG. 12A is a graph depicting the association between PD-L1 immunohistochemistry expression (e.g., IC score) and genes in a CD8 effector set (e.g., CXCL9 and CXCL10).
Figure 12A:
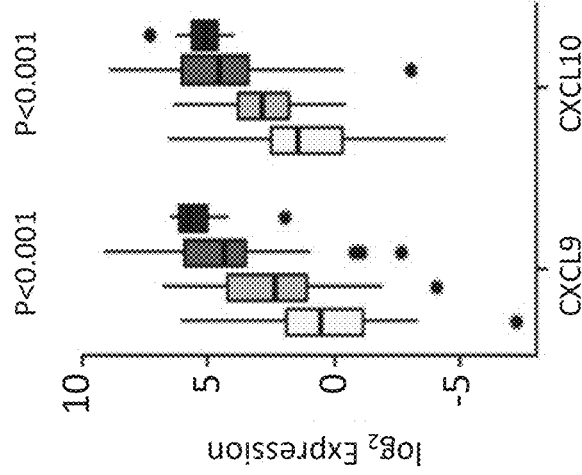
Figure 12C:
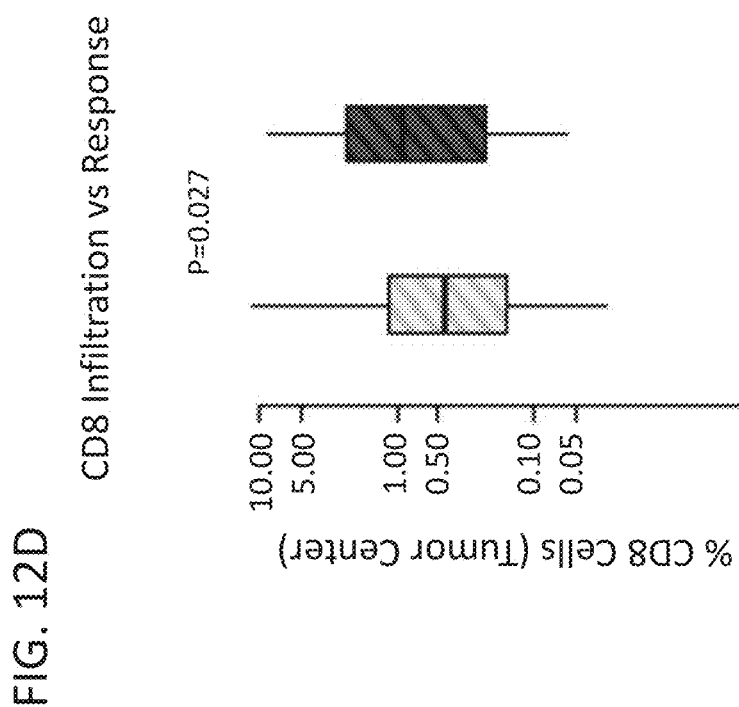
FIG. 12C is a graph depicting the association between CD8 infiltration and PD-L1 immunohistochemistry expression (e.g., IC score).
Figure 12D:
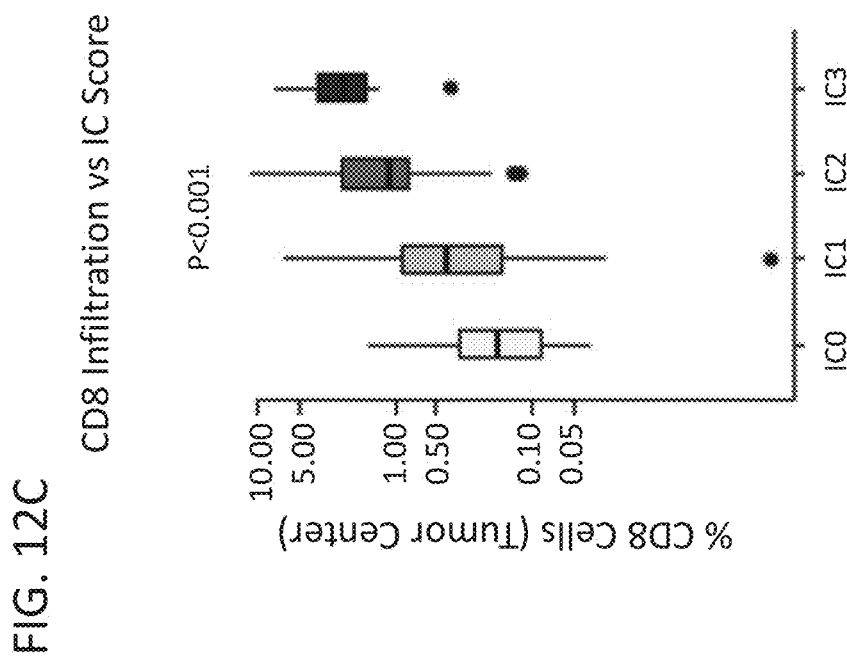
FIG. 12D is a graph depicting the association between CD8 infiltration and response.
Figure 13A:
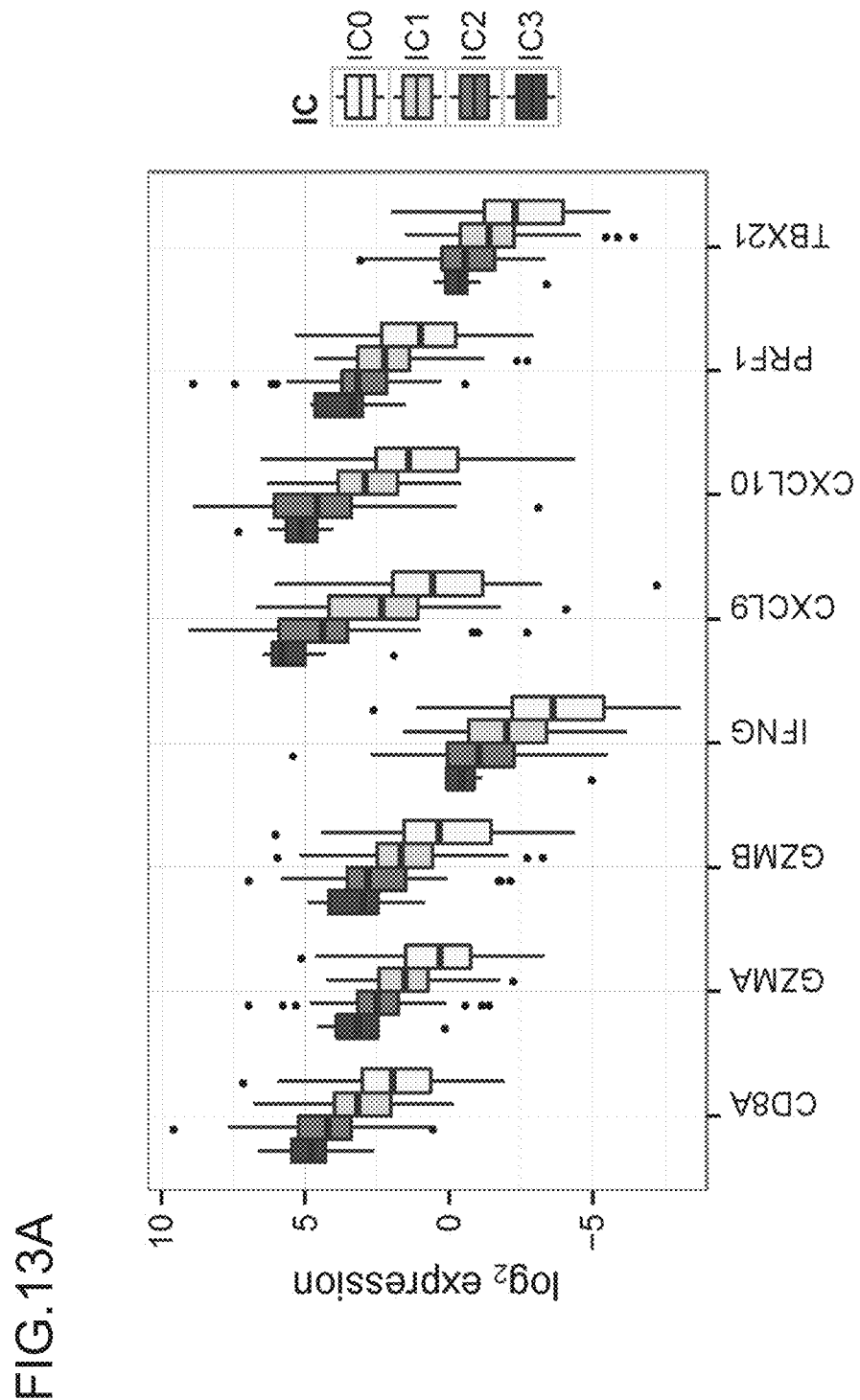
FIG. 13A is a graph depicting the association of a full CD8 T-effector gene set (e.g., CD8A, GZMA, GZMB, IFNG, CXCL9, CXCL10, PRF1, TBX21) with PD-L1 immunohistochemistry IC status
Figure 13B:
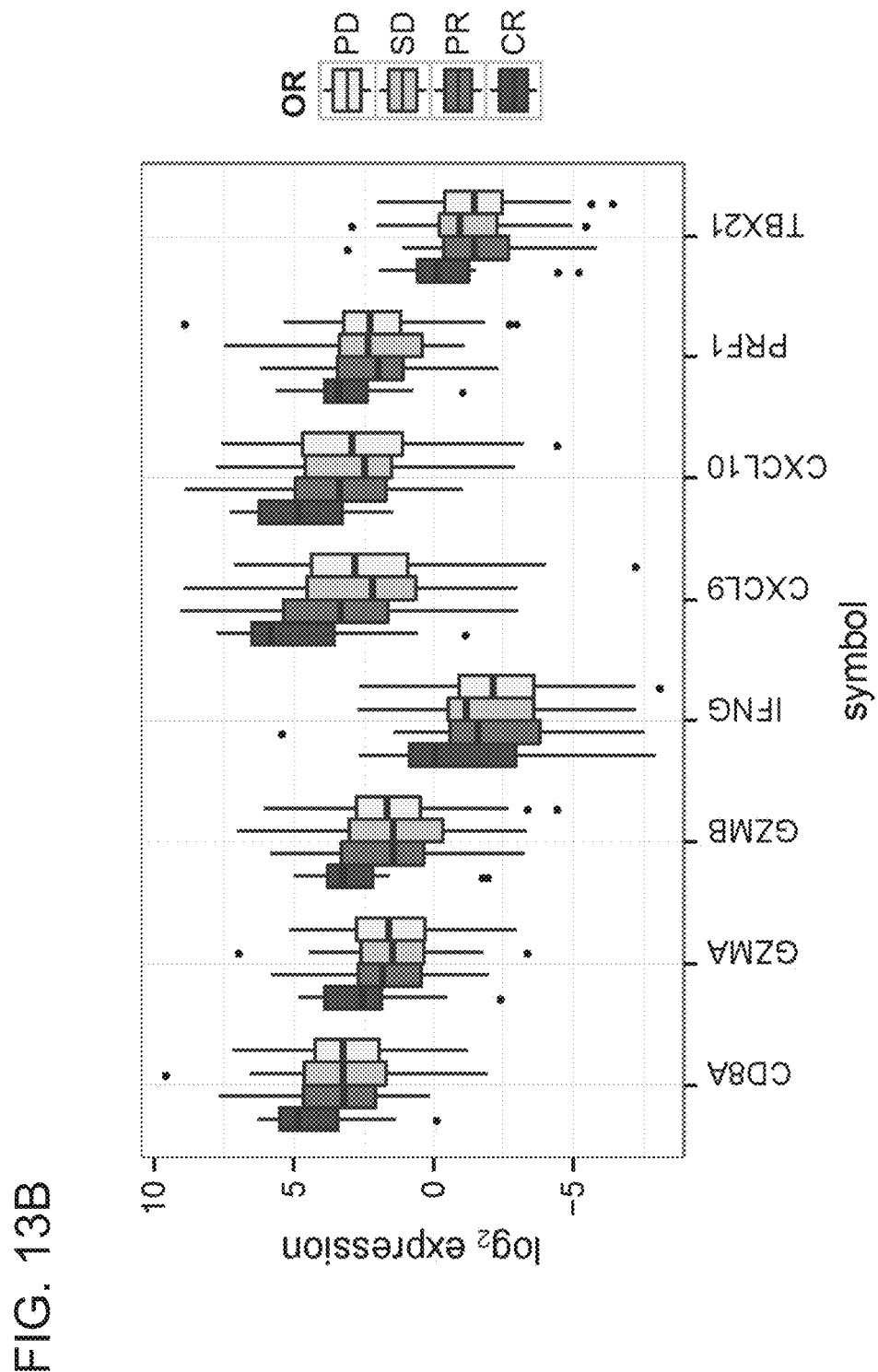
FIG. 13B is a graph depicting the association of a full CD8 T-effector gene set (e.g., CD8A, GZMA, GZMB, IFNG, CXCL9, CXCL10, PRF1, TBX21) with patient response.

Exploratory biomarkers PD-L1 immunohistochemistry expression on tumor infiltrating immune cells (IC) was associated with expression of genes in a CD8 T effector set ($T_{eff}$) (FIG. 12A). Among genes in the $T_{eff}$ set, responses to atezolizumab were most closely associated with high expression of two interferon-y-inducible T helper 1 ($T_H1$)-type chemokines, CXCL9 (P=0.0057) and CXCL10 (P=0.0079) (FIG. 12B). A similar, though less pronounced, trend was also seen with respect to other genes in the set (FIG. 13A). Consistent with increased T-cell trafficking chemokine expression, tumor CD8+ T cell infiltration was also associated with both PD-L1 IC (FIG. 12C, P<0.001) and response to atezolizumab (FIG. 12D, P=0.027).

Figure 12F:
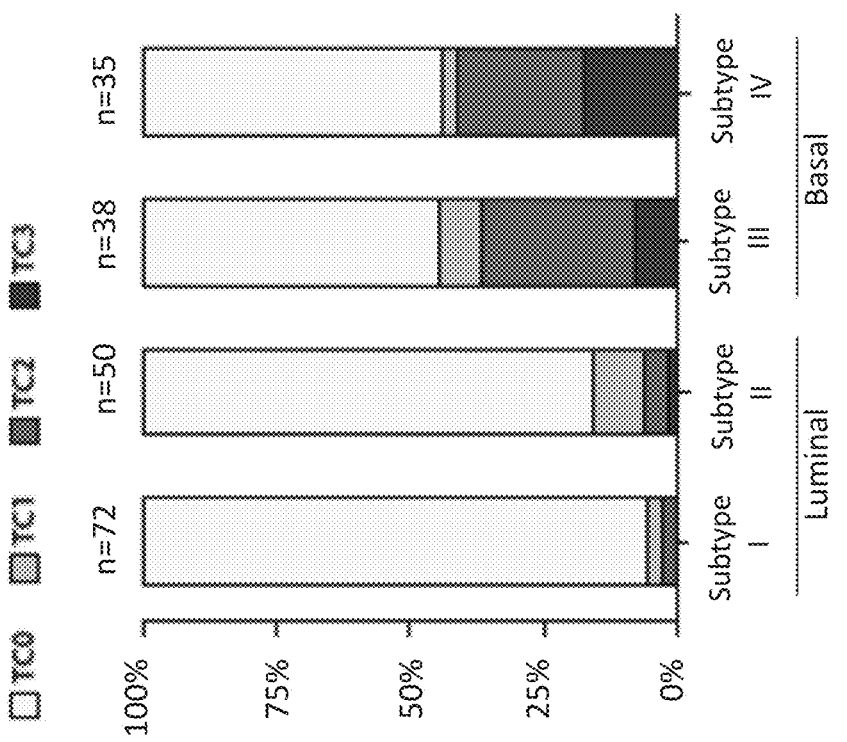
FIG. 12F is a graph depicting the association between PD-L1 immunohistochemistry expression on tumor cells (TC) with tumor subtype.
Figure 12E:
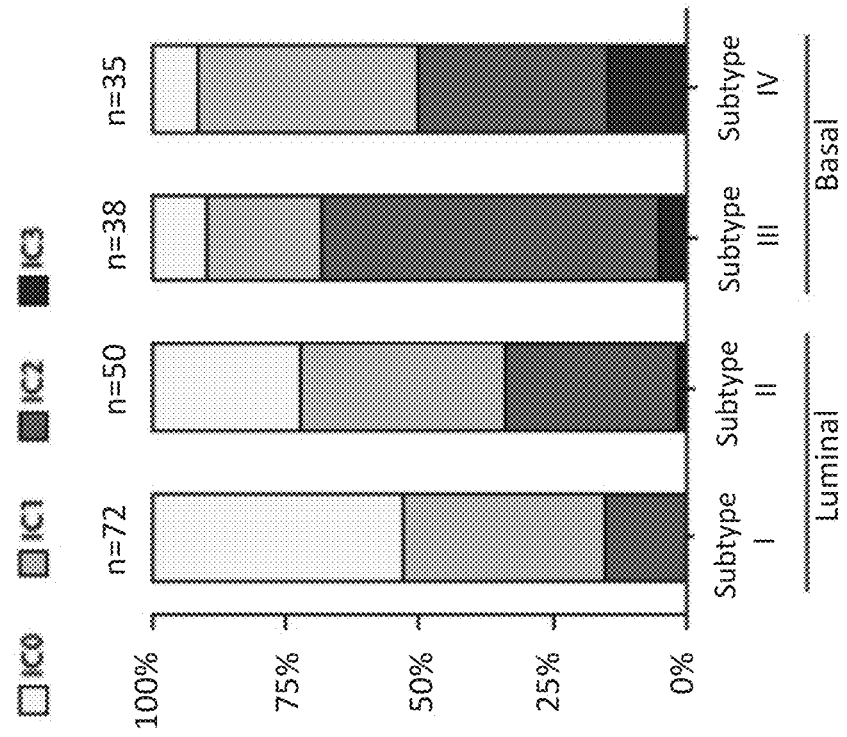
FIG. 12E a graph depicting the association between PD-L1 immunohistochemistry expression on tumor infiltrating immune cells (IC) tumor subtype.
Figure 14:
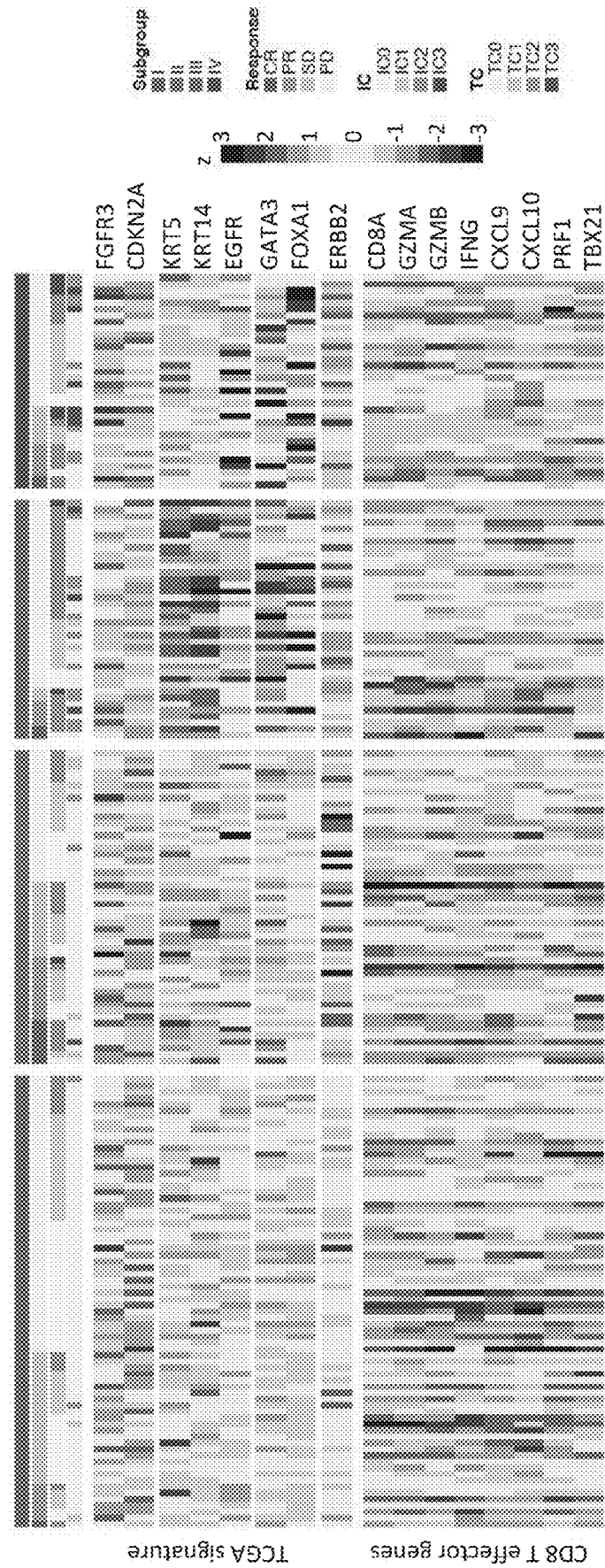
FIG. 14 is a heatmap depicting the relationship between inferred molecular subtype, response, IC and TC score, and gene expression for two gene sets: (i) genes used for assigning TCGA subtype and (ii) genes commonly associated with CD8 T effector activity.

Gene expression analysis (n=195) was used to classify patients into luminal (n=73) and basal (n=122) subtypes as defined by TCGA (FIG. 14). PD-L1 IC prevalence was highly enriched in the basal subtype versus the luminal subtype (60% vs. 23%, P<0.001, FIG. 12E) with IC2/3 expression of 15% in the papillary-like luminal cluster I, 34% in the cluster II, 68% in the squamous-like basal cluster III, and 50% in the basal cluster IV subtype. In contrast, PD-L1 tumor cell TC2/3 expression was almost exclusively seen in the basal subtype (39% in basal vs 4% in luminal, P<0.001; FIG. 12F) and did not correlate with ORR.

Figure 12G:
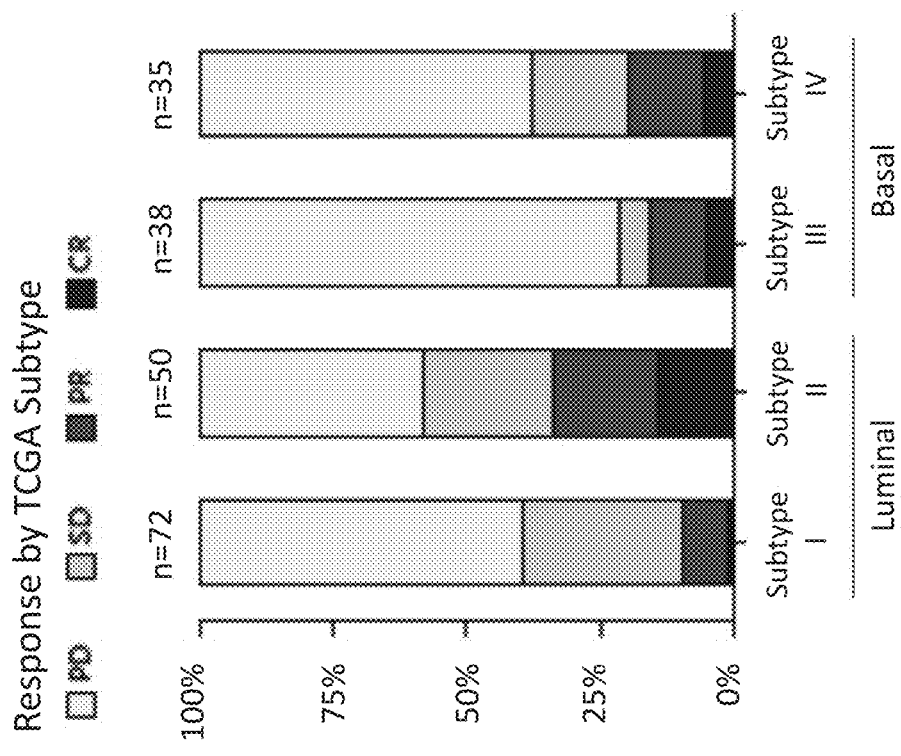
FIG. 12G a graph depicting the association between tumor subtype and response.

Consistent with PD-L1 IC2/3 expression, CD8 T-effector gene expression was elevated in luminal cluster II and basal cluster III/IV and not in luminal cluster I (FIG. 14). Response to atezolizumab occurred in all TCGA subtypes but was unexpectedly significantly higher in the luminal cluster II subtype than in other subtypes, which demonstrated an objective response rate of 34% (P=0.0017, FIG. 12G).

Discussion

Since the development of combination treatment with methotrexate, vinblastine, doxorubicin, and cisplatin chemotherapy 30 years ago, there have been no major improvements in the treatment outcomes for patients with urothelial carcinoma (see Sternberg et al. *J. Urol.* 133:403-7, 1985). The results of this large single arm Phase 2 study show that monotherapy atezolizumab induced durable anti-tumor responses in patients with advanced urothelial carcinoma whose tumors have progressed during or after platinum-based chemotherapy. This trial included heavily pre-treated patients and notably, the median duration of response had not been reached despite a median follow-up of 11.7 months. The low incidence of clinically relevant treatment-related adverse events makes atezolizumab widely applicable in this patient population who often have multiple co-morbidities and/or renal impairment. This durable efficacy and tolerability is striking in comparison to outcomes observed with currently available second-line chemotherapy (see Bellmunt et al *J. Clin. Oncol.* 27:4454-61,2009; Choueiri et al. *J. Clin. Oncol.* 30:507-12, 2012; Bambury et al. *Oncologist* 20:508-15, 2015).

The 12-month OS rate in the entire cohort that included approximately 42% of patients treated in the third- or later-line was 48% (95% CI, 38 to 58) in the IC2/3 group, 39% in the IC1/2/3 (95% CI, 32 to 46), group and 36% (95% CI, 30 to 41) in the ITT population. These OS results compare favorably to a landmark 12-month survival rate of 20% (95% CI, 17 to 24) from a pooled analysis of ten Phase 2 trials that evaluated 646 patients who received second-line chemotherapy or biologics (see Agarwal et al. *Clin. Genitourin. Cancer* 12:130-7, 2014).

Currently, the prognostic value of PD-L1 IC expression is unknown, with conflicting reports in the literature, although it does not appear to be associated with validated adverse risk factors in this data set (see Boorjian et al. *Clin. Cancer Res.* 14:4800-8, 2008; Bellmunt et al. *Ann. Oncol.* 26:812-7; 2015). Therefore, it appears likely that the improved survival in this patient population is related to atezolizumab treatment. Nonetheless, the results of ongoing randomized studies (NCT02302807) are needed to appropriately assess the prognostic and predictive value of the Ventana SP142 immunohistochemistry assay and to better understand which patients derive clinical benefit.

Responses to atezolizumab were associated with both conventional RECIST as well as atypical response kinetics, with an additional 17% of patients treated beyond progression having shrinkage of target lesions following RECIST v1.1 progression. The median progression-free survival was similar across the immunohistochemistry subsets with RECIST v1.1; however, it increased when modified RECIST criteria were utilized to account for the non-classical responses that may be observed with cancer immunotherapy.

In this study, a disconnect between PFS and OS was observed, similar to other immune checkpoint agents in other diseases, further suggesting that modifications of RECIST v1.1 are needed to better capture the benefit of immunotherapy treatment.

This study required a tumor specimen to be submitted during screening for prospective PD-L1 testing using the SP142. In a pre-specified analysis, higher levels of PD-L1 immunohistochemistry expression on immune cells were associated with a higher response rate to atezolizumab and longer overall survival. In contrast, the frequency of PD-L1 expression on tumor cells was low and did not show an association with objective response, lending further support to the importance of adaptive immunity in driving clinical benefit to immune checkpoint inhibitors.

Similarly, the association of immune activation gene subsets (e.g., CXCL9 and CD8A) and other immune checkpoint genes (PD-L1, CTLA-4, and TIGIT, data not shown) with IC but not TC PD-L1 expression suggests that the IC PD-L1 expression represents adaptive immune regulation and the presence of a pre-existing (but suppressed) immune response in urothelial carcinoma tumors (see Herbst et al. *Nature* 515:563-7, 2014). The presence of other negative regulators (e.g., TIGIT) further suggests that combination immunotherapeutic approaches may further enhance responses.

Interestingly, the molecular subtypes identified by the TCGA analysis were also associated with response to atezolizumab, suggesting that in addition to PD-L1 expression, subtypes differed in underlying immune biology. While responses were observed across all TCGA subtypes, significantly higher response rates were observed in the luminal cluster II subtype, which was characterized by transcriptional signatures associated with the presence of activated T effector cells. In contrast, luminal cluster I was associated with low expression of CD8+ effector genes, lower PD-L1 IC/TC expression, and lower responses to atezolizumab, consistent with a landscape often devoid of pre-existing immune activity. Basal clusters III and IV were also associated with increased PD-L1 IC expression as well as CD8+ effector genes. However, unlike luminal cluster II, basal clusters III/IV also exhibited high PD-L1 TC expression. The reduced response rates in the basal subtypes compared to luminal cluster II strongly suggest that other immunosuppressive factors exist in the basal subtypes that prevent effective T cell activation with inhibition of the PD-L1/PD-1 pathway. The differences in the immune landscape of luminal versus basal subtypes highlight the need to further understand the underlying immune biology to develop future rational combination or sequential treatment strategies.

Figure 15:
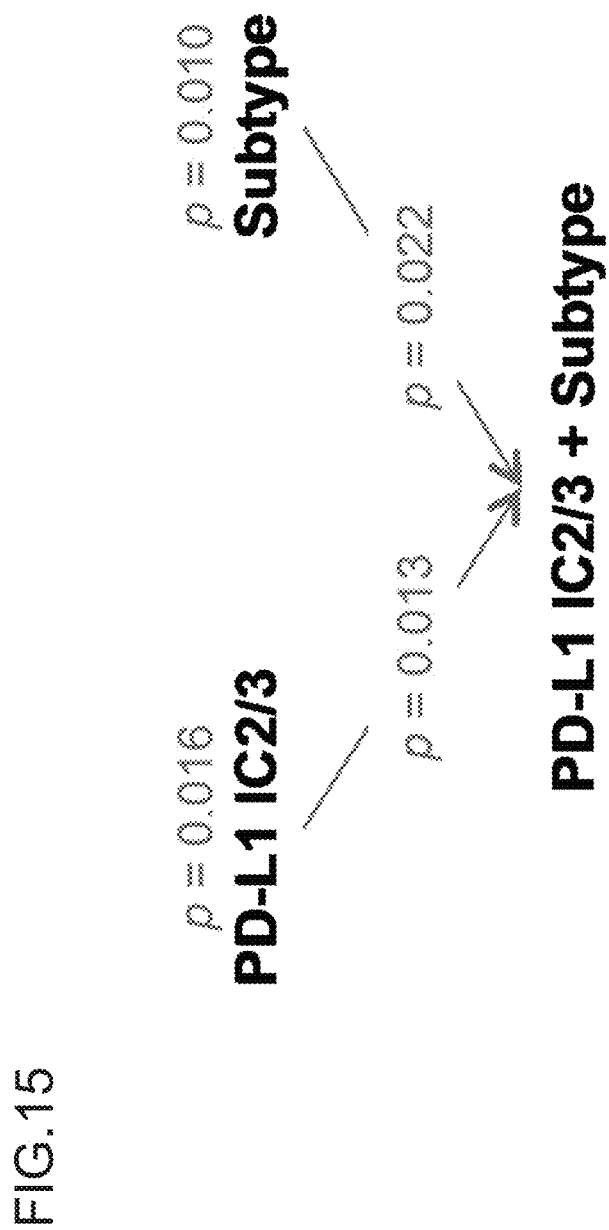
FIG. 15 is a diagram depicting the relationship between logistic regressions that fit response (CR/PR vs SD/PD) on one or more biomarkers: PD-L1 IHC IC score (IC0/1 vs IC2/3) and TCGA gene expression subtype.

Although PD-L1 IC status clearly is associated with atezolizumab response, incorporation of TCGA gene expression subtype into a model based on PD-L1 IC staining significantly improved the association with response (FIG. 15). Thus, disease subtype does not simply recapitulate the information already provided by PD-L1 expression in immune cells, but rather, provides independent and complementary information.

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method of treating a patient suffering from a bladder cancer, the method comprising administering to the patient a therapeutically effective amount of atezolizumab, wherein a tumor sample obtained from the patient has been determined to have a detectable expression level of PD-L1 in tumor-infiltrating immune cells that comprise about 5% or more of the tumor sample, and wherein the tumor sample obtained from the patient has been determined to be a The Cancer Genome Atlas (TCGA) luminal cluster II subtype tumor.

2. The method of claim 1, wherein:
   (i) the median overall survival time of a patient administered a therapeutically effective amount of atezolizumab is at least 8 months; or
   (ii) the objective response rate of a patient administered a therapeutically effective amount of atezolizumab is at least about 12%.

3. The method of claim 2, wherein:
   (i) the median overall survival time of a patient administered a therapeutically effective amount of atezolizumab is at least about 8.8 months; or
   (ii) the objective response rate of a patient administered a therapeutically effective amount of atezolizumab is about 18%.

4. The method of claim 1, wherein:
   (i) the median overall survival time of a patient administered a therapeutically effective amount of atezolizumab is at least 9 months; or
   (ii) the objective response rate of a patient administered a therapeutically effective amount of atezolizumab is at least about 14%.

5. The method of claim 4, wherein the objective response rate of a patient administered a therapeutically effective amount of atezolizumab is about 27%.

6. The method of claim 1, wherein the tumor sample obtained from the patient has been determined to have a detectable expression level of PD-L1 in tumor-infiltrating immune cells that comprise about 10% or more of the tumor sample.

7. The method of claim 1, wherein:
   (a) the expression level of at least one of CDKN2A, GATA3, FOXA1, and ERBB2 in the tumor sample obtained from the patient has been determined to be increased relative to a reference level of the at least one gene, and/or
   (b) the expression level of at least one of FGFR3, KRT5, KRT14, and EGFR in the tumor sample obtained from the patient has been determined to be decreased relative to a reference level of the at least one gene.

8. The method of claim 7, wherein:
   (a) the expression levels of CDKN2A, GATA3, FOXA1, and ERBB2 in the tumor sample obtained from the patient have been determined to be increased relative to reference levels of the genes, and/or
   (b) the expression levels of FGFR3, KRT5, KRT14, and EGFR in the tumor sample obtained from the patient have been determined to be decreased relative to reference levels of the genes.

9. The method of claim 1, wherein the expression level of miR-99a-5p or miR100-5p in the tumor sample obtained from the patient has been determined to be increased relative to a reference level of the micro RNA (miRNA).

10. The method of claim 9, wherein the expression levels of miR-99a-5p and miR100-5p in the tumor sample obtained from the patient have been determined to be increased relative to reference levels of the miRNAs.

11. The method of claim 1, wherein the expression level of at least one of CD8A, GZMA, GZMB, IFNG, CXCL9, CXCL10, PRF1, and TBX21 in the tumor sample obtained from the patient has been determined to be increased relative to a reference level of the at least one gene.

12. The method of claim 11, wherein the expression levels of at least CXCL9 and CXCL10 in the tumor sample obtained from the patient have been determined to be increased relative to reference levels of the genes.

13. The method of claim 1, wherein the tumor sample obtained from the patient has been determined to be a luminal cluster II subtype tumor according to expression of the following genes: FGFR3, CDKN2A, KRT5, KRT14, EGFR, GATA3, FOXA1, and ERBB2.

14. The method of claim 1, further comprising administering to the patient an effective amount of a second therapeutic agent.

15. The method of claim 14, wherein the second therapeutic agent is selected from the group consisting of a cytotoxic agent, a growth-inhibitory agent, a radiation therapy agent, and an anti-angiogenic agent, or a combination thereof.

16. The method of claim 1, wherein the bladder cancer is an urothelial bladder cancer.

17. The method of claim 16, wherein the urothelial bladder cancer is a muscle invasive urothelial bladder cancer.

18. The method of claim 16, wherein the urothelial bladder cancer is a metastatic urothelial bladder cancer.

19. The method of claim 16, wherein the urothelial bladder cancer is a locally advanced urothelial bladder cancer.

20. The method of claim 1, wherein the tumor sample is a formalin-fixed and paraffin-embedded (FFPE) tumor sample, an archival tumor sample, a fresh tumor sample, or a frozen tumor sample.

21. The method of claim 1, wherein the expression level of PD-L1 is a protein expression level.

22. The method of claim 21, wherein the protein expression level of PD-L1 is determined using a method selected from immunohistochemistry (IHC), immunofluorescence, flow cytometry, and Western blot.

23. The method of claim 22, wherein the protein expression level of PD-L1 is determined using IHC and/or wherein the protein expression level of PD-L1 is detected using an anti-PD-L1 antibody.

24. The method of claim 1, wherein the expression level of PD-L1 is measured using an automated staining instrument.

25. The method of claim 1, wherein the expression level of PD-L1 is an mRNA expression level.

26. The method of claim 25, wherein the mRNA expression level of PD-L1 is determined using a method selected from quantitative polymerase chain reaction (qPCR), reverse transcription qPCR (RT-qPCR), RNA sequencing, microarray analysis, in situ hybridization, and serial analysis of gene expression (SAGE).

27. A method for (i) determining whether a patient suffering from a bladder cancer is likely to respond to treatment comprising atezolizumab or (ii) predicting responsiveness of a patient suffering from a bladder cancer to treatment comprising atezolizumab, the method comprising:
  determining the expression level of PD-L1 in tumor-infiltrating immune cells in a tumor sample obtained from the patient,
  wherein a detectable expression level of PD-L1 in tumor-infiltrating immune cells that comprise about 5% or more of the tumor sample indicates that the patient is likely to respond to treatment comprising atezolizumab, wherein the tumor sample obtained from the patient has been determined to be a luminal cluster II subtype tumor; and administering to the patient a therapeutically effective amount of atezolizumab.

28. The method of claim 27, wherein the tumor sample obtained from the patient has been determined to have a detectable expression level of PD-L1 in tumor-infiltrating cells that comprise at least about 10% of the tumor sample.

29. The method of claim 27, wherein the tumor sample obtained from the patient has been determined to be a luminal cluster II subtype tumor according to expression of the following genes: FGFR3, CDKN2A, KRT5, KRT14, EGFR, GATA3, FOXA1, and ERBB2.

30. The method of claim 27, wherein the bladder cancer is an urothelial bladder cancer.

31. The method of claim 30, wherein the urothelial bladder cancer is a muscle invasive urothelial bladder cancer.

32. The method of claim 27, wherein the expression level of PD-L1 is measured an automated staining instrument.

33. A method for selecting a therapy for a patient suffering from a bladder cancer, the method comprising:
  determining the expression level of PD-L1 in tumor-infiltrating immune cells in a tumor sample obtained from the patient,
  selecting a therapy comprising atezolizumab for the patient based on a detectable expression level of PD-L1 in tumor-infiltrating immune cells that comprise about 5% or more of the tumor sample, wherein a detectable expression level of PD-L1 in tumor-infiltrating immune cells that comprise about 5% or more of the tumor sample indicates that the patient is likely to respond to treatment comprising atezolizumab, wherein the tumor sample obtained from the patient has been determined to be a TCGA luminal cluster II subtype tumor; and administering to the patient a therapeutically effective amount of atezolizumab.

* * * * *

SEQUENCE LISTING

```
<160> NUMBER OF SEQ ID NOS: 33

<210> SEQ ID NO 1
<211> LENGTH: 440
<212> TYPE: PRT
<213> ORGANISM: Artificial Sequence
<220> FEATURE:
<223> OTHER INFORMATION: Synthetic Polypeptide

<400> SEQUENCE: 1

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125
```

```
Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 2
<211> LENGTH: 214
<212> TYPE: PRT
<213> ORGANISM: Artificial Sequence
<220> FEATURE:
<223> OTHER INFORMATION: Synthetic Polypetide

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45
```

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115

<210> SEQ ID NO 4
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 5
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (6)..(6)
<223> OTHER INFORMATION: Xaa is Asp or Gly

<400> SEQUENCE: 5

Gly Phe Thr Phe Ser Xaa Ser Trp Ile His
1               5                   10

<210> SEQ ID NO 6
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (4)..(4)
<223> OTHER INFORMATION: Xaa is Ser or Leu
<220> FEATURE:
<221> NAME/KEY: MOD_RES
<222> LOCATION: (10)..(10)
<223> OTHER INFORMATION: Xaa is Thr or Ser

<400> SEQUENCE: 6

Ala Trp Ile Xaa Pro Tyr Gly Gly Ser Xaa Tyr Tyr Ala Asp Ser Val
1               5                   10                  15

Lys Gly

<210> SEQ ID NO 7
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 7

Arg His Trp Pro Gly Gly Phe Asp Tyr
1               5

<210> SEQ ID NO 8
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 9
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 9

Trp Val Arg Gln Ala Pro Gly Lys Gly Leu Glu Trp Val
1               5                   10

<210> SEQ ID NO 10
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 10

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 11
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 11

Trp Gly Gln Gly Thr Leu Val Thr Val Ser Ala
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (5)..(5)
<223> OTHER INFORMATION: Xaa is Asp or Val
<220> FEATURE:
<221> NAME/KEY: MOD_RES
<222> LOCATION: (6)..(6)
<223> OTHER INFORMATION: Xaa is Val or Ile
<220> FEATURE:
<221> NAME/KEY: MOD_RES
<222> LOCATION: (7)..(7)
<223> OTHER INFORMATION: Xaa is Ser or Asn
<220> FEATURE:
<221> NAME/KEY: MOD_RES
<222> LOCATION: (9)..(9)
<223> OTHER INFORMATION: Xaa is Ala or Phe
<220> FEATURE:
<221> NAME/KEY: MOD_RES
<222> LOCATION: (10)..(10)
<223> OTHER INFORMATION: Xaa is Val or Leu

```
<400> SEQUENCE: 12

Arg Ala Ser Gln Xaa Xaa Xaa Thr Xaa Xaa Ala
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (4)..(4)
<223> OTHER INFORMATION: Xaa is Phe or Thr
<220> FEATURE:
<221> NAME/KEY: MOD_RES
<222> LOCATION: (6)..(6)
<223> OTHER INFORMATION: Xaa is Tyr or Ala

<400> SEQUENCE: 13

Ser Ala Ser Xaa Leu Xaa Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (3)..(3)
<223> OTHER INFORMATION: Xaa is Tyr, Gly, Phe, or Ser
<220> FEATURE:
<221> NAME/KEY: MOD_RES
<222> LOCATION: (4)..(4)
<223> OTHER INFORMATION: Xaa is Leu, Tyr, Phe, or Trp
<220> FEATURE:
<221> NAME/KEY: MOD_RES
<222> LOCATION: (5)..(5)
<223> OTHER INFORMATION: Xaa is Tyr, Asn, Ala, Thr, Gly, Phe, or Ile
<220> FEATURE:
<221> NAME/KEY: MOD_RES
<222> LOCATION: (6)..(6)
<223> OTHER INFORMATION: Xaa is His, Val, Pro, Thr, or Ile
<220> FEATURE:
<221> NAME/KEY: MOD_RES
<222> LOCATION: (8)..(8)
<223> OTHER INFORMATION: Xaa is Ala, Trp, Arg, Pro, or Thr

<400> SEQUENCE: 14

Gln Gln Xaa Xaa Xaa Xaa Pro Xaa Thr
1               5

<210> SEQ ID NO 15
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 16
<211> LENGTH: 15
<212> TYPE: PRT
```

```
<213> ORGANISM: Artificial Sequence
<220> FEATURE:
<223> OTHER INFORMATION: Synthetic Polypeptide

<400> SEQUENCE: 16

Trp Tyr Gln Gln Lys Pro Gly Lys Ala Pro Lys Leu Leu Ile Tyr
1               5                   10                  15

<210> SEQ ID NO 17
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 17

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 18
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 18

Phe Gly Gln Gly Thr Lys Val Glu Ile Lys Arg
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 19

Gly Phe Thr Phe Ser Asp Ser Trp Ile His
1               5                   10

<210> SEQ ID NO 20
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 20

Ala Trp Ile Ser Pro Tyr Gly Gly Ser Thr Tyr Tyr Ala Asp Ser Val
1               5                   10                  15

Lys Gly

<210> SEQ ID NO 21
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 21

Arg His Trp Pro Gly Gly Phe Asp Tyr
1               5
```

<210> SEQ ID NO 22
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 22

Arg Ala Ser Gln Asp Val Ser Thr Ala Val Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 23

Ser Ala Ser Phe Leu Tyr Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 24

Gln Gln Tyr Leu Tyr His Pro Ala Thr
1               5

<210> SEQ ID NO 25
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 26
<211> LENGTH: 122
<212> TYPE: PRT
<213> ORGANISM: Artificial Sequence
<220> FEATURE:

<223> OTHER INFORMATION: Synthetic Polypeptide

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys
        115                 120

<210> SEQ ID NO 27
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 27

Trp Gly Gln Gly Thr Leu Val Thr Val Ser Ser
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 28

Phe Gly Gln Gly Thr Lys Val Glu Ile Lys
1               5                   10

<210> SEQ ID NO 29
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 30
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 30

-continued

Trp Val Arg Gln Ala Pro Gly Lys Gly Leu Glu Trp Val Ala
1               5                   10

<210> SEQ ID NO 31
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 31

Trp Gly Gln Gly Thr Leu Val Thr Val Ser Ser Ala Ser Thr Lys
1               5                   10                  15

<210> SEQ ID NO 32
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
                20                  25                  30

Trp Ile His Trp Val Arg Gln Ala Pro Gly Lys Gly Leu Glu Trp Val
            35                  40                  45

Ala Trp Ile Ser Pro Tyr Gly Gly Ser Thr Tyr Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala

```
                275                 280                 285
Lys Thr Lys Pro Arg Glu Glu Gln Tyr Ala Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly
        435                 440                 445

<210> SEQ ID NO 33
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 33

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Ser Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Leu Tyr His Pro Ala
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
```

-continued

```
               195                 200                 205
Phe Asn Arg Gly Glu Cys
    210
```

UNITED STATES PATENT AND TRADEMARK OFFICE
CERTIFICATE OF CORRECTION

| | |
|---|---|
| PATENT NO. | : 11,535,671 B2 |
| APPLICATION NO. | : 16/655495 |
| DATED | : December 27, 2022 |
| INVENTOR(S) | : Hegde et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 238 days.

Signed and Sealed this
Fourteenth Day of January, 2025

Derrick Brent
*Acting Director of the United States Patent and Trademark Office*